(12) United States Patent
Black et al.

(10) Patent No.: US 7,532,314 B1
(45) Date of Patent: May 12, 2009

(54) SYSTEMS AND METHODS FOR BIOLOGICAL AND CHEMICAL DETECTION

(75) Inventors: Rodney S. Black, Galloway, OH (US);
Jeffrey P. Carpenter, Lancaster, OH (US); Johnway Gao, Hilliard, OH (US);
Jerome U. Gilberry, Raleigh, NC (US);
William A. Ivancic, Gahanna, OH (US);
John J. Kester, Powell, OH (US); Clark A. Morrow, Hilliard, OH (US)

(73) Assignee: Battelle Memorial Institute, Columbus, OH (US)

( * ) Notice: Subject to any disclaimer, the term of this patent is extended or adjusted under 35 U.S.C. 154(b) by 292 days.

(21) Appl. No.: 11/486,861

(22) Filed: Jul. 14, 2006

Related U.S. Application Data

(60) Provisional application No. 60/699,132, filed on Jul. 14, 2005, provisional application No. 60/798,244, filed on May 5, 2006.

(51) Int. Cl.
*G01J 3/44* (2006.01)
*G01N 21/64* (2006.01)
*G01N 21/65* (2006.01)

(52) U.S. Cl. .............................. 356/73; 356/36; 356/38; 356/301

(58) Field of Classification Search ................... 356/36, 356/38, 73, 301
See application file for complete search history.

(56) References Cited

U.S. PATENT DOCUMENTS 2,721,495 A  10/1955  Schaefer
4,255,172 A  3/1981  Smith (Continued)

FOREIGN PATENT DOCUMENTS

DE     102004008762 A1 *  9/2005

(Continued)

OTHER PUBLICATIONS

Rosch et al, Chemotaxonomic Identification of Single Bacteria by Micro-Raman Spectroscopy: Application to Clean-Room-Relevent Biological Contaminations, Applied and Environmental Microbiology, Mar. 2005, vol. 71, No. 3, pp. 1626-1637.*

(Continued)

*Primary Examiner*—F. L Evans
(74) *Attorney, Agent, or Firm*—Stevens & Showalter LLP

(57) ABSTRACT

A biological and chemical detection system is provided that detects and identifies biological and/or chemical particulates of interest. The biological and chemical detection system comprises a collector, a first optical device, a second optical device and a processor. The collector is configured to deposit particulates drawn from a fluid stream onto a sample substrate to define a sample area. The first optical device derives first data relative to at least a portion of the sample area, which is analyzed to determine at least one field of view and/or specific target location. The second optical device then interrogates the sample area at each determined target location, e.g., using Raman spectroscopy, to produce interrogation data. The processor determines whether the sample area includes predetermined biological or chemical particulates of interest based upon an analysis of the interrogation data and triggers an event such as an alarm or message if the predetermined biological or chemical particulates of interest are identified.

25 Claims, 31 Drawing Sheets

U.S. PATENT DOCUMENTS

| | | | |
|---|---|---|---|
| 4,868,398 | A | 9/1989 | Mulcey et al. |
| 4,942,297 | A | 7/1990 | Johnson et al. |
| 5,498,271 | A | 3/1996 | Marple et al. |
| 5,701,012 | A | 12/1997 | Ho |
| 5,717,147 | A | 2/1998 | Basch et al. |
| 5,866,430 | A | 2/1999 | Grow |
| 5,895,922 | A | 4/1999 | Ho |
| 5,989,824 | A | 11/1999 | Birmingham et al. |
| 6,010,554 | A | 1/2000 | Birmingham et al. |
| 6,040,191 | A | 3/2000 | Grow |
| 6,062,392 | A | 5/2000 | Birmingham et al. |
| 6,110,247 | A | 8/2000 | Birmingham et al. |
| 6,267,016 | B1 | 7/2001 | Call et al. |
| 6,363,800 | B1 | 4/2002 | Call et al. |
| 6,386,015 | B1 | 5/2002 | Rader et al. |
| 6,435,043 | B1 | 8/2002 | Ferguson et al. |
| 6,483,581 | B1 | 11/2002 | Ben-Amotz et al. |
| 6,506,345 | B1 | 1/2003 | Lee et al. |
| 6,510,727 | B2 | 1/2003 | Reiter et al. |
| 6,654,118 | B2 * | 11/2003 | Bruce ................... 356/301 |
| 6,695,146 | B2 | 2/2004 | Call et al. |
| 6,698,592 | B2 | 3/2004 | Kenning et al. |
| 6,707,548 | B2 | 3/2004 | Kreimer et al. |
| 6,717,668 | B2 | 4/2004 | Treado et al. |
| 6,729,196 | B2 | 5/2004 | Moler et al. |
| 6,732,569 | B2 | 5/2004 | Ondov et al. |
| 6,734,962 | B2 | 5/2004 | Treado et al. |
| 6,765,668 | B2 | 7/2004 | Gardner, Jr. et al. |
| 6,788,860 | B1 | 9/2004 | Treado et al. |
| 6,799,119 | B1 | 9/2004 | Voorhees et al. |
| 6,806,465 | B2 | 10/2004 | Anderson et al. |
| 6,841,773 | B2 | 1/2005 | McLoughlin et al. |
| 7,057,721 | B2 * | 6/2006 | Gardner et al. ............ 356/301 |
| 2002/0003210 | A1 | 1/2002 | Marcus |
| 2002/0030811 | A1 | 3/2002 | Schindler |
| 2002/0070148 | A1 | 6/2002 | Roberts et al. |
| 2002/0081748 | A1 | 6/2002 | Roberts et al. |
| 2002/0184969 | A1 | 12/2002 | Kodas et al. |
| 2003/0010907 | A1 | 1/2003 | Hayek et al. |
| 2003/0020768 | A1 | 1/2003 | Renn |
| 2003/0082825 | A1 | 5/2003 | Lee et al. |
| 2003/0098422 | A1 | 5/2003 | Silcott et al. |
| 2003/0223063 | A1 | 12/2003 | Hill et al. |
| 2004/0010379 | A1 | 1/2004 | Craig et al. |
| 2004/0016308 | A1 | 1/2004 | Rogers et al. |
| 2004/0065159 | A1 | 4/2004 | Sioutas |
| 2004/0068193 | A1 | 4/2004 | Barnes et al. |
| 2004/0118222 | A1 | 6/2004 | Cornish et al. |
| 2004/0121402 | A1 | 6/2004 | Harper et al. |
| 2004/0197493 | A1 | 10/2004 | Renn et al. |
| 2004/0222372 | A1 | 11/2004 | McLoughlin et al. |
| 2004/0227938 | A1 | 11/2004 | Craig |
| 2004/0232052 | A1 | 11/2004 | Call et al. |
| 2005/0028616 | A1 | 2/2005 | Marple et al. |
| 2005/0041774 | A1 | 2/2005 | Saitoh et al. |
| 2005/0046664 | A1 | 3/2005 | Renn |
| 2005/0070025 | A1 | 3/2005 | Moordian et al. |
| 2005/0079349 | A1 | 4/2005 | Hampden-Smith et al. |
| 2005/0105079 | A1 | 5/2005 | Pletcher et al. |

FOREIGN PATENT DOCUMENTS

| | | |
|---|---|---|
| EP | 0 421 156 A2 | 4/1991 |
| WO | 93/07471 A | 4/1993 |
| WO | 96/29925 A2 | 10/1996 |
| WO | WO 03/036273 A1 | 5/2003 |
| WO | WO 2006/001852 A2 | 1/2006 |
| WO | WO 2006/091221 A2 | 8/2006 |

OTHER PUBLICATIONS

Gard, E., Mayer, J.E., Morrical, B.D., Dienes, T. Fergeson, D.P., and Prather, K.A.; "Real-Time Analysis of Individual Atmospheric Aerosol Particles: Design and Performance of a Portable ATOFMS," Anal. Chem., 1997, 69, 4083-4091.

Hansen, A.D.A., Rosen H., and Novakov, T.; "The aethalometer—an instrument for the real-time measrement of optical absorption by aerosol particles," Sci. Total Environ., 1984, 36, 191.

Jayne, J.T., Leard, D.C., Zhang, X., Davidovits, P. Smith, K.A. Kolb, C.E., Worsnop, D.R..; "Development of an Aerosol Mass Spectrometer for Size and Composition Analysis of Submicron Particles," Aerosol Sci. Tech., 2000, 34, 49-70.

McCreery R.L., Raman Spectroscopy for Chemical Analysis, Chemical Analysis, vol. 157, 2000.

Prather, K.A., Nordmeyer, T., Salt, K.; "Real-Time Characterization of Individual Aerosol Particles Using Time-of-Flight Mass Spectrometry," Anal. Chem., 1994, 66, 1403-1407.

Rupprecht & Patashnick, Co., Patent pending. Environmental Technology Verification Report, Series 8400S Ambient Particulate Sulfate Monitor, Aug. 2001.

Rupprecht, G., Patashnick, H., Beeson, D.E., Green, R.N. and Meyer, M.B.; "A New Automated Monitor for the Measurement of Particulate Carbon in the Atmosphere," Presented at Particulate Matter: Health and Regulatory Issues, Pittsburgh, PA, Apr. 4-6, 1995.

Stolzenburg, M.R. and Hering, S.V., "Method for the Automated Measurement of Fine Particle Nitrate in the Atmosphere," Environ. Sci. Technol., 2000, 34, 907-914.

Rosch, Petra, Harz, Michaela, Peschke, Klaus-Dieter, Ronneberger, Olaf, Burkhardt, Hans, Schule, Andreas, Schmauz, Gunther, Lankers, Markus, Hoffer, Stefan, Thiele, Hans, Motzkus, Hans-Walter, and Popp, Jurgen, On-Line Monitoring and Identification of Bioaerosols, Anal. Chemistry, vol. 78, No. 7, Apr. 1, 2006.

Dycor Biological Detection Products, www.dycor.com/products/biologicalDet.htm, Jun. 6, 2005.

Humphries, Allen, A Simple Guide To How Aerosol Particle Counters Work, www.pmeasuring.com/particleCounting/appNotes/aerosol/app59air/viewHtml, Apr. 18, 2005.

Patrick Wach; International Search Report and Written Opinion for PCT Application No. PCT/US2006/027368; Dec. 18, 2006; European Patent Office; Rijswijk The Netherlands.

Puk Groeneveld-van der Spek; International Search Report and Written Opinion for PCT Application No. PCT/US2006/027689; May 18, 2007; European Patent Office; Rijswijk the Netherlands.

Nicolas Ruchaud; Communication pursuant to Article 94(3) EPC for EPO Application No. 06 787 297.8; May 19, 2008; European Patent Office, Rijswijk The Netherlands.

Kara E. Geisel; Office Action in U.S. Appl. No. 11/486,946; Apr. 18, 2008; U.S. Patent and Trademark Office; Alexandria VA.

Fannie L. Evans; Office Action in U.S. Appl. No. 11/486,619; Sep. 15, 2008; U.S. Patent and Trademark Office; Alexandria VA.

Translation of DE 102004008762 A1; published Sep. 8, 2005; Applicant: Popp et al.

* cited by examiner

SYSTEMS AND METHODS FOR BIOLOGICAL AND CHEMICAL DETECTION

CROSS REFERENCE TO RELATED APPLICATIONS

This application claims the benefit of U.S. Provisional Patent Application Ser. No. 60/699,132, filed Jul. 14, 2005 entitled "BIOLOGICAL AND CHEMICAL DETECTION SYSTEM" and U.S. Provisional Patent Application Ser. No. 60/798,244 entitled "PARTICULATE DETECTION SYSTEM", filed May 5, 2006, the disclosures of which are hereby incorporated by reference.

BACKGROUND OF THE INVENTION

The present invention relates in general to systems and methods for the separation and collection of particulates from a fluid stream and in particular, to systems and methods for the collection, detection and/or analysis of sampled airborne biological and chemical particulates.

The monitoring of atmospheric particulate matter (PM) has received an increasing amount of attention in recent years because of the potential impact of particulates on radiative and climatic processes, on human health and because of the role particles play in atmospheric transport and deposition of pollutants. For example, it may be desirable to analyze the air in a predetermined location for particulates that fall within a range of sizes that can be inhaled, such as naturally occurring or artificially produced airborne pathogens, allergens, bacteria, viruses, fungi and biological or chemical agents that are found in or are otherwise introduced into the location.

As another example, it may be desirable to detect the presence of particular airborne particulates in semiconductor clean rooms, pharmaceutical production facilities and biotechnology laboratories to verify that there has been no contamination produced in such environments that would create undesirable environmental exposures or adversely affect manufacturing, testing or experimental processes. Similarly, the ability to detect the presence of particular airborne particulates in hospitals, nursing homes, rehabilitation centers and other care facilities may be beneficial to assist in preventing the spread of disease, infection or harmful bacteria.

The monitoring of atmospheric particulate matter further finds application for assessments of human health risk, environmental contamination and for compliance with National Air Quality Standards (NAAQS), e.g., to monitor the air in public and commercial building air purification and distribution systems, work sites such as mines, sewage facilities, agricultural and manufacturing facilities, outside areas such as street corners, flues and smokestacks and other locations where it is desirable to monitor environmental hygiene, such as residences exposed to microorganisms, plants or animals.

SUMMARY OF THE INVENTION

The various embodiments of the present invention provide biological and chemical detection systems that collect, detect and/or identify biological and chemical particulates of interest.

According to an embodiment of the present invention, a biological and chemical detection system comprises a collector, an optical interrogation station and a processor. The collector is configured to deposit particulates drawn from a fluid stream onto a sample substrate to define a sample area. The optical interrogation station derives data relative to at least a portion of the sample area, which is analyzed by the processor to determine one or more target locations within the sample area. The optical interrogation station then interrogates the sample area at the determined target locations to produce interrogation data. For example, the target locations may each pinpoint a specific particulate of interest within a collected sample. The processor determines whether the sample area includes predetermined biological or chemical particulates of interest based upon an analysis of the interrogation data, e.g., by analyzing the targeted particulate(s), and triggers an event such as an alarm or message if the predetermined biological or chemical particulates of interest are identified.

According to another embodiment of the present invention, a biological and chemical detection system comprises a storage station, a collection station, an optical interrogation station and a transport. The storage station is configured to store one or more sample substrates, which may comprise individual storage elements, or a continuous element such as a tape or ribbon. The collection station is configured to deposit particulates drawn from a fluid stream onto a sample substrate to define a sample area. The optical interrogation station is configured to analyze at least a portion of the sample area for particulates of interest, and the transport, e.g., a rotary stage or tape reel system, is configured to transport sample substrates between the storage station, collection station and optical interrogation station.

The collection station may comprise a collector having a nozzle that ejects a fluid stream towards the sample area such that the stream exiting the nozzle may be reversed and drawn back out through the collector. The collector may also be configured such that a flow rate of the stream is controlled by a size of the nozzle. For example, the collector may comprise an impactor operable to impact particulates between approximately 1 $\mu$m and 10 $\mu$m on the sample substrate.

The optical interrogation station comprises a first optical device and a second optical device. The first optical device interrogates and extracts first data relative to one or more sections of the sample area. A processor determines at least one target location from the first data, and the second optical device interrogates the sample area at each determined target location to produce interrogation data. For example, the target locations may each pinpoint a specific particulate of interest within a collected sample. The processor is further configured to determine whether the sample area includes predetermined biological or chemical particulates of interest based upon an analysis of the interrogation data, e.g., by analyzing the targeted particulate(s), and trigger an event if the predetermined biological or chemical particulates of interest are identified.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals, and in which.

DETAILED DESCRIPTION OF THE INVENTION

In the following detailed description of the preferred embodiments, reference is made to the accompanying drawings that form a part hereof, and in which is shown by way of illustration, and not by way of limitation, specific preferred embodiments in which the invention may be practiced. It is to be understood that other embodiments may be utilized and that changes may be made without departing from the spirit and scope of the present invention.

Figure 1:
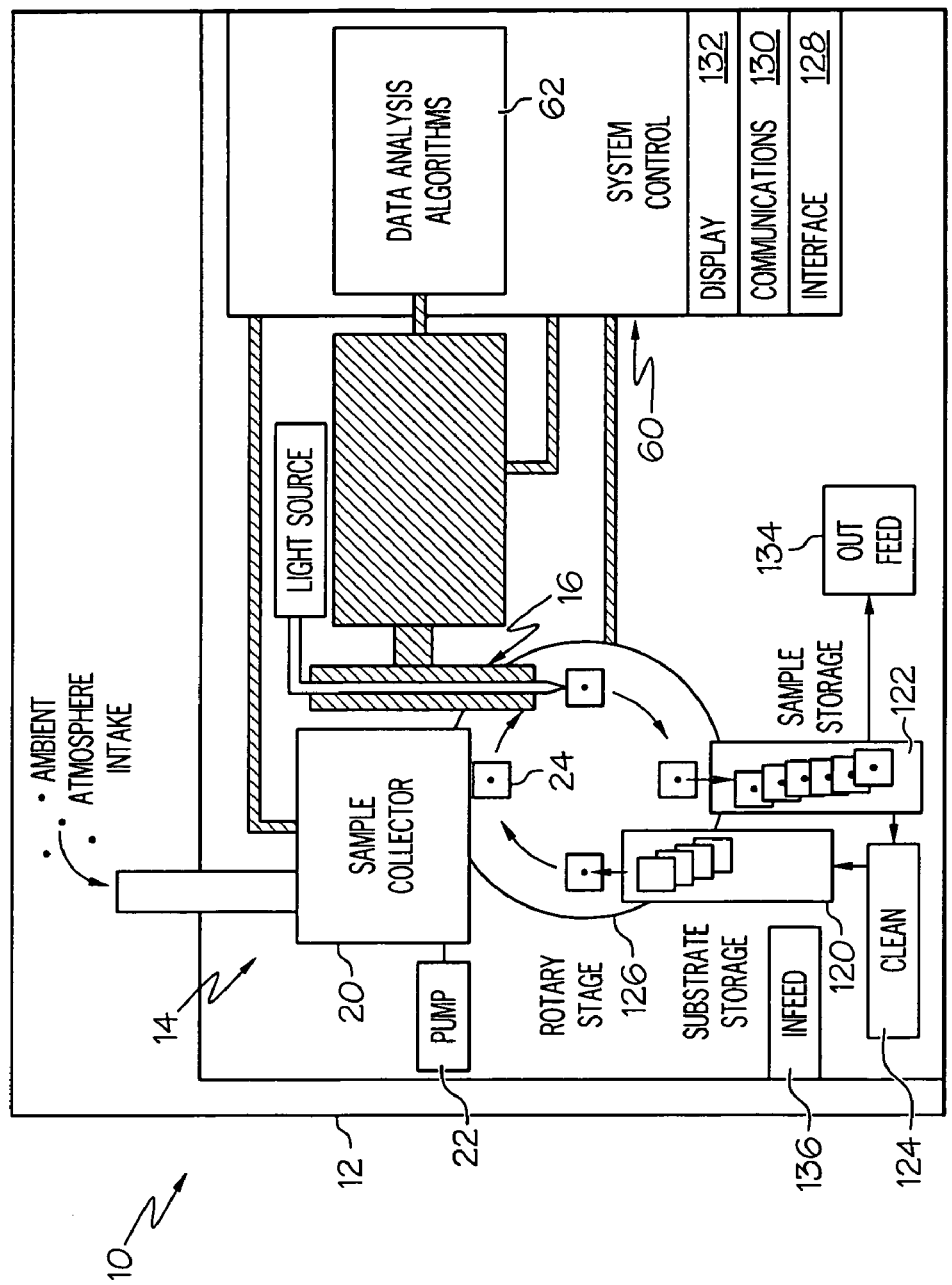
FIG. 1 is a schematic illustration of a biological and chemical detection system according to an embodiment of the present invention.

Referring now to the drawings, and particularly to FIG. 1, a biological and chemical detection system 10 for detecting and identifying biological or chemical particulates of interest in a fluid stream includes generally, a housing 12 that supports a collection station 14, an optical interrogation station 16 and a storage station 18.

The collection station 14 includes a collector 20 and a pump 22. The pump 22 draws and accelerates a fluid stream, such as from the ambient air, through the collector 20. Particulate matter that is entrained in the stream is extracted and deposited onto a sample substrate 24 adjacent to the collector 20 in a relatively small, defined sample area. A single vacuum pump 22 is illustrated in FIG. 1 for purposes of clarity of discussion herein. However, multiple vacuum pumps 22 and corresponding coupling arrangements may be implemented in practice as the specific application dictates.

Solid Surface Small Area Impactor

Figure 2:
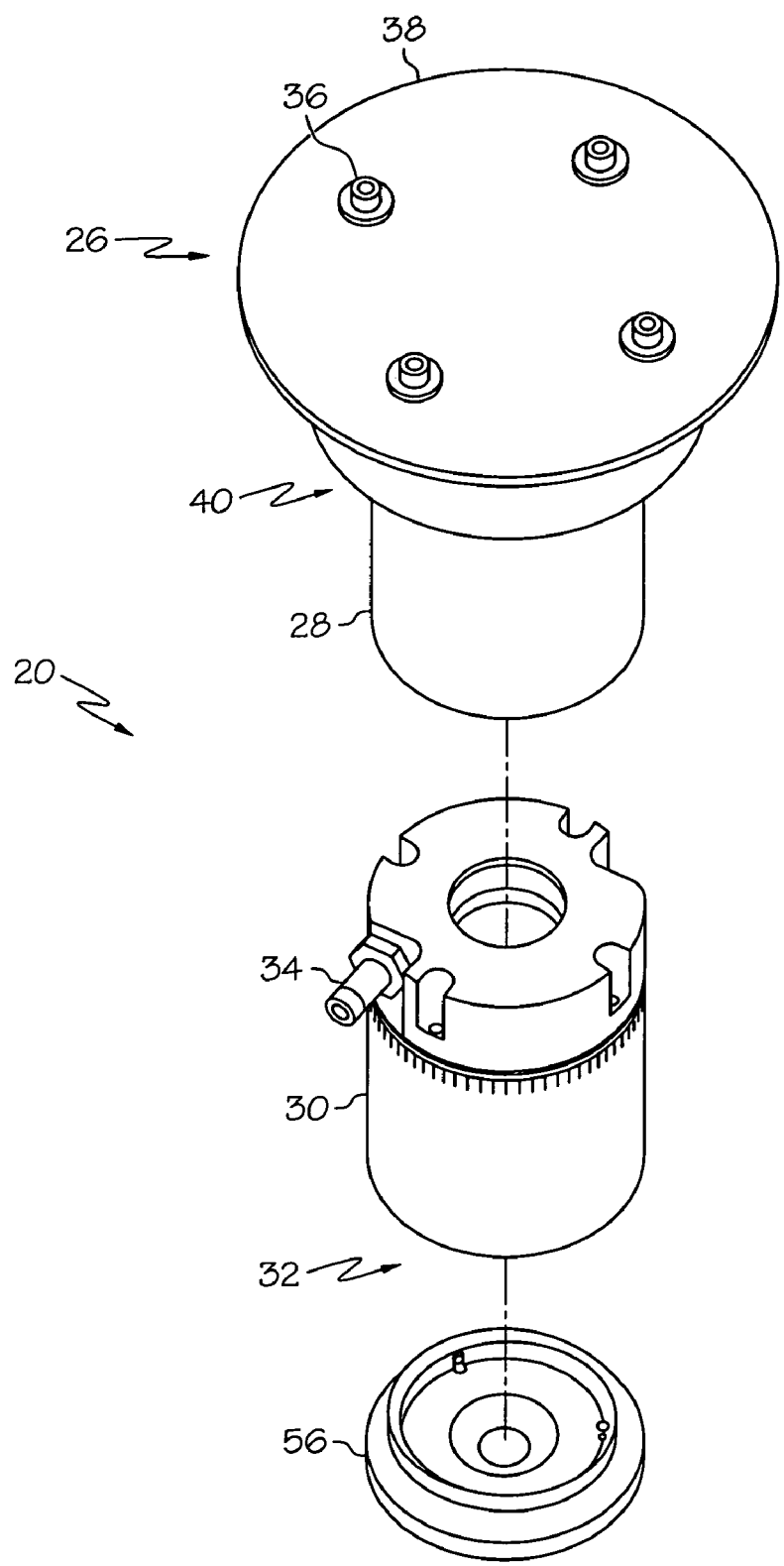
FIG. 2 is an assembly illustration of an exemplary collector that may be used with the biological and chemical detection system of FIG. 1.
Figure 3:
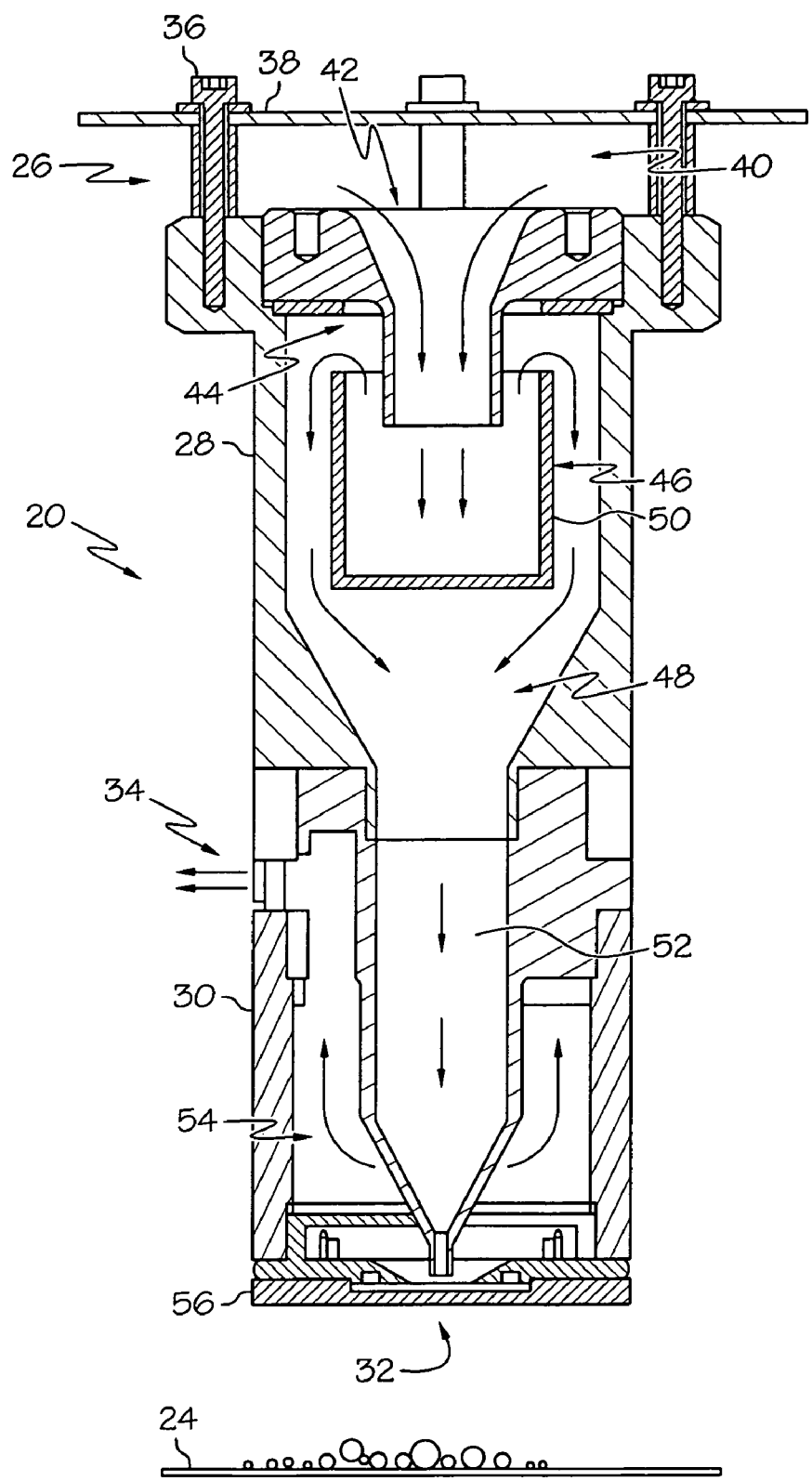
FIG. 3 is a cross sectional view of the collector of FIG. 2.

Referring to FIGS. 2-3, the collector 20 includes an inlet 26, a pre-impactor 28, an impactor 30, a nozzle 32 and a pump coupling arrangement 34. The inlet 26 is physically connected to the pre-impactor 28 by a coupling device, such as screws 36 or other suitable securing arrangement. Covers or other devices may be provided to prevent foreign objects from entering the collector while the inlet(s) are removed from the collector, e.g., during transportation of the biological and chemical detection system 10.

With particular reference to FIG. 3, the inlet 26, which extends outside of the housing 12, includes a cap 38, an inlet opening 40 and a generally funnel shaped first fluid passageway 42. The fluid stream enters the inlet 26 through the inlet opening 40 and is drawn through the first fluid passageway 42 into the pre-impactor 28. The cap 38 may serve as a rain plate or other environmental protection structure that prevents the collection system from ingesting large particles including rain drops, etc. The inlet opening 40 comprises substantially the entirety of the circumference of the inlet 26 as illustrated, but other opening arrangements may alternatively be implemented. Additionally, the first fluid passageway 42 may be of any shape length necessary to locate the sample collection point to a desired location. In this regard, the first fluid passageway 42 may comprise one or more intermediate structures such as extension tubes that serve to extend the distance between the inlet 26 and the pre-impactor 28.

The pre-impactor 28 includes a pre-impactor input 44, a particulate filtering arrangement 46 and a second fluid passageway 48. The fluid stream is directed through the pre-impactor input 44 via the first fluid passageway 42 to the particulate filtering arrangement 46. As shown, the particulate filtering arrangement 46 is implemented as a cup 50 that collects and holds particulates that exceed a predetermined size, e.g., particulates greater than approximately 10 μm. The filtered fluid stream is drawn out of the cup 50 and is directed into the second fluid passageway 48 to the impactor 30.

The impactor 30 accelerates the fluid stream through a third fluid passageway 52 and out the nozzle 32 towards the sample substrate 24 to form a sample that is contained in a small, definable sample area. Under the above arrangement, particle impaction in the sample area is governed by the dimensionless Stokes number (Stk) according to the expression:

$$Stk = \frac{\rho_{particle} C_c d_{particle}^2 V}{9 \eta_{air} d_{impactor}}$$

where:

$\rho_{particle}$ is the particle density, $C_c$ is the slip correction factor, $d^2_{particle}$ is the particle diameter, V is the velocity of the air jet out of the nozzle, $\eta_{air}$ is the air viscosity and $d_{impactor}$ or is the nozzle diameter.

As the fluid stream impacts the sample substrate 24, particulates generally within a designed-for size range are trapped on the surface of the substrate material and the fluid stream is drawn back towards the impactor 30 through a fourth fluid passageway 54 to the coupling arrangement and onto the pump 22. Thus, the airflow is reversed after the impaction point and is pulled out the top of the collector 20. The air is exhausted outside the housing 12 at some distance from the inlet opening 40 so as not to re-introduce previously sampled air back into the collector 20.

As will be seen in greater detail below, the reversal of the airflow after impaction allows the collector 20 to remain generally above and avoid significant interference with the sample substrate 24, which enables the sample substrate 24 to be easily advanced, changed out, replaced or otherwise adjusted. The positioning of the collector 20 over the sample substrate 24 and the corresponding reversal of airflow direction after impaction further allows the collector 20 to be integrated into an automated sample collection system as will be described in greater detail herein.

As an example, the impactor 30 may have a footprint of approximately 2 inches by 2 inches and a height of approximately 3 inches. However, the impactor 30 may comprise other suitable impaction size arrangements. Moreover, the impactor 30 may be implemented as a virtual impactor, cascade impactor or other suitable configuration, depending upon the specific sampling requirements. The pump 22 may be implemented for example, using a Gast Model SAA-V108-NQ oil-less rocking piston vacuum pump, which is operable such that a the fluid stream travels at a suitable flow rate, e.g., approximately in the range of 1-100 liters per minute (LPM) through the collector 20 and out through the nozzle 32.

The pre-impactor 28 is optional, but may be utilized for example, where it is desirable to filter particles that exceed a predetermined size requirement from the fluid stream. Filtering large particulates may be desirable for example, where the biological and chemical detection system 10 is monitoring particulates that fall within a size range that can be inhaled. The pre-impactor 28 may use alternative particle size filtering techniques and may be implemented using any suitable structure, e.g., a virtual impactor.

With reference to FIGS. 1 and 3 generally, the inside diameter of the nozzle 32 of the collector 20, the distance between the nozzle 32 and the sample substrate 24 and the flow rate of the fluid stream drawn by the pump 22 define parameters that affect the size range of particles that are collected on the sample substrate 24. As such, depending upon the intended application, any one or more of the above-identified parameters may be made variable to provide a range of control to the particulate sizes captured on the sample substrate 24. Additionally, the collector 20 flow rate may use the diameter of nozzle 32 as a critical orifice. That is, the flow rate may be controlled by the diameter of nozzle 32, e.g., if a proper vacuum is maintained through the collector 20. As an example, the nozzle 32 may have an inner diameter of approximately 1.5 mm. Under this arrangement, the fluid stream that passes through the nozzle 32 may deposit a sample on the sample substrate 24 that is generally less than 2 mm in diameter and may be 1 mm in diameter or smaller.

Referring to FIGS. 2-3, the collector 20 may also include an optional end cap 56. The end cap 56 is positioned adjacent to the nozzle 32 and may screw onto or otherwise couple to the impactor 30 using any suitable arrangement. The end cap 56 may be provided to set the distance between the sample substrate 24 and the nozzle 32. One characteristic of the illustrated collector 20 is that the distance between the nozzle 32 and the sample substrate 24 defines a parameter that affects the range of particulate sizes that are collected onto the sample substrate 24. As such, the end cap 56 may optionally be made adjustable so as to variably set the nozzle to sample substrate distance, e.g., as a rotatable graduated cylinder that threads up and down relative to the impactor 30.

In one exemplary application, the biological and chemical detection system 10 may be configured to sample the air for pathogens, allergens, bacteria, viruses, fungi, biological agents, other viable microorganisms and/or chemical particulates that fall within a range of sizes that can be inhaled. For example, the biological and chemical detection system 10 may be used to discriminate nitrate and sulfate, ammonium, fungal spores and other particulates in collected samples. As such, the collector 20 may be designed to collect and deposit particulates generally within the size range of approximately 1 μm to 10 μm on the sample substrate 24.

Depending upon the sample substrate 24 and/or specific sampling requirements, a substrate coverage density of approximately 5% to 50%, and preferably between 10%-25%, may provide a suitable density of particulate collection for subsequent optical interrogation. Further, depending upon the specific application, alternative technologies may be used to collect and deposit samples on the sample substrate 24, including for example, electrostatic precipitation and cyclone devices.

Referring back to FIG. 1, after the collection station 14 has collected a suitable sample, the sample substrate 24 is relocated to the optical interrogation station 16, which interrogates the sample using one or more devices as will be explained in greater detail herein. The results of the interrogation are coupled to a system controller 60, which includes data analysis algorithms 62 that analyze the interrogation results to determine whether biological or chemical particulates of interest are present in the sample area. The system controller 60 may also execute one or more appropriate action events based upon the analysis of the interrogation results. For example, the controller 60 may sound an alarm or otherwise communicate an appropriate signal if biological or chemical particulates of interest are identified in the sample. The system controller 60 may also write or otherwise store logs, records or other indications with regard to the interrogation results and perform other necessary control functions.

Optical Interrogation Station

The optical interrogation station 16 is responsible for interrogating the sample to determine whether biological or chemical particulates of interest are present in the sample. When analyzing a sample collected on the sample substrate 24, there may be background interference and noise that the data analysis algorithms 62 must discriminate and filter out. This is due, at least in part, because the sample area on the sample substrate 24 may be as large as 1-2 millimeters in diameter. However, a biological or chemical particulate of interest may range from approximately 1 µm to approximately 10 µm. Thus, it is likely that particulates that are not of interest, e.g., dust, are also present in the sample area.

According to one aspect of the present invention, a first optical device is used to determine specific target locations of interest within the sample area. A second optical device is utilized to interrogate the sample area at the specifically determined target locations. The interrogation data from the second optical device is used to identify biological or chemical particulates within the specific targeted locations of interest. This approach may increase the efficiency of sample interrogation by using particulate targeting to reduce the amount of time spent analyzing, filtering or otherwise processing non-biological particulates. Additionally, the first optical device can be utilized to identify one or more fields of view. As used herein, a field of view can comprise the sample area or a subset thereof. Under this arrangement, the field of view may be moved about the sample area to identify target locations or candidate target locations. This allows the data analysis algorithms 62 to look at multiple areas within the sample and determine the best target locations there from.

Figure 4:
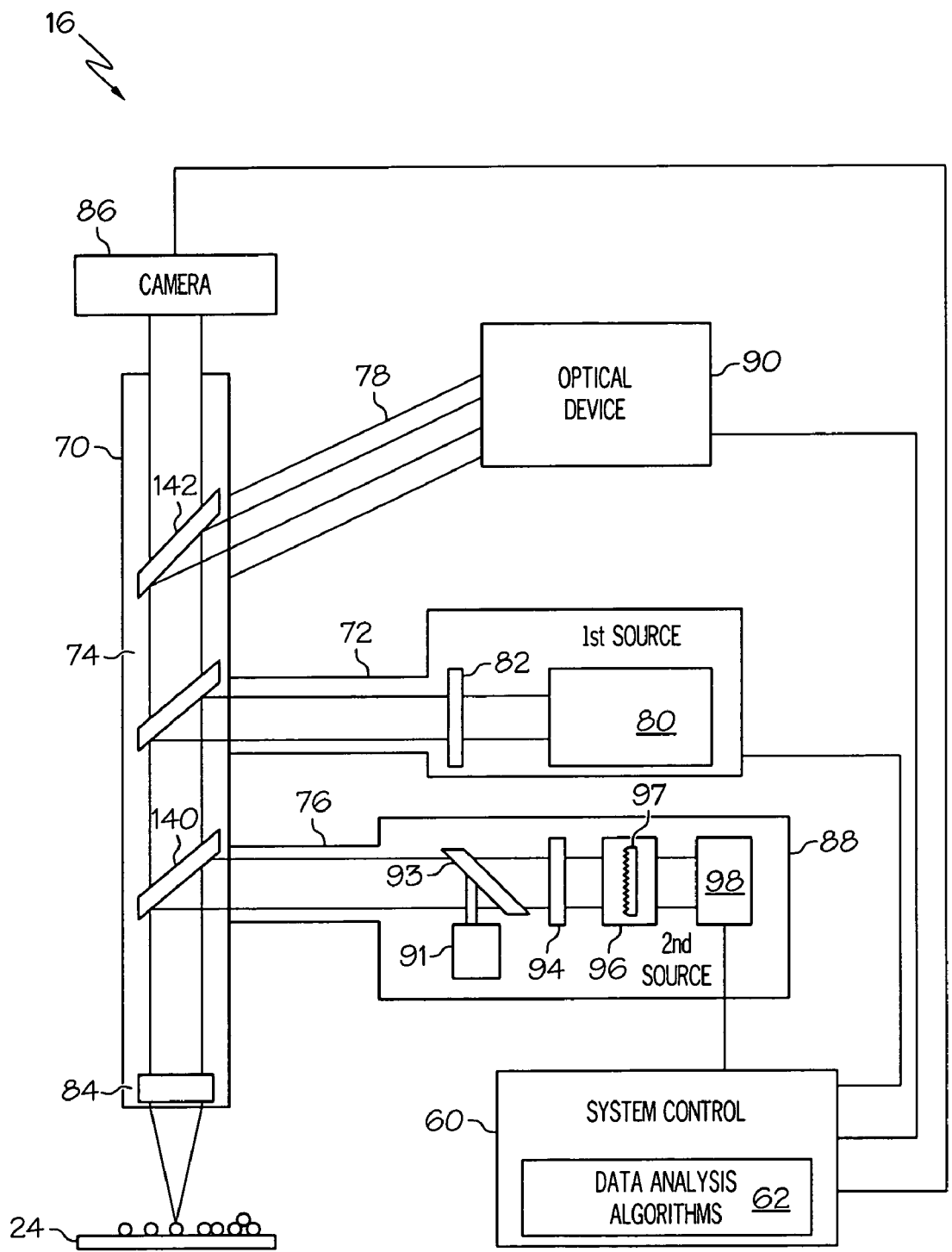
FIG. 4 is a schematic illustration of an exemplary optical system which may be used with the biological and chemical detection system of FIG. 1.

With reference to FIG. 4, the illustrated optical interrogation station 16 comprises an optical system 70 having a first optical path 72, a second optical path 74, a third optical path 76 and a fourth optical path 78. An exemplary first optical device includes a first illumination source 80, e.g., a Xenon arc source, which directs a first light beam along the first optical path 72 through any appropriate lenses, filters or other optical elements 82 to the second optical path 74. The second optical path 74 directs the first beam in a first direction through an objective lens 84 and any other appropriate filters, lenses and other optical elements towards the sample on the sample substrate 24, which has been advanced to a sample substrate receiving area that is generally in register with the second optical path. Light from the surface of sample 24 is reflected and is focused onto a camera 86 to form an image of the sample. This image comprises first data that is processed, e.g., by the controller 60, and which may be used to determine one or more target locations and/or fields of view, which may be of interest for further interrogation, e.g., using techniques such as detecting fluorescence, bright field image processing or dark field image processing as will be described in greater detail herein.

Further, a second optical device provides a second beam, such as from a suitable laser source, which propagates in a first direction along the third optical path 76 to the second optical path 74 where it is focused by objective lens 84 onto the sample substrate 24, e.g., at specific locations determined by the system controller 60 based upon an analysis of the first data. The second beam is reflected from the sample and travels back in a second direction along the second optical path 74 to the third optical path 76, where the second beam is directed to a spectrometer 88, such as a Raman spectrometer.

The interrogation data from the second optical device, e.g., a targeted vibrational analysis produced by Raman spectroscopy, is used to identify biological or chemical particulates within the specific targeted locations of interest. Raman analysis may be used, for example, to distinguish particles of various inorganic compositions from organic particles, and particles of mixed organic/inorganic composition are identifiable as such by their spectra. Fine differences in Raman spectral features may also be detected to distinguish closely similar inorganic species, such as sulfate salts.

Although the second optical device is illustrated and described herein with reference to a laser beam and a corresponding Raman spectrometer 88, other suitable devices, may alternatively be implemented to interrogate a targeted section of the sample, depending upon the sampling and interrogation requirements of a particular application.

The fourth optical path 78 is optional and may be provided for example, to direct reflected light from the sample substrate 24 to an optical device 90, such as a binocular microscope viewer, a second camera or other optical arrangement. A suitable microscope may comprise, for example, an Olympus BX51 by Olympus America Inc., of Melville, N.Y. The first, second, third and fourth optical paths 72, 74, 76 and 78 may each include additional necessary optical elements such as lenses, filters, beam splitters, mirrors and other necessary components to direct, focus and condition the beams. For example, a mirror or dichroic element may be utilized to direct a light beam for fluorescence and other forms of targeting analysis as will be described in greater detail herein.

Figure 5:
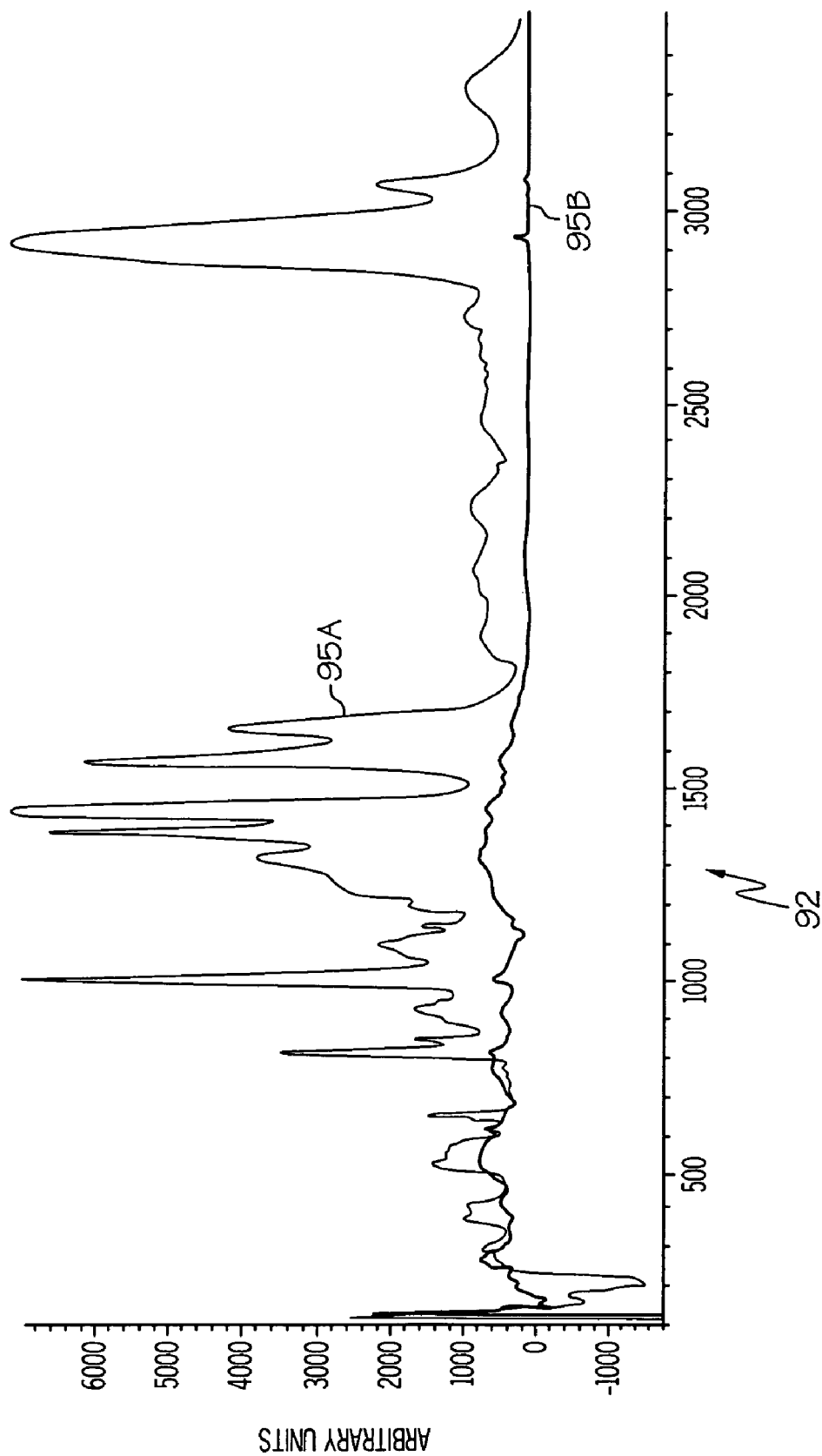
FIG. 5 is an exemplary graph of vibrational modes of molecules analyzed using Raman spectroscopy.

The data analysis algorithms 62 executed by the system controller 60 may be configured to detect and identify biological or chemical threat agents that can be inhaled, e.g., which fall in the range of 1 µm to 10 µm in diameter. Such biological or chemical threat agents are comprised of a complex array of molecules made up of 10-100 billion atoms. In Raman spectroscopy, light interacting with a molecule is scattered inelastically resulting in a slight increase or decrease in the energy of the scattered light. The change in photon energy upon interaction with a molecule results in either a slight loss of photon energy (Stokes radiation) or a slight gain in photon energy (anti-Stokes radiation). Both Stokes and anti-Stokes radiation may be viewed with the spectrometer 88 and corresponds to changes in the molecular vibrations of the particulate(s) and/or background in the targeted sample location interacting with the light. With reference to FIG. 5, an exemplary intensity plot 92 illustrates that the vibrational modes of molecules within an interrogation area can be measured using Raman spectroscopy. Those measurements can be characterized as a "fingerprint" of the molecular constituents in the interrogation area, and the fingerprint may be used, e.g., by the data analysis algorithms 62, for the identification of biological or chemical particulates of interest by using statistical analysis of the measured vibrational modes from the sample.

Figure 34:
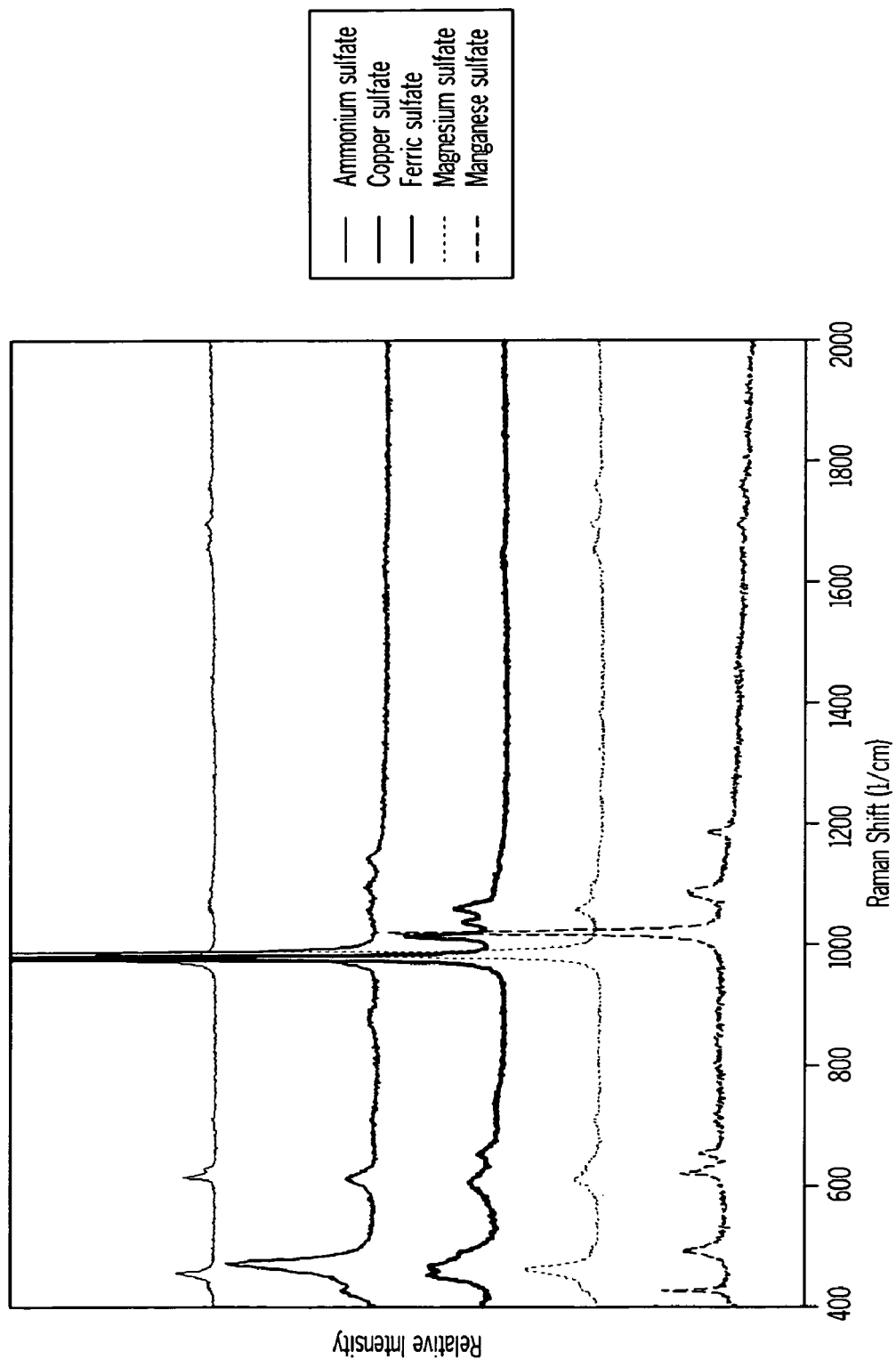
FIG. 34 is a plot of the Raman spectral signatures of for Ammonium sulfate, copper sulfate, Ferric sulfate, Magnesium sulfate and Manganese sulfate.

Referring to FIG. 34, a chart shows the Raman spectra (relative intensity versus Raman shift in cm−1) of particles of several characterized inorganic salts. These spectra show a number of strong features that are common to each trace (e.g., ~450 cm−1, 600 cm−1, 1,000 cm−1) which are attributable to the common anion (SO42−), with smaller satellite features that differ from trace to trace and are attributable to the respective metal cations. Differences in the main spectral features (the largest differences are observed for Fe2(SO4)3 and MnSO4), demonstrate that this technique can be used to distinguish these compounds.

The specific techniques used by the data analysis algorithms 62 may vary depending, for example, upon the biological or chemical particulates to be distinguished from background matter and the nature of the interrogation data collected from the spectrometer 88. However, an exemplary data processing technique that may be implemented comprises distinguishing "fingerprints" of particulates from the interrogation data using a classifier system including a multi-target classification methodology. The classifier may include a limited number of particulates in the corresponding classifier library, e.g., where only specific particulates are of interest or where speed of interrogation is necessary.

While a minimal library may provide certain speed efficiencies, a comprehensive spectral library may enable the unambiguous identification of specific chemical constituents in single particles, whether the particles are homogeneous or of mixed composition. Such a spectral library may include common constituents of airborne particles including for example, carbonaceous species, nitrate compounds, and ammonium-containing compounds. Moreover, a spectral library of common constituents of ambient particulate matter may be developed by supplying samples of neat chemicals to the optical interrogation station 16, which analyzes individual particles to construct the library fingerprints. Such library development may be carried out using a number of diverse source emissions.

The controller 60 may attempt to identify all library targets for each targeted interrogation location. As such, where speed is critical, the number of targeted sample locations may be balanced with the number of library targets. For example, an application may determine to target ten or less particulates of interest for a given sample. However, the classifier system may further include processes for adding additional targets to the detection system. Moreover, the classifier may include a background library, e.g., to identify noise and other particulates that are not of interest in the current data analysis. Such a background library may further be scalable and customizable. For example, an initial interrogation may accommodate new background particulates into a background library. The use of a background library may be beneficial, for example in distinguishing non-agent particulates of interest that happen to fall within a respirable size range, such as dust. The particular approach for discriminating non-agents of interest however, can vary depending upon the class of agent to be detected.

Further, the data analysis algorithms 62 may implement data processing techniques including analyzing spectral regions of interest, performing multi-variant analysis such as by using partial least squares, performing discriminant analysis, utilizing artificial neural networks, employing confidence intervals and by considering likelihood of false positives and false negatives. The data analysis algorithms 62 may also be able to characterize particles with mixed compositions based upon the data derived from the optical interrogation station 16. Thus, the data analysis algorithms 62 may study sources and aging of particulate matter. This technique could be used to monitor the evolution of particle composition within an air mass over time, e.g., by performing trend analysis based upon the results from processing multiple samples, e.g., to determine the rate of threat buildup.

Thus, an adjustable alarm threshold may be established based upon a statistical analysis of the spots from a sample area or multiple sample areas. Still further, trend analysis may be utilized to target specific size, shape, fluorescence or other characteristics based upon changes from previous samples. Accordingly, trends that vary by a predetermined percentage, e.g., 10% or more, may trigger a rule that affects the manner in which fields of view and/or specific target locations are selected for subsequent interrogation and/or may trigger predetermined action events, e.g., provide notice of the change in trend via a suitable communications means. Still further, the system controller 60 may log, store and otherwise record historical information concerning the results of sample analysis.

As an alternative to fluorescence and other contrast based forms of analysis, the first optical device may use spectral "fingerprints" to classify, identify and/or distinguish sample regions or specific particulates within sample regions for additional targeted interrogation. Selective spectral regions may contain strong scattering features that are indicative of a class of particles. In this way spectral regions can be used in a manner similar to fluorescence emission (described in greater detail herein) as a discrimination tool for biological materials. By quickly scanning a select region of the sample, the particulate(s) within the scanned region can be classified and the classification results can be utilized by the system to decide whether to further interrogate the scanned region of the sample, or to continue on to another region for classification.

According to one aspect of the present invention, the efficiency of the particulate interrogation selection is increased by spectral targeting of biological materials. An algorithm is utilized to target specific particulates or sample regions as possible interrogation candidates, e.g., based upon the spectral content of scanned regions of the sample. From that targeting algorithm, the top particles are identified as possible candidates. The field of view is interrogated using the spectrometer 88 or an optical filter and corresponding camera, e.g., a CCD, for a small amount of time, such as 1 second. During that small interrogation time, the spectrometer or optical filter looks at one or more suitable bands, for example, at the C-H stretching region located between approximately 2700 and 3100 $cm^{-1}$, the C-H deformation bands, e.g., between approximately 1390 $cm^{-1}$ and 1500 $cm^{-1}$, and/or the Amide I bands, e.g., between approximately 1590 cm−1 and 1750 $cm^{-1}$.

In FIG. 5, the line 95A represents a curve for a biological stimulant that has been analyzed by a Raman spectrometer. The spectral targeting enhancement is performed by focusing the energy of the peak, which may be located, for example, between 2700 and 3100 $cm^{-1}$. This peak is very strong for biological materials. In comparison, the line 95B illustrates a curve for a non-biological material. The spectral targeting enhancement illustrates that a peak between 2700 and 3100 $cm^{-1}$ is substantially non-existent for non-biological materials. Therefore, after a quick scan of a particle using this technique will determine if further interrogation is necessary. The above example is based upon an assumption that biological particles are of interest. Depending upon the particular sampling requirements, other spectral regions may be scanned or other techniques may be utilized for targeting, additional examples of which are described in greater detail herein.

Referring back to FIG. 4, the spectrometer 88 may be implemented using a second illumination source 91, e.g., a laser that is coupled to the third optical path 76 with a coupling element 93. Light from the sample substrate 24 is directed back along the third optical path 76 and is conditioned through one or more optical devices 94, filtered using a spectrograph 96 and is impinged upon a detector 98. The output of the detector 98 defines interrogation data that is communicably coupled to the system controller 60, and in particular, to the appropriate data analysis algorithms 62 executed by the system controller 60. Other optics may further be provided as the application dictates. For example, a laser line cutoff filter may be provided as part of the laser optical elements 94 to remove any unwanted laser lines and sidebands before the beam passes into the spectrograph 96.

The illumination source 91 emits a beam that targets a specific location on the sample area based upon coordinates determined from an analysis of the data captured as a result of targeting by the first optical device or other suitable device utilized to target particulates or regions of interest within the sample 24. For example, if the first optical device comprises a fluorescent source, the corresponding image captured by the camera 86 may be fed back to the controller 60. The controller 60 analyzes the image from the camera to identify corresponding coordinates for further field(s) of view and/or to identify specific target locations, e.g., locations of particulates of interest.

The beam may target the sample area at a resolution of approximately 1-2 microns in diameter or less. Thus, a single particulate may be isolated for interrogation. Moreover, positioning of the beam within the sample area may be implemented using any number of techniques, such as by use of a motorized stage having a high degree of accuracy, e.g., to a resolution of 0.1 microns. Moreover, the data analysis algorithms 62, e.g., the targeting algorithms that compute the address or location of the specific target locations, in cooperation with the resolution of the motorized stage, may obtain a target data that places the beam to within approximately one micron of the target particulate of interest.

Several factors may be considered in order to establish an efficient detection and identification system using a Raman-based spectrometer 88. For example, a high signal to noise spectra may be achieved by optimizing the second illumination source 91 including optimizing the laser power, stability and wavelength, as well as by selecting the proper size spectrograph 96, selecting an appropriate detector 98 and calibration settings for the spectrometer. Further, the sample substrate 24 should be designed to be compatible with Raman interrogation and the microscope magnification and focal length should be configured, e.g., by properly selecting and positioning the objective lens 84, and by targeting particulates of interest on the sample substrate 24. In this regard, the optimal choice of the objective lens 84 may provide the best combination of selective targeting of the feature of interest and averaging of the largest representative area.

In one exemplary implementation, the second illumination source 91 comprises a 633 nm (red) Helium Neon (HeNe) laser that output 17 milliwatts at the source and 7 milliwatts focused. The beam passes through a 100× objective lens 84 to realize approximately a 1.5 micron spot size on the sample substrate 24. The system may further provide an automated neutral density filter control of power in the range of $10^{-4}$ to 100%. The spectrograph 96 may capture on the order of approximately 500 to 1800 $cm^{-1}$ without movement of an internal grating 97 at a resolution of less than 2 $cm^{-1}$/pixel and the blaze of the internal grating 97 may be between approximately 580 nm and 720 nm. Still further, the spectrometer 88 may operate in a range from approximately 2 cm-1 to 12 $cm^{-1}$, and preferably between 3 $cm^{-1}$ and 8 $cm^{-1}$, and may have an automated control of the slit width and/or a throughput on the order of approximately 30% or greater.

The grating 97 of the Raman spectrograph 96, and in particular, the number of grooves per millimeter, determines the spread of the wavelength range of the measured spectrum. Generally, more grooves provide a wider separation. The grating 97 may provide a large enough area for static grating placement, e.g., 1,200 grooves per millimeter in applications where scanned grating implementations are too time consuming.

Typically, the Raman spectrometer will have a diffraction grating that disperses the different wavelengths across a set of adjacent rows of pixels on a multichannel optical detector 98. Alternatively, to obtain enhanced sensitivity to biological materials, a modified diffraction grating can be used to disperse different wavelengths on different regions (rows) of the multi-channel device. The modified dispersion allows enhanced detection of specific wavelengths.

The detector 98 may comprise for example, a 1024 channel detector that is Peltier cooled at least to −70 degrees Celsius. The detector 98 should exhibit a read out and dark current noise level suitably low such that noise is dominated by the shot noise of the light emitted by the sample on the sample substrate 24 and not the detector contributions. However, other detector arrangements may be implemented, including other multi-channel configurations. Also, the cool down time of the detector 98 may be rate limiting to the system. As such, the cool down time of the detector may be considered based upon the specific application requirements. One exemplary detector comprises a 1024×256 pixel array that is air cooled and has a quantum efficiency greater than 50%. The exemplary detector further comprises a read out noise less than 5 electrons per pixel and a dark current draw of less than 0.004 electrons/pixel/sec.

According to an aspect of the present invention, multiple holographic gratings are superimposed on top of each other to allow diffraction to occur at different spectral regions so that different levels of diffraction can occur. For example, two grating profiles in a HoloPlex™ (Kaiser Optical Systems, Inc.,) grating are provided so as to have different diffraction ranges. This allows more custom options on a holographic grating. As such, the system may be able to look in detail at one region of the diffracted spectrum while the entire diffracted range could be viewed on the other hologram. For example, a first grating may spread the spectrum across the detector from 0-2000 $cm^{-1}$. Instead of the second grating covering 2000-4000 cm $cm^{-1m}$, the diffracted light range of the second grating may be much smaller, e.g., 2700-3100 $cm^{-1}$ thus resolving more line shape and detail from the spectrum.

The focal length of the spectrograph 96 affects the resolution of the instrument. An exemplary focal length may be implemented in the range of approximately 250 millimeters to approximately 300 millimeters. In addition, spectral calibration may be periodically required. Depending upon the specific implementation, physically integrated calibration diodes and other calibration tools may be provided to calibrate the wavelength as will be described in greater detail below.

Figure 33:
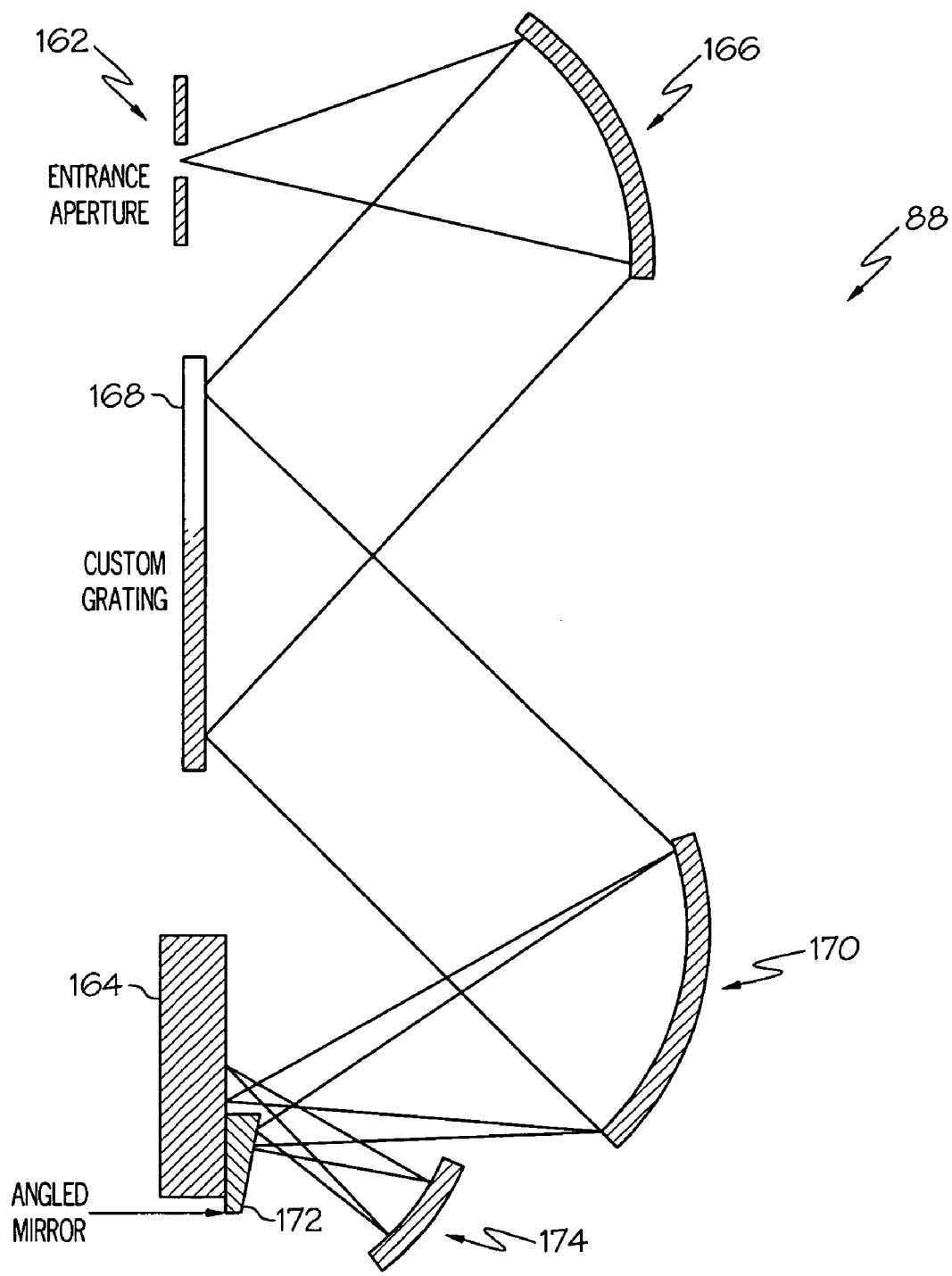
FIG. 33 is a schematic diagram of an exemplary spectrograph according to an aspect of the present invention.

The standard Czerny-Turner implementation in the spectrograph 88 contains an entrance aperture, two curved mirrors, a grating and a CCD. However, this architecture may provide unsatisfactory detection signals, depending upon the particular sampling requirements. Referring to FIG. 33, an alternative arrangement is illustrated. The system shown in FIG. 33 may implement the function of the grating 97 shown in FIG. 4. by way of example, assume that a 1:1 imaging spectrograph 88 with a focal length of 300 mm is to be utilized. The light to be analyzed enters the spectrograph 88 through the entrance aperture 162, such as a slit. To optimize the resolution of the spectrograph 88 with respect to a corresponding detector 164, e.g., a CCD, the entrance aperture 162 may be only as wide as the pixel size on the detector 164. The height of the entrance aperture 162 may be less than or equal to half the height of a pixel of the detector 164. The light that enters the entrance aperture 162 strikes a first curved mirror 166, e.g., a mirror having an f# of 4, to be collimated and projected onto a grating 168. The grating 168 will angularly separate the light by wavelength. The light from the grating 168 is then collected by a second curved mirror 170 and is directed onto the detector 164 image plane as a line.

Keeping with the current example, assume that a grating 168 is chosen such that the light that hits the detector will be of the range of 0 to 2000 $cm^{-1}$. The grating 168 separates not only the 0 to 2000 $cm^{-1}$ light but also beyond that range. Unfortunately this light then continues on a line past the image plane of the detector 164. According to one aspect of the present invention, the range of the spectrometer 88 is extended by collecting that "lost" light. An angled mirror 172 is mounted, e.g., to a metal surface of the detector 164. The alignment of the angled mirror 172 is generally not critical. The angled mirror 172 reflects light that would normally just hit the front of the detector 164 and directs it to a third curved mirror 174. The third curved mirror 174 then images the reflected light back onto the detector 164 but at a different position on the detector 164 than the corresponding light from the second curved mirror 170.

Because the grating 168 is not designed to cleanly separate the light that extends beyond the image plane of the detector 164, the spectrometer 88 may experience effects of higher orders from the grating 168. This will show up as a duplicate of the first order but at a lower intensity. However, such effects may be low enough for most applications to have negligible effect. If low light levels are required by a particular application, then those higher order photons can be calculated out by using the initial light on the first row of the detector 164 as that row has no other interfering higher orders from the grating 168.

The spectrometer 88 may be focused so as to interrogate the sample on the sample substrate 24 in a range of interrogation areas from approximately 1 millimeter in diameter, e.g., to analyze an average overall sample area, down to approximately 1 to 2 microns in diameter, which is focused enough to target a single particulate of interest in the illustrative example of detecting respirable particulates. In this regard, the system controller 60 may include software for controlling, commanding or otherwise affecting the positioning of filters within the optical interrogation station 16, controlling ultraviolet shutter actuation, capturing of image and image processing, pinpointing location of targets within the sample area and passing the coordinates to a Raman acquisition program, e.g., to control the motorized stage or to control other suitable targeting arrangements so as to suitably align the targeted particulates on the sample with the interrogation device, e.g., the spectrometer 88.

Figure 6:
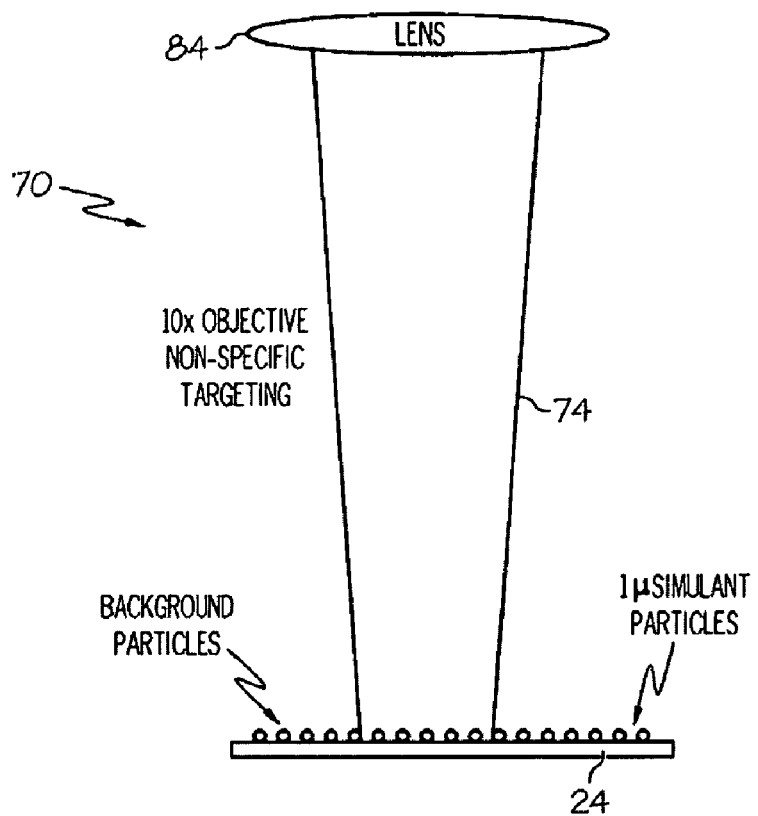
FIG. 6 is an illustration of the optical system of FIG. 4 performing a non-specific field of view interrogation of a sample area.

Referring to FIG. 6, in a first illustrative example, the objective lens 84 in the second optical path 74 of device 70 comprises a 10× magnification and is used in a non-specific targeting application to focus the beam so as to interrogate the sample on the sample substrate 24 in a relatively large interrogation area. As schematically illustrated, multiple particulates, which may include background particulates as well as biological or chemical particulates of interest, are measured. As such, the data analysis algorithms 62 executed by the system controller 60 may be required to filter out the background particulate information in order to perform detection and identification of biological or chemical particulates of interest.

Figure 7:
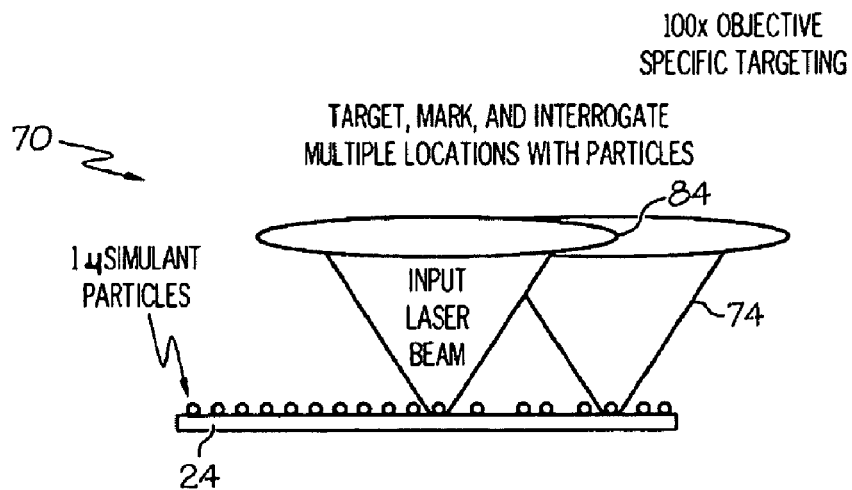
FIG. 7 is an illustration of the optical system of FIG. 4 performing a target interrogation of a sample area.

Referring to FIG. 7, in a second illustrative example, the objective lens 84 in the second optical path 74 of device 70 comprises a 100× magnification and is utilized in a targeted application to focus the beam in a relatively small interrogation area. As schematically illustrated, the use of the 100× objective lens 84 allows the optical interrogation station 16 to target, pinpoint and interrogate a single particulate on the sample substrate 24. Moreover, the field of view can be moved about the sample area on the sample substrate 24 such that the optical interrogation station 16 can individually target and interrogate multiple target locations of interest. In this regard, a field of view may also be moved about to identify candidate sample regions as noted in greater detail herein. In practice, the particular magnification of the objective required to interrogate a single particulate and/or a specific area within a field of view may vary depending upon the implementation of the interrogation station 16 and the size range of particulates being analyzed.

The ability to target a single particulate may allow a relatively simple classification implementation to particulate identification. For example, libraries can be constructed using training sets that characterize biological or chemical particulates of interest without background, or with known constituents and properties. Thus, feature extraction and classification algorithms have less noise and background interference to discriminate against and the targeted Raman spectrum may contain a fingerprint of a particulate of interest that can be compared to fingerprints in the classifier library in a relatively efficient manner. Moreover, when automating the movement of the laser beam for spectrographic analysis to target particulates of interest, multiple spectra are collected from relatively higher probability particulates based upon coordinates determined by the targeting algorithm executed by data analysis algorithms 62. The data analysis algorithm 62 may also be operable to balance a signal to noise ratio against replicate particulates of interest based upon spectral collection time, integration time and other factors.

Figure 8:
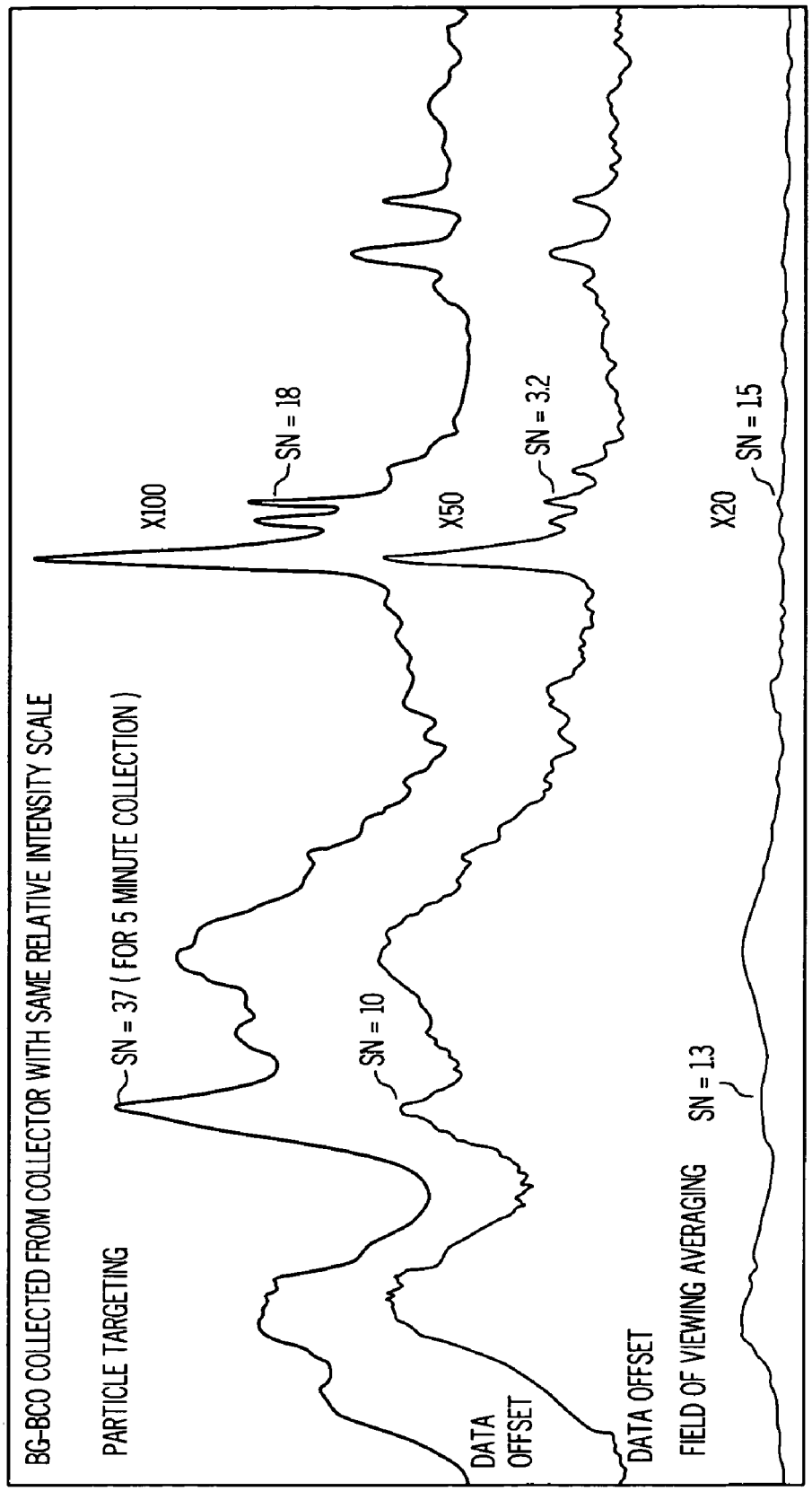
FIG. 8 is a chart illustrating exemplary signal to noise measurements for a sample at three different interrogation objective magnifications.

Referring to FIG. 8, an exemplary chart illustrates the effect that the objective lens magnification power has on the signal noise ratio when detecting biological or chemical particulates of interest on the sample substrate 24. The chart illustrates a sample measured using three magnification factors including a magnification factor of ×20, ×50 and ×100. The chart demonstrates that the ×100 magnification objective consistently realizes a larger signal to noise ratio compared to relatively lower ×20 and ×50 objective magnifications.

As noted in greater detail above, once the targeted locations within the sample have been identified, specific interrogation within those fields of view may be carried out. However, current dispersive Raman spectrometers require a mechanical action to occur in order to either pass the Raman laser to the sample or to view the image of the sample. According to an aspect of the present invention, a system is provided wherein the sample may be viewed simultaneous with viewing the laser on the sample with no mechanical action. Moreover, the point of interrogation by a laser can be projected onto the visible image of the sample so that the precise location of the interrogation spot can be visualized. This allows more accurate correlation of targeting and interrogation spot.

Referring back to FIG. 4, instead of a mirror that is slid into place for Raman laser injection, a fixed dichroic mirror 140 is used instead. The dichroic mirror 140 is chosen such that frequencies at or above the laser line are reflected to the spectrometer 88 while frequencies below the laser line will transmit through the mirror 140 to the imaging camera 86. Alternatively, the dichroic mirror 140 may be configured to reflect frequencies below the laser line and to transmit frequencies at the laser line and above. This option may provide greater flexibility in designing the dichroic mirror 140, e.g., where it is desirable to pass ultraviolet (UV) light to the imaging camera 86 because passing UV through a dichroic mirror 140 may be difficult to design due to most materials that absorb UV light. This option may further require that the physical positioning of the camera 86 and spectrometer 88 be swapped, or that an alternative configuration of the camera 86 relative to the spectrometer be provided.

Figure 9:
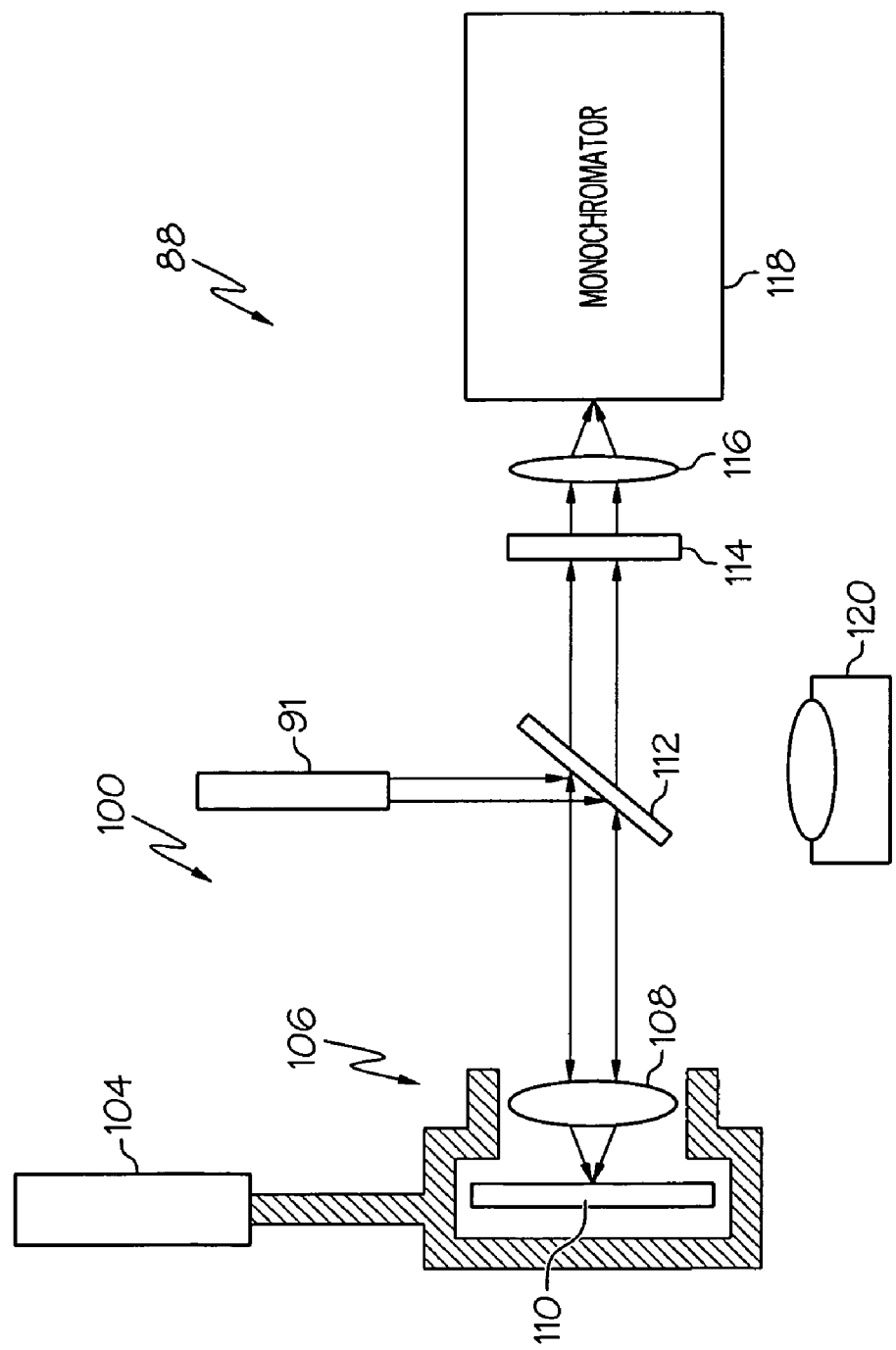
FIG. 9 is a schematic illustration of a system for calibrating a spectrometer of the optical system of FIG. 4, wherein an actuator of the system is in a first position.

Referring to FIG. 9, the spectrometer 88, e.g., when implemented as a Raman spectrometer, also periodically requires two different calibration processes in order to properly calibrate the exact wavelength of the light hitting the detector 98. According to one aspect of the present invention, a completely internal calibration system 100 is provided to calibrate the spectrometer 88. During an automated calibration operation, an actuator 104 translates an assembly 106 containing a focusing lens 108 and a calibration substrate having a bead 110 thereon, into an optical path of the laser 91. The bead 110 may comprise, for example, a one-micron particle, such as a polystyrene bead, a silicon bead, a photolithographically prepared film with micron and submicron features or other bead with strong Raman signature, which is mounted and properly indexed on the substrate.

The laser beam is turned on, and a dichroic mirror 112 is utilized to direct the beam towards the assembly 106. The focusing lens 108 collimates and focuses the beam onto the substrate. The light is then directed through a laser line filter 114 and a focusing lens 116 before being directed to the monochromator 118. In this regard, the monochromator 118 implements the function of the grating 97 described herein with reference to FIG. 4. The wavelength of the beam entering the monochromator 118 is measured and is used for calibration.

For example, Raman spectra is taken at a first index position, which may be an almost correct laser position relative to the indexed bead 110. The substrate stage or actuator 104 is then adjusted in two dimensional directions, x and y, in small (e.g., submicron) incremental steps around the first index position and a Raman spectrum is measured at each step. The collected Raman spectra are compared to establish the correct two dimensional index position for optimal laser-particle alignment. For example, the particular bead 110 may have a characteristically strong spectral response at a known wavenumber (cm−1) in the spectrum. By comparing the signal strength of the known wavenumber for each indexed position, the strongest signal can be considered the closest to registration with the bead 110. The system controller 60 then positions the laser 91 to the selected index, and the automatic laser-particle alignment is completed.

Figure 10:
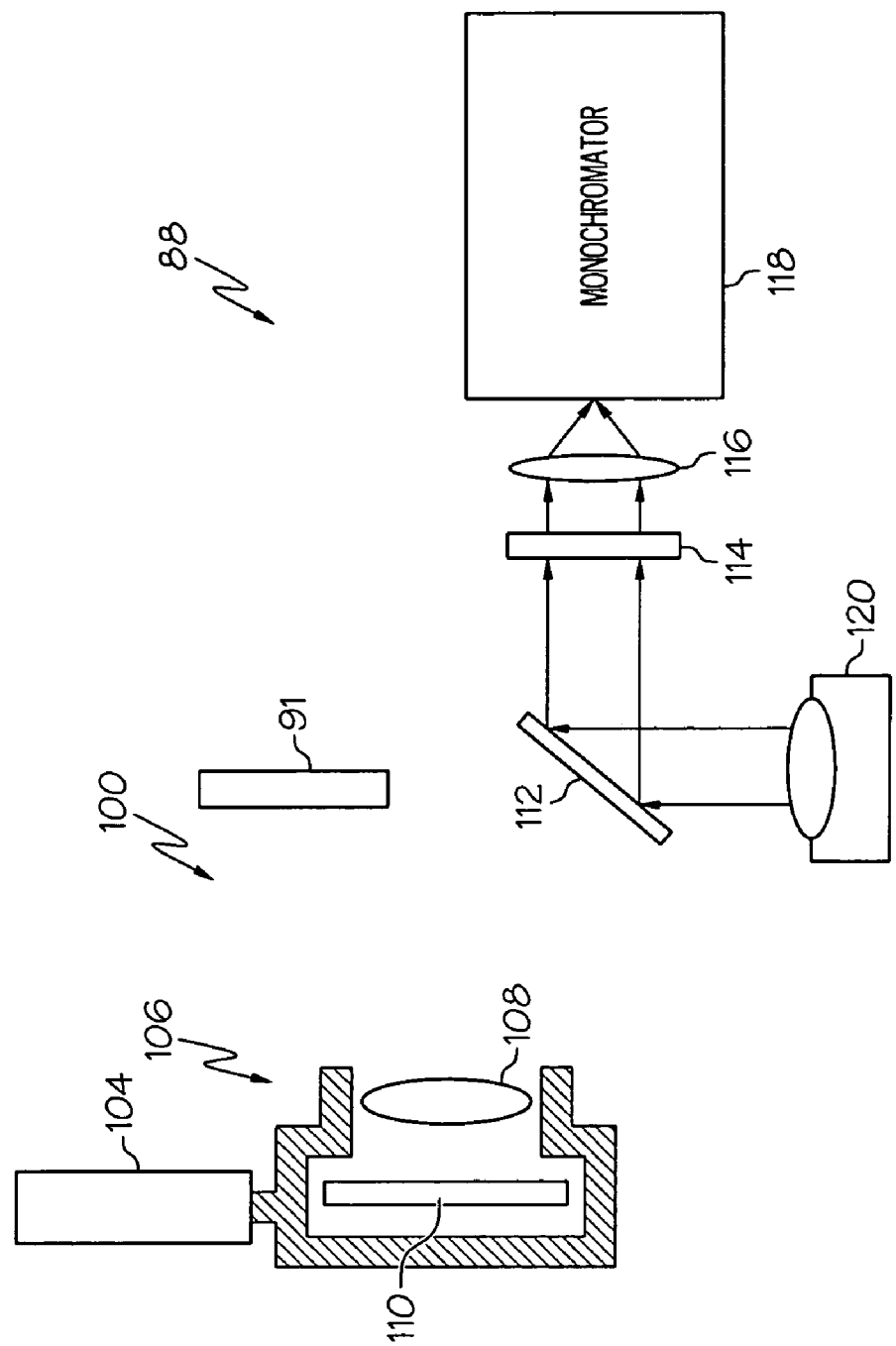
FIG. 10 is a schematic illustration of the system for calibrating the spectrometer of FIG. 8, wherein the actuator is in a second position.

Referring to FIG. 10, the system 100 may also be utilized to calibrate the absolute wavelength of the monochromator 118. When calibrating the absolute wavelength of the monochromator 118, the actuator 104 maintains the assembly 106 in a retracted position compared to its position as shown in FIG. 9. A neon lamp 120 directs a beam towards the dichroic mirror 112, which reflects the beam through the laser line filter 114 and the focusing lens 116 before being directed to the monochromator 118. The light entering the monochromator 118 is measured and is used to calibrate the absolute wavelength of the monochromator.

The automated calibration may be performed, for example, as part of a startup process or before a daily operation of the instrument if running unattended for extended periods of time.

Targeting of Biological or Chemical Particulates of Interest within a Sample Area According to one aspect of the present invention, one or more subsets of the particles within a sample are selected for particle size determination, e.g., by microscopy and Raman particle analysis. Typical analyzing times may be in the range from approximately 10 seconds to approximately 5 minutes, depending on the data needs and desired turnover rate.

Referring briefly back to FIG. 3, it can be seen that the location of particulates formed in the sample may be affected by the particulate size, e.g., particulate size may decrease with the distance within the sample from the center of the nozzle of the collector. This information may be utilized, for example, when selecting target locations based, at least in part, upon particulates of a predetermined size range.

Another exemplary technique comprises the use of images, e.g., from the camera 86 for the selection of specific sizes and/or shapes of target particulates. Typically, biological particles of interest will be in the range of approximately 1 to 10 microns in diameter because this is the range in which particles are most likely to be retained up respiration. Targeting this size range by image processing may thus increase the likelihood of identifying harmful particles contained within the sample. Using corresponding image processing techniques, particles of a specific size range and/or shape can be located in the field of view for interrogation by spectroscopic techniques.

However, the sample area will likely include particulates that fall within the particular determined size range, which are not particulates of interest. Rather, such particulates are noise and should be ignored. Various discrimination techniques, including those identified in greater detail herein may be used for particulate discrimination. The selection of the most appropriate discrimination technique will depend upon the class of the particulate of interest.

As noted in greater detail above, a first optical device is used to determine specific field(s) of view and/or specific target particulates of interest within the sample area. An exemplary first optical device may comprise a fluorescent device. Biological particles fluoresce as much as 10 times or more compared to background materials when appropriately excited by a beam of light. Thus, fluorescent background removal is effective at removing non-fluorescing background particulates such as dust, which may be within a size range of particulates of interest. The optical interrogation station 16 may thus use fluorescence to perform a high contrast analysis of at least a portion of the sample area to specify the location or locations within the sample area that are most likely to contain biological or chemical particulates of interest. The optical interrogation station 16 then uses the results of the fluorescence analysis and/or size determination to pinpoint target locations for further interrogation.

Figure 11:
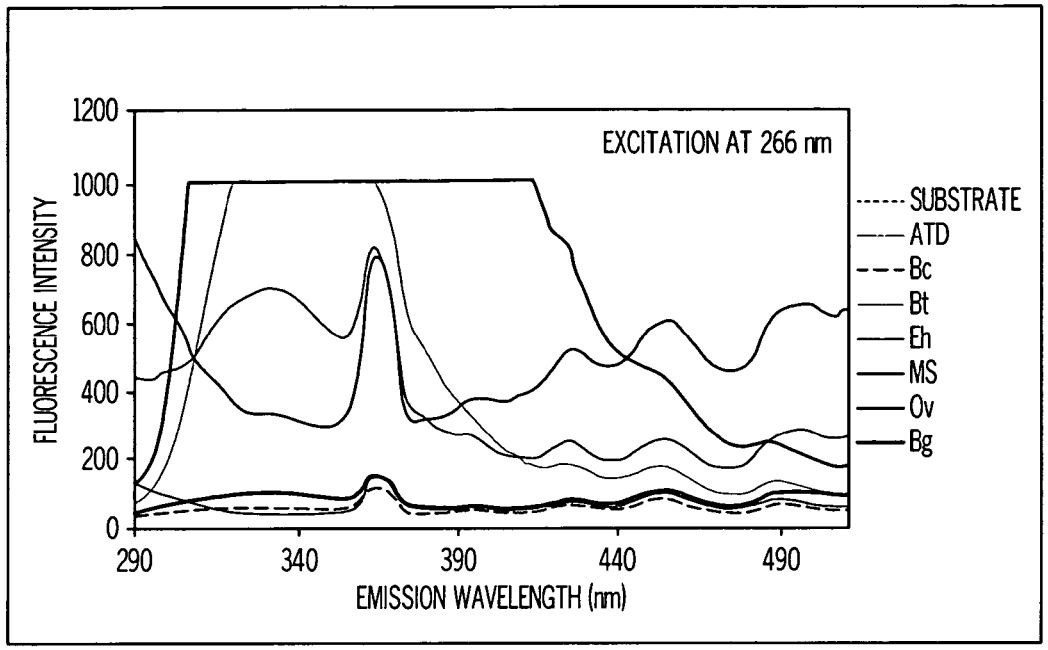
FIG. 11 is an exemplary graph of fluorescence as a function of emission wavelength of a sample excited by a laser having a wavelength of 266 nm.
Figure 12:
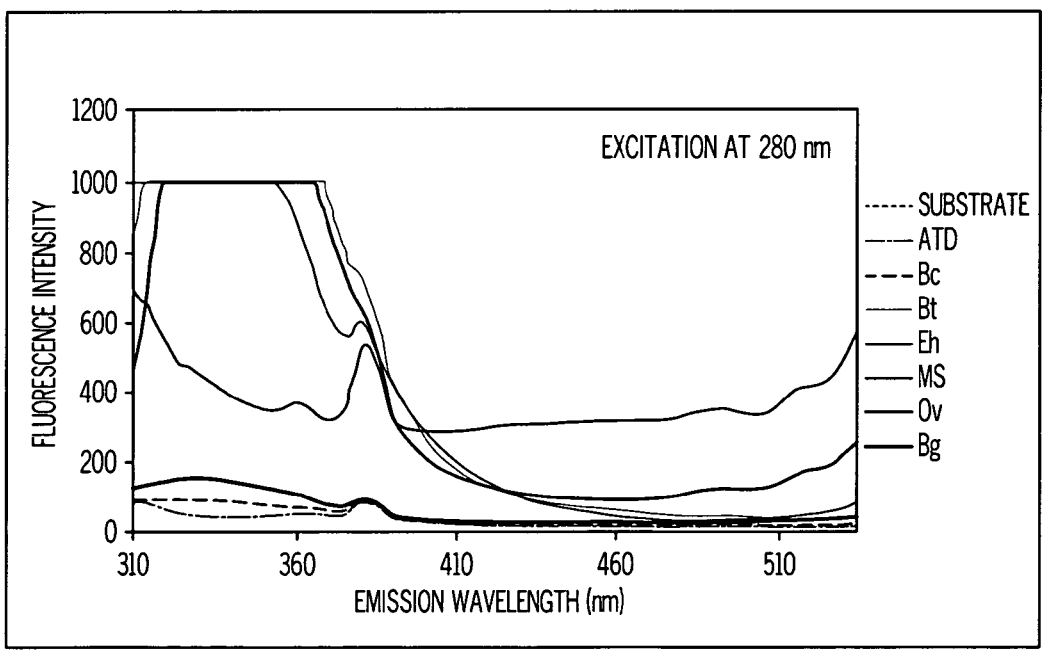
FIG. 12 is an exemplary graph of fluorescence as a function of emission wavelength of a sample excited by a laser having a wavelength of 280 nm.
Figure 13:
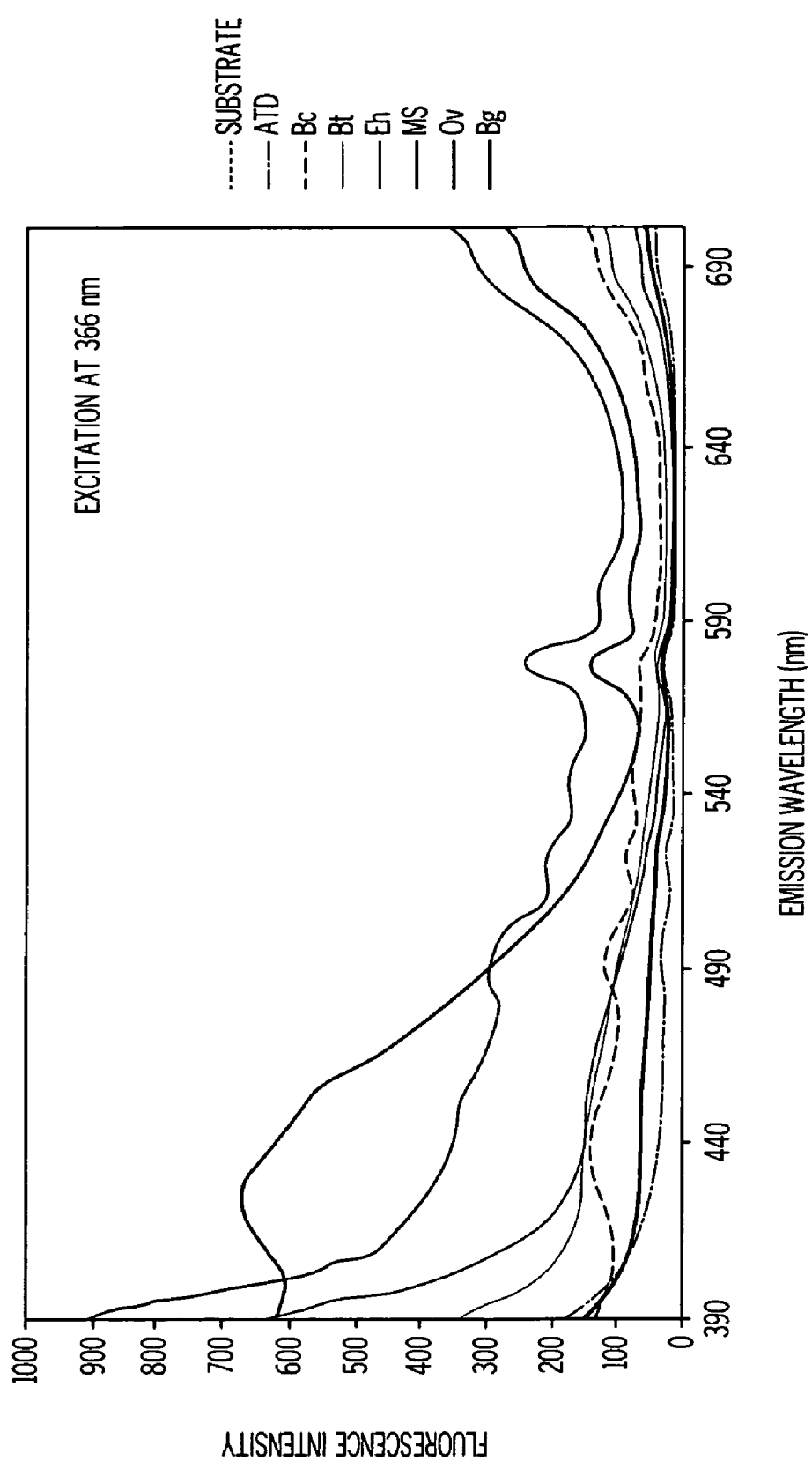
FIG. 13 is an exemplary graph of fluorescence as a function of emission wavelength of a sample excited by a laser having a wavelength of 366 nm.
Figure 14:
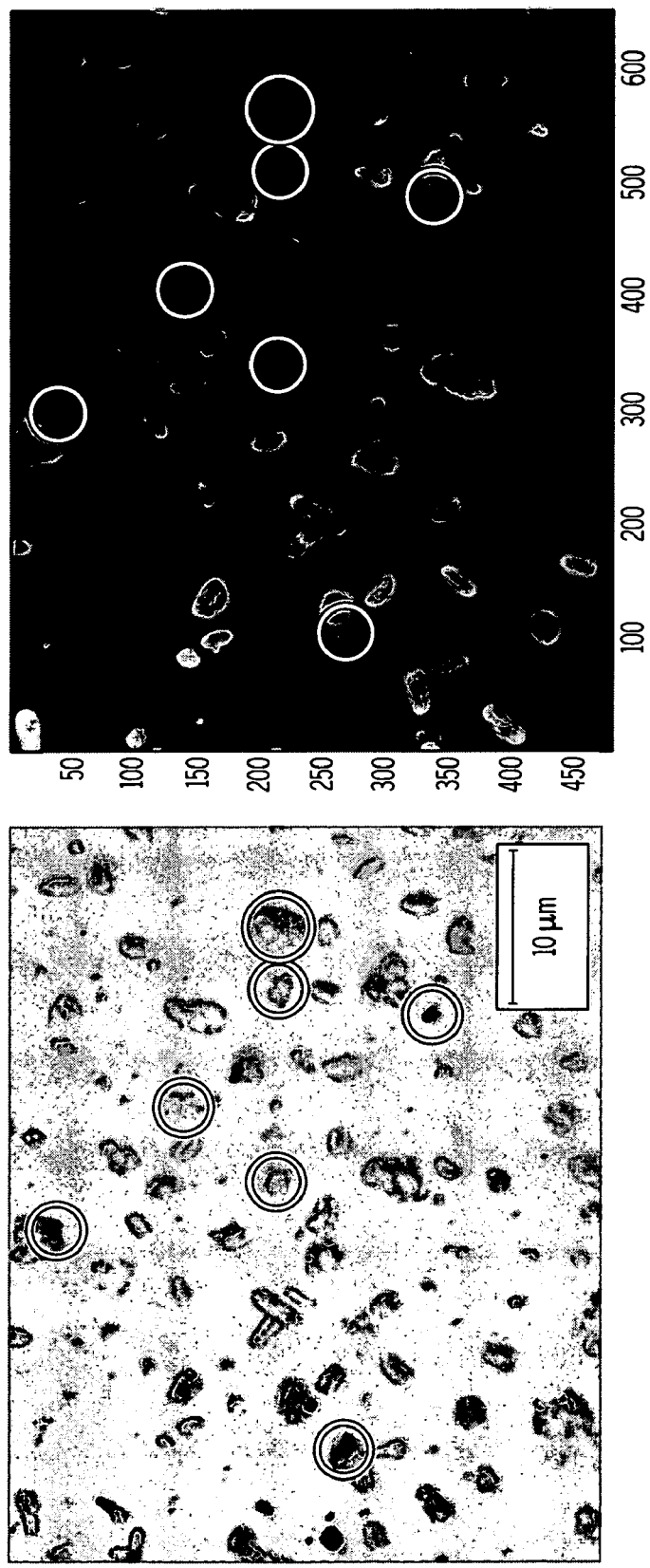
FIG. 14 is a comparison that illustrates a bright field image compared to a fluorescence image for an exemplary sample.

There are often relatively large variations in detected fluorescence for different organic material when excited at different wavelengths. However, deep ultraviolet excitation, e.g., in the 250-300 nm wavelength and ultraviolet emission excitation, e.g., in the 320-400 nm wavelength, may be utilized to adequately target certain biological and chemical particulates. For example, FIGS. 11-13 each illustrate a chart that graphs emission wavelength as a function of fluorescence intensity for several particulates including Arizona test dust (ATD), *Bacillus cereus* (Bc), *Bacillus globigii* (Bg), *Bacillus thuringiensis* (Bt), *Erwinia herbicola* (Eh), Baterial phage (Ms) and Ovalbumin (Ov). FIG. 11 illustrates the above particulates excited by a 266 nm laser beam. FIG. 12 illustrates the above particulates excited by a 280 nm laser beam and FIG. 13 illustrates the above particulates excited by a 366 nm beam. A comparison of FIGS. 11-13 illustrates that the emission wavelength vs. fluorescence intensity curve for each organic material varies based upon the excitation wavelength. As such, data analysis algorithms 62 may look at multiple fluorescence wavelengths when determining specific targeted locations within the sample area for further interrogation.

As noted above, size may be considered in selecting field(s) of view and/or target locations, in addition to the fluorescent data. For example, in a particular field of view, fluorescence data may be used to identify particulates of interest and to eliminate particulates that are not of interest, e.g., particles that do not fluoresce, which may comprise a substantial number of particulates within the field of view. The particulates of interest identified by the fluorescence analysis may be further filtered based upon the size of the corresponding particulates to define candidate particulates, e.g., by including only particulates in a size range of approximately 0.75 microns to approximately 3.5 microns or some other suitable range. Once the particulates are filtered by size, a limited number of particulates may be selected from the candidate particulates for subsequent interrogation, e.g., by ranking the filtered particulates by fluorescent intensity, size, or any other desired factor.

With reference to FIG. 14, a bright field image is compared to a fluorescence image for an exemplary sample, which includes *Bacillus globigii* (Bg), and background particulates commingled with the Bg. Bg is listed by the Center for Disease Control as a “Class 1” organism and is commonly used as a simulant for *Bacillus anthracis*, otherwise known as Anthrax. The image was processed in approximately 11 seconds and reveals that fluorescence can discriminate Bg from background material. To perform targeted Raman analysis of the exemplary sample of FIG. 14, the data analysis algorithm 62 analyzes the fluorescence image to determine one or more of the highest contrast particulates of interest.

The location of the determined high contrast target locations (after optionally also filtering by particulate size) are mapped to coordinate locations which are used to target and focus the second illumination source 91 to interrogate a specific target location (pinpoint a particulate of interest) within the sample area on the sample substrate 24. Specifically, in FIG. 14, the features of the image that appear in the circled areas of the brightfield image do not appear with a high contrast in the fluorescence image. These features were tested and were not identified as Bg. Thus, the fluorescence imaging may allow a higher percentage of features of interest to be determined in certain circumstances compared to a corresponding brightfield counterpart image.

In addition, when continuously monitoring a site for targets, a trend may be established for the size or fluorescence of particles that are typical for that site. Trends may also be used to monitor the evolution of particulate composition within an air mass over time. Further, trend analysis across multiple sample substrates can be used to predict rates of threat buildup and to modify the criteria used to determine the target locations for specific particulate interrogation. For example, some environments may include non-threatening background particulates that fluoresce. However, using trend analysis, fluorescing background can be distinguished from sudden buildups or sudden changes in the distribution of particulate sizes.

Moreover, other imaging techniques may also be used to determine specific fields of view for subsequent interrogation. For example, darkfield microscopy may be used to locate particles of interest for subsequent Raman interrogation. The images of biological particles with a size of 1-10 microns in diameter are mostly transparent to visible radiation. Illumination with visible or ultraviolet light produces a reflection in a brightfield mode that has a light background. Correspondingly, the use of darkfield imaging produces a dark background because of the use of an oblique angle of illumination. The light from particles on the sample substrate 24 that fluoresce are captured, e.g., by the camera 86 to produce a light feature on a dark background.

Using dark field microscopy, individual particles may be detected, even in low light levels. For example, particulates may be identified by locating objects based upon the intensity of the illuminated pixels on the image captured by the camera 86. Algorithms may then be used to connect the location of adjacent pixels into objects that can be analyzed for size, shape, and overall intensity. The higher contrast produced by a dark background may increase the accuracy of the particle's size definition.

Further, additional or alternative combinations of techniques can be used to identify target locations and/or field(s) of view that contain particulates of interest. When a combination of UV and visible wavelength light images are used for targeting of features of interest, the features produced with one wavelength range must be correlated with features produced by another wavelength range. However, the movement of optical components to allow illumination by different wavelengths of light can produce variations in the locations of features in the images produced by these different wavelengths. As an alternative to moving the optical components, the location of microscope optical components may be arranged to reduce the variation in feature location. By selection of the optical response of the components, images may be produced without any optical movements. Thus, for example, the different wavelengths for each image can be directed to different cameras for image detection. This elimination of optical hardware movement improves the mapping of features for different illumination.

Referring again to FIG. 4, according to an aspect of the present invention, the optical device 90 may comprise a second camera. The use of two cameras 86, 90 may be beneficial, for example, in a system where two different image planes needed to be focused due to the focal length of a microscope objective changing with respect to the wavelength of the light. As an alternative to two cameras, the system 16 may comprise a selectable mechanical filter assembly before light reaches the camera 86, which may be focused or otherwise changed to accommodate each or two or more image planes.

As shown, a dichroic element 142 is utilized to split the light into upper and lower spectral bands. These upper and lower bands can then be optionally filtered again for isolation of narrow band regions. Light that is reflected from the sample reaches the dichroic mirror 142 that passes the high band to the camera 86 and reflects the low band to the camera 90, or vice versa. The two cameras 86, 90 thus need not be identical. For example, each of the camera 86 and camera 90 may comprise charge coupled devices (CCD) devices. CCD1, corresponding to the camera 86 may be chosen, for example, to be UV enhanced and CCD2, corresponding to the camera 90 may comprise a normal visible camera. The distance from the dichroic mirror 142 to each camera 86, 90 is chosen such that each total path length from the camera 86, 90 to the focus point is different. This then allows the two cameras 86, 90 to be focused independently. Because the microscope focuses at different distances for different wavelengths, each camera 86, 90 can be individually focused to the same point, which may be accomplished with no moving parts, while also simultaneously imaging two different wavelength regions.

Ultra Violet LED Sample Illumination

Proper illumination of samples under microscopic examination facilitates optimal identification and classification of particles. Often this illumination has specific wavelength characteristics to enhance the identification. For example, proper illumination of the sample on the sample substrate 24 may cause the sample to emit light at a different wavelength then the incident light. The detection of the light at this shifted wavelength is useful in identification as noted in greater detail herein. In this regard, lenses with specific optical configurations may be used to direct a band of wavelengths of light to the sample and a different path may be used to collect the shifted light for detection.

To generate the incident beam, LEDs may be used. The LEDs may form coherent or incoherent ultraviolet to visible light. In one embodiment, LEDs may be formed in an annular array outside of an objective assembly of the objective 84 to illuminate the sample on the sample substrate 24. Alternatively, LEDs may be formed in an annular array inside a darkfield objective assembly to provide illumination that allows darkfield detection of specific sample features of the sample on the sample substrate 24. The inclusion of a light source in combination with the objective 84 may be provided as an alternative to the first optical path 72 and corresponding light source 80 and any appropriate lenses, filters or other optical elements 82.

The UV LEDs which are integrated with the objective may provide a more durable and cost efficient alternative to the light source 80, which may comprise Xenon or Mercury arc lamps that may exhibit a relatively short lifetime and require the use of relatively expensive optical elements 82 such as bandpass filters, dichroic filters, and specially machined mirror reflectors to direct and then filter the light onto the sample surface of the sample substrate 24.

Figure 15:
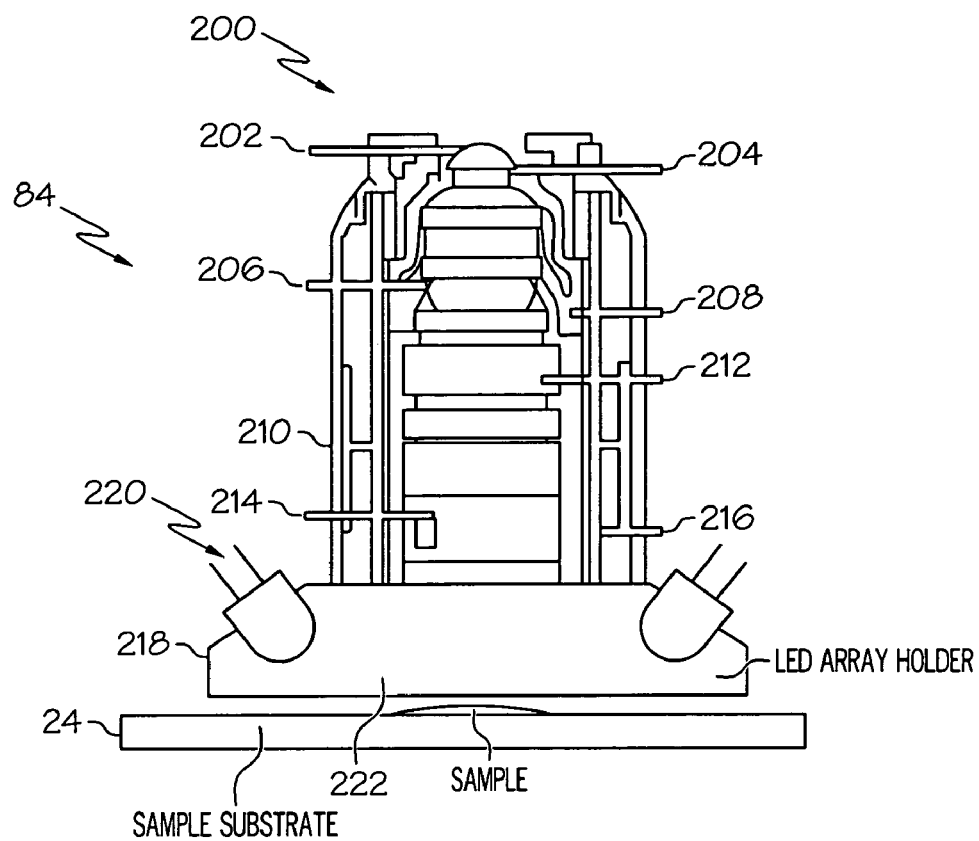
FIG. 15 is a schematic cut out view of an objective assembly according to an embodiment of the present invention.

Referring to FIG. 15, the objective 84 described with reference to FIG. 4 may comprise a modified (bright field) objective assembly 200 that includes an objective assembly rear aperture 202, a rear lens element 204, a lens doublet group 206, one or more lens spacers 208, an objective assembly barrel 210, a lens element 212, a lens triplet group 214, an internal lens housing 216 and a front aperture. The objective assembly 200 further comprises an LED array holder 218 that supports a plurality of LEDs 220. The LEDs 220 may comprise for example, UV LEDs from Sensor Electronic Technology, Inc., Columbia, S.C. Additional lenses 222 such as hemispherical front lenses or meniscus lenses may also be provided at the nose portion of the modified objective assembly 200. In order to maximize the total amount of power emitted from the LED 220 that gets projected to the sample beneath the objective 84, the LED 220 must be as close to the sample as possible. Thus, for some applications, excessive total light loss may result by positioning the LED 220 above or towards the top of the objective 84. However, the use of the LED holder 218 allows the LEDs 220 to be positioned proximate to the sample on the sample substrate 24.

The LEDs 220 are arranged in an annular array and are supported by the LED array holder 218 around and external to the objective assembly 200 to illuminate the sample. This arrangement may produce specific narrow wavelength bands without the need for filters. The incident light from the LEDs 220 can produce emitted light from the sample at the same wavelength due to scattering or at longer wavelengths due to fluorescence. The emitted light is collected by the objective assembly 200 and is focused onto the camera 86 (or onto an eyepiece for viewing or other suitable optical device). Additionally, optional filtering may be required, depending upon the specific application.

Figure 16:
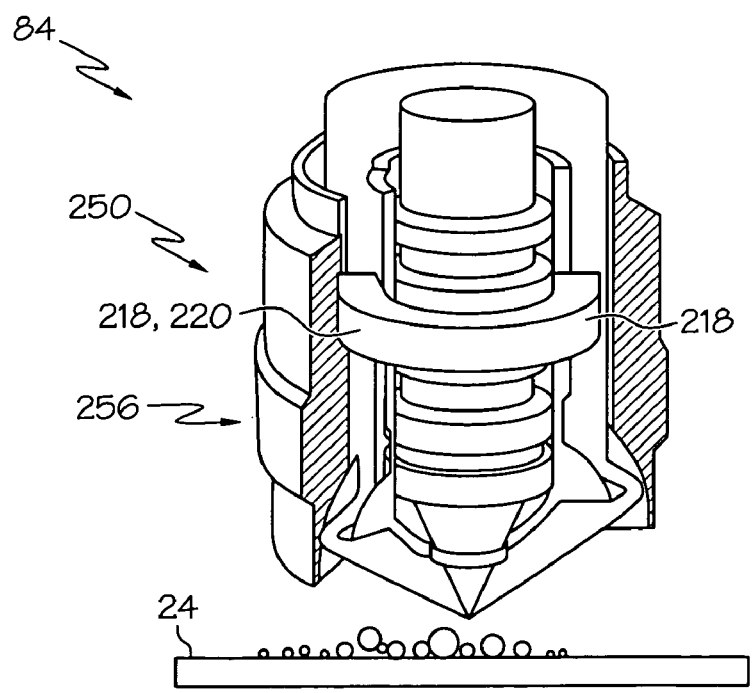
FIG. 16 is a cut out view of an objective assembly according to another embodiment of the present invention.

A darkfield system may utilize a high power xenon lamp for the source 80, which is filtered down to UV and passed through a darkfield objective because UV light below 320 nm does not transmit well through standard microscope objectives. Referring to FIG. 16, according to an aspect of the present invention, the objective 84 described with reference to FIG. 4 may be implemented as an objective assembly 250 that is substantially the same as the objective assembly 200 except that the LEDs 220 and corresponding LED holder 218 are positioned internal to the assembly. Using this arrangement, a darkfield lens is used as the lens element to direct the light from the LEDs 220 to the sample substrate 24 and thus the first optical path 72 and corresponding light source 80 and any appropriate lenses, filters or other optical elements 82 are not required. The LEDs 220 are held by the LED holder 218 in an annular array, e.g., in a region 256 around the central optical core of the objective assembly 250. The LEDs 220 take up the region where typical illumination from an arc lamp light source would be directed. The light is directed downward and is reflected onto the sample surface of the sample substrate 24 for darkfield illumination by the darkfield lens.

For fluorescence detection with mid to far ultraviolet illumination, the use of a darkfield objective assembly 250 may be cost effective because a typical through-the-lens illumination objective arrangement would require an objective assembly that is typically more costly than that of a glass bright field lens. The use of the darkfield approach still requires a light source and optics that may reduce the optical throughput of the system and such considerations should be taken into account.

Figure 17:
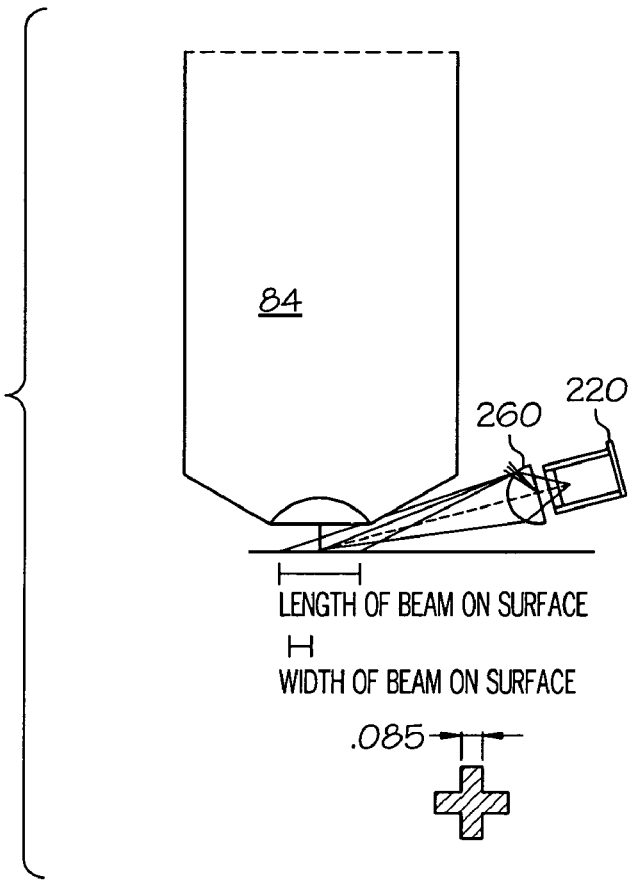
FIG. 17 is a partial side view of the objective of FIG. 15, illustrating the orientation of an LED about the outer periphery of the objective.
Figure 18:
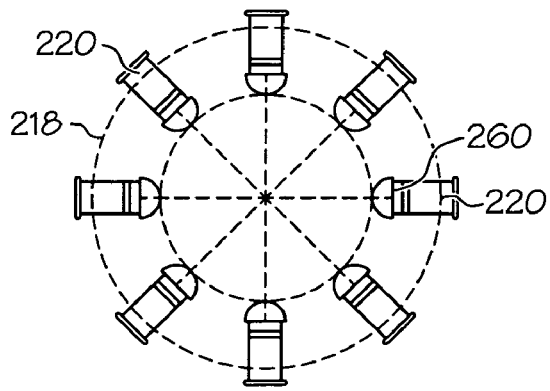
FIG. 18 is a to view of a plurality of LEDS in an LED holder of the objective assembly of FIG. 15.
Figure 19:
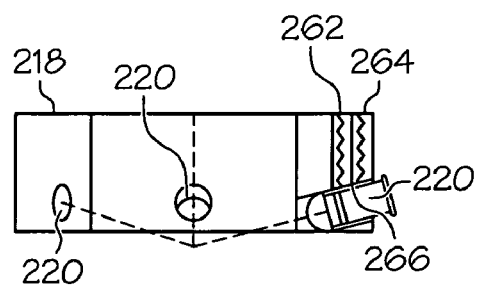
FIG. 19 is a cut out side view illustrating an adjusting mechanism for directing the LEDs mounted in the LED holder of FIG. 18.

It is also possible to combine UV and visible LEDs, e.g., in the illumination approach for fluorescence imaging as described with reference to FIG. 15 and/or 16. This arrangement may include additional focusing lenses and/or combinations with other LEDs for visible sample illumination. Referring to FIGS. 17-19, UV LEDs are mounted along the outer edge of a long working distance (LWD) objective, e.g., such described with reference to FIG. 15. This location for the LEDS allows a plurality, e.g., up to 8 or more LEDS, to be arrayed about a standard objective. As shown in FIG. 17, a UV LED, e.g., in a TO-18 can, is driven to emit a beam that passes through a lens 260, e.g., a 6 mm hemispherical lens or other focusing element that maximizes intensity of a small sample spot, to be imaged down to an elliptical spot. For example, the LED 220 may comprise a S-ET UV TOP 285 nm diode. In FIG. 17, the LED holder 218 illustrated in FIG. 15 has been removed for clarity of illustration.

The lens 260 may comprise any suitable optical element, e.g., a fused silica hemispherical window. The beam, e.g., having a 280 nm wavelength, is angled downward, e.g., at an angle of approximately 14 degrees. With this configuration, a pattern of excitation for four diodes arranged along the circular holder spaced substantially 90 degrees apart may realize a "+" pattern. In addition to UV LEDs, additional non-UV LEDs can be included. These non-UV LEDs can be chosen to help with focusing or to help improve edge contrast of the particles being observed through the objective.

FIG. 18 shows an exemplary arrangement of the LED holder 218, e.g., implemented as a block of aluminum that has been machined out to hold eight LEDs 220. FIG. 19 illustrates one of the LED mountings for the LED holder of FIG. 18 in greater detail. As illustrated, the LED holder 218 comprises a shim cylinder set screw 262, a diode set screw 264 and a shim cylinder 266 for adjusting each diode 220 and to help with beam alignment. Each lens 260 is fixed in place using the shim cylinder 266 and corresponding shim cylinder set screw 262 to properly position and align the lens and then the LED package is slid into the LED holder 218 and is properly positioned using the diode set screw 264 with the help of the shim cylinder 266 and may be focused as necessary using the above adjustments. For example, the LEDs may be adjusted for optimal focus on the sample by sliding the diode 220 in the shim cylinder 266.

Figure 20:
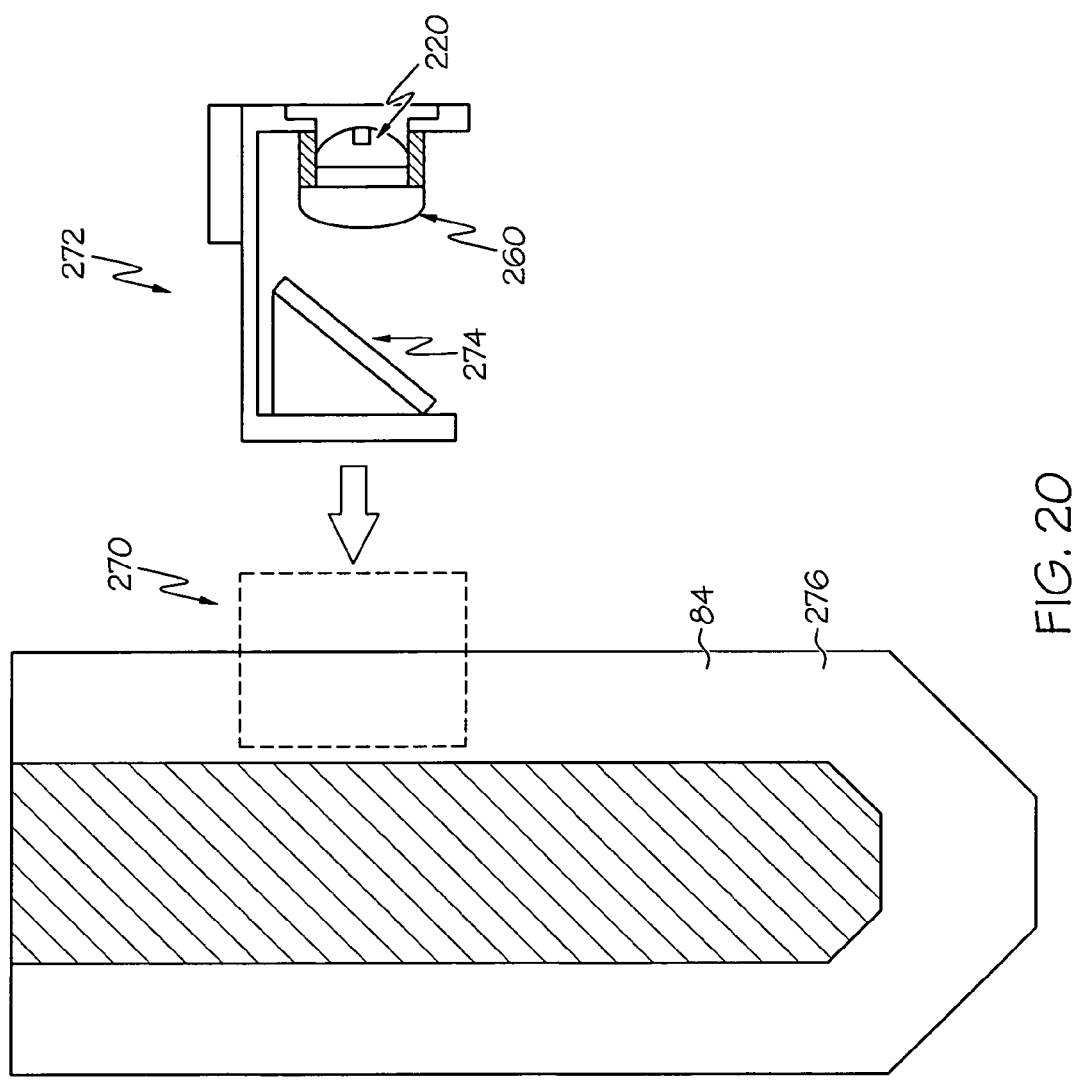
FIG. 20 is a schematic view of an objective wherein LEDs are installed through an aperture in an objective housing.

Referring to FIG. 20, an exemplary internal illumination configuration is illustrated, which may be used in addition to, or instead of the external illumination described with reference to FIGS. 17-19. Multiple LEDs 220 may be used to focus their light beneath the objective 84 without passing through the main central optics of the objective 84. A clear ring aperture is provided around the main central objective lens. This clear aperture has an off-axis parabolic mirror that can focus the light in that circular aperture down to a spot directly in the field of view of the objective.

At least one aperture 270 is provided in the side of the darkfield objective 84 for receiving an LED package 272. Each LED package 272 comprises a housing that supports an LED 220 and a lens 260, e.g., a hemispherical fused silica lens as described in greater detail herein. The housing further supports a turning mirror/filter mirror 274 for redirecting the beam from the LED 220. The LED package 272 is inserted in the aperture 270 in the darkfield objective 84. The light from the LED 220 is reflected off the turning mirror/filter 274 and is directed to a ring mirror 276 within the lower portion of the objective 84. The ring mirror 276 further directs the beam to the sample. The turning mirror/filter 274 is designed to filter possible noisy spectral signals coming from typical LEDs 220. The filter 274 may comprise, for example, a small prism in a chamber having a specialized coating. The ring mirror 276 may comprise a parabolic off axis mirror that is completely circular. Thus, multiple LED packages can be installed into one dark field objective, e.g., by including multiple apertures 270, each receiving an LED package 272.

As an alternative to mounting LEDs in or about the objective 84, a diode box having one or more light sources such as LEDs may be provided separate from the objective 84. Light from the LEDs is routed to the appropriate locations with respect to the objective 84 via a fiber optic connection. For example, in the darkfield objective example, the fiber optic lines can be directed to holes arrayed around the objective 84. The holes in the side may be high enough and at shallow enough angles that they will allow the fiber to direct downward. By following the light path to the light cone for sample illumination, the lens may be bypassed without significant UV loss in delivering UV power on the sample.

Still further, other techniques can be used, e.g., ultraviolet transmission bypassing of the lens gap ring of the objective 84, and improved coating properties of the lens to reflect a relatively greater percentage of the UV light may be utilized.

Particulate Discrimination

Figure 21:
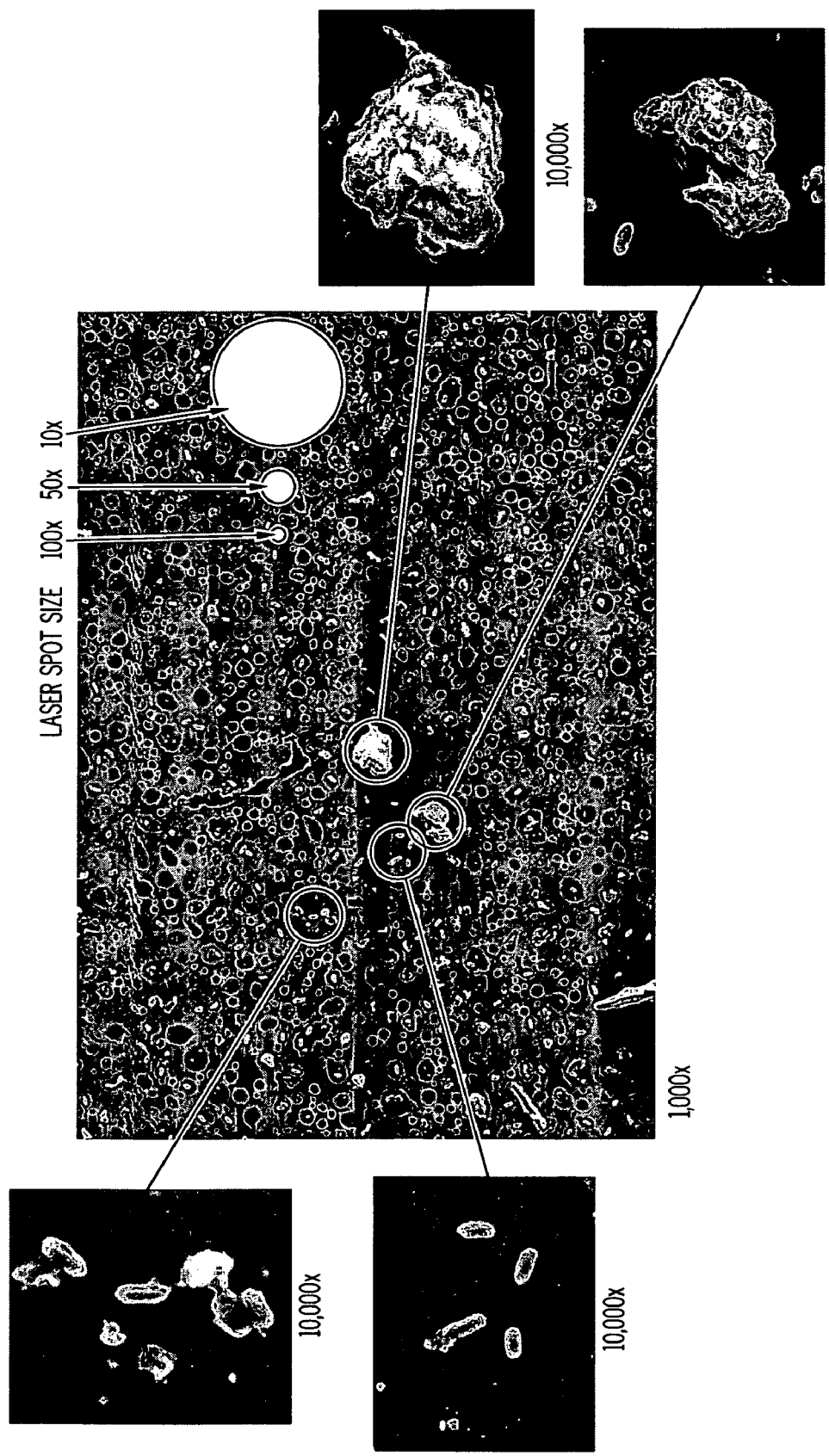
FIG. 21 is a photographic representation of a sample illustrating the focus of an interrogation beam at various objective magnifications.
Figure 22:
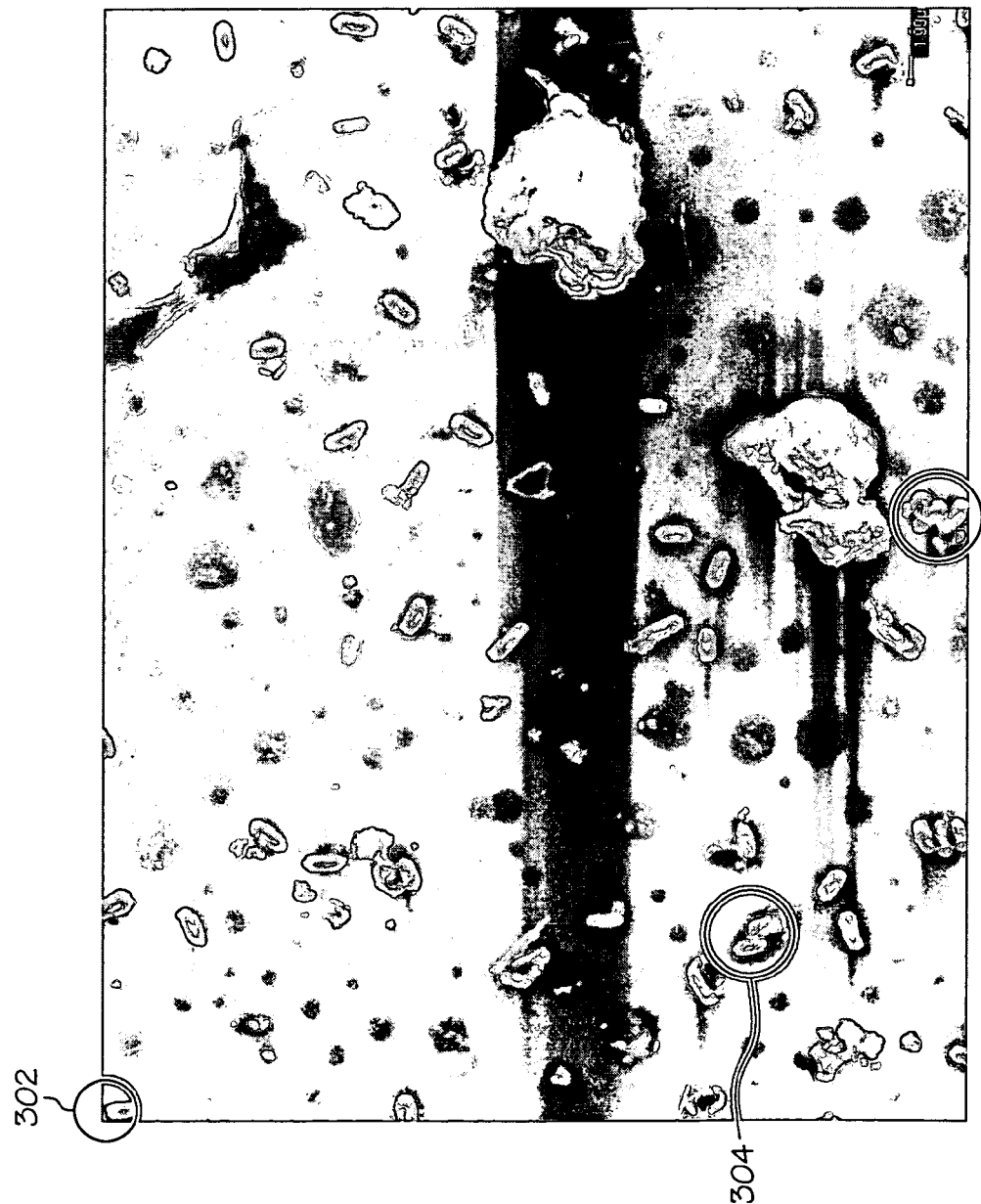
FIG. 22 is a photographic representation illustrating particles of interest having varying sizes.

Referring to FIG. 21, a scanning electron microscope (SEM) illustrates a sample substrate containing a sample that includes Bg and background particulates. A laser spot size on the sample substrate 24 is illustrated using ×10, ×50 and ×100 objective magnification, such as by adjusting the magnification of the objective lens 84 in the optical system 70 illustrated in FIG. 4. As noted above, the ×10 objective results in a larger field of view, and thus a greater number of background particulates may be considered in the analysis. Also as noted above, by contrast, the ×100 objective results in the smallest field of view and thus the least amount of background particulates that may be considered in the analysis. Thus, targeting particles allows background discrimination to be enhanced by reducing the amount of impurities and background matter that are interrogated within the laser spot size. FIG. 22 is an enlargement of a portion of the sample area of FIG. 21 to illustrate that Bg spores are evident on the sample substrate as single spores 302, double spores 304 and agglomerated clusters of spores 306.

FIGS. 21 and 22 illustrate that, regardless of the objective magnification, e.g., whether using a 10×, 50×, 100× or other suitable magnification, the interrogation area is extremely small compared to the sample area. FIGS. 21 and 22 also illustrate that, depending upon the coverage density of particulates per sample area, there may be a significant number of particulates that may qualify as candidate target particulates. When establishing target locations for subsequent targeted interrogation, e.g., using the spectrometer 88, the sample area on the sample substrate can be subdivided into multiple regions or fields of view and the subdivided regions may be individually processed to determine whether any particulates would qualify as reasonable target particulates for subsequent interrogation. For example a sample area of approximately 1 mm in diameter may be subdivided into a plurality of 30 micron×30 micron areas. Alternatively, the size of each field of view may be selected to realize a predetermined range of particles, e.g., approximately 20 to 50 particulates per view where the particulate composition may comprise single or agglomerations of particulates of interest. From each subdivision, one or more target locations may be specified as target locations for subsequent Raman interrogation as noted in greater detail herein. A corresponding ranking scheme may then used to select the top candidate particulates for detailed, specific interrogation.

Figure 35A:
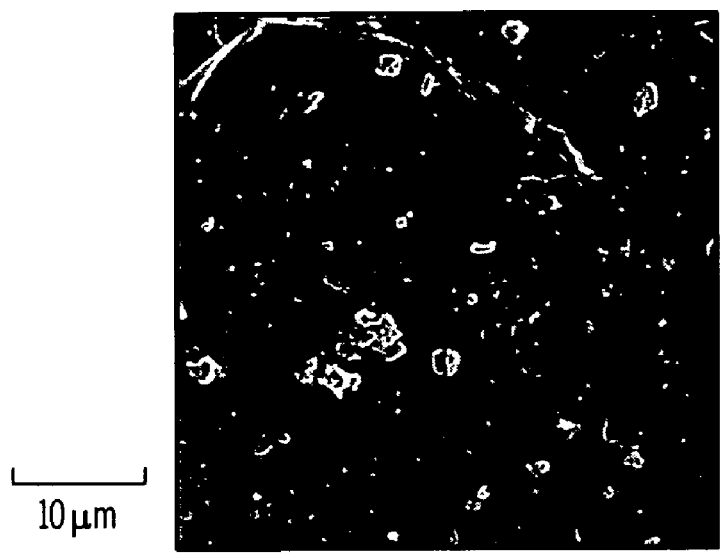
FIG. 35A is a scanning electron microscope photographic image of a particulate sample section.
Figure 35B:
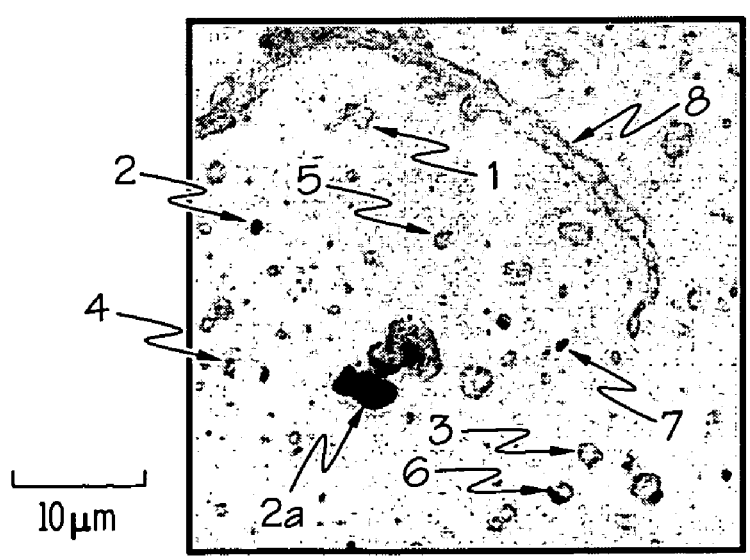
FIG. 35B is a bright field microscope image of the particulate sample section of FIG. 35A.
Figure 35C:
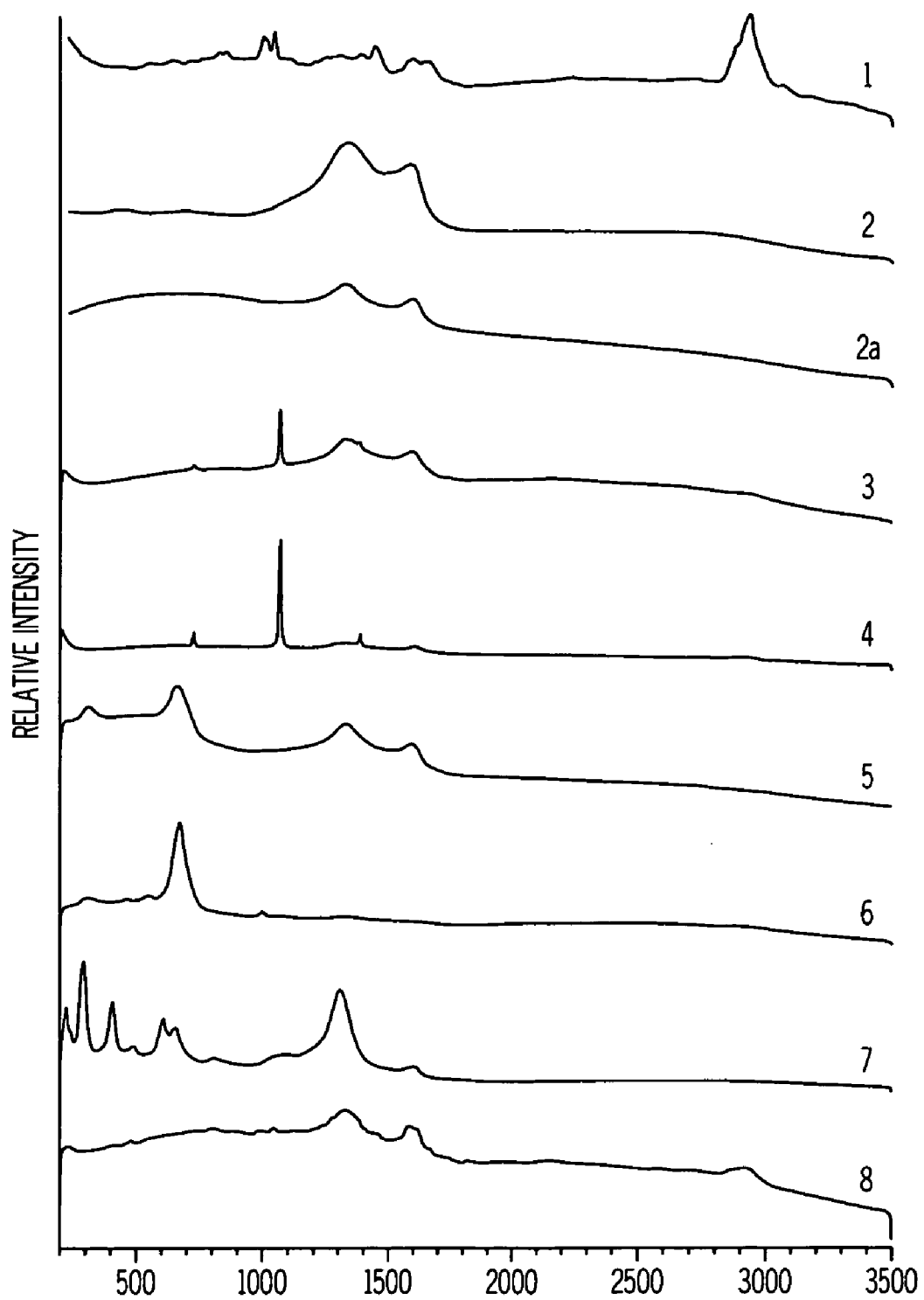
FIG. 35C illustrates the Raman spectra of select individual particles within the particulate sample section of FIG. 35A.

The system may be able to discriminate biological particles from a mixture of ambient particles. In one exemplary test, an ambient bulk sample spiked with an aerosolized biological simulant (*Bacillus globigii* (Bg) spores) was collected and subsequently analyzed. FIGS. 35A and 35B show a scanning electron microscope (SEM) and bright field optical microscope images, respectively, of a portion of the collected sample. Arrows identifying nine individual particles were targeted for Raman interrogation and the corresponding Raman spectral traces of those nine particles are shown in FIG. 35C.

These spectra show distinctive fingerprints for the individual targeted particles. For example, the particle labeled as "1" in FIGS. 35A and 4B was identified as a Bg spore based on its Raman spectrum, including a main spectral feature at a much higher Raman shift than observed for any of the other nine targeted particles. The particles identified as "2" and "2a" were identified as diesel soot particles based a previously characterized diesel soot spectrum. Particle "3" suggests a mixture of diesel soot and of the substance shown in the trace corresponding to particle 4, which is likely a sulfate compound. Inspection of the traces of FIG. 35C illustrates the potential chemical and biological characterization of individual particles.

Figure 36:
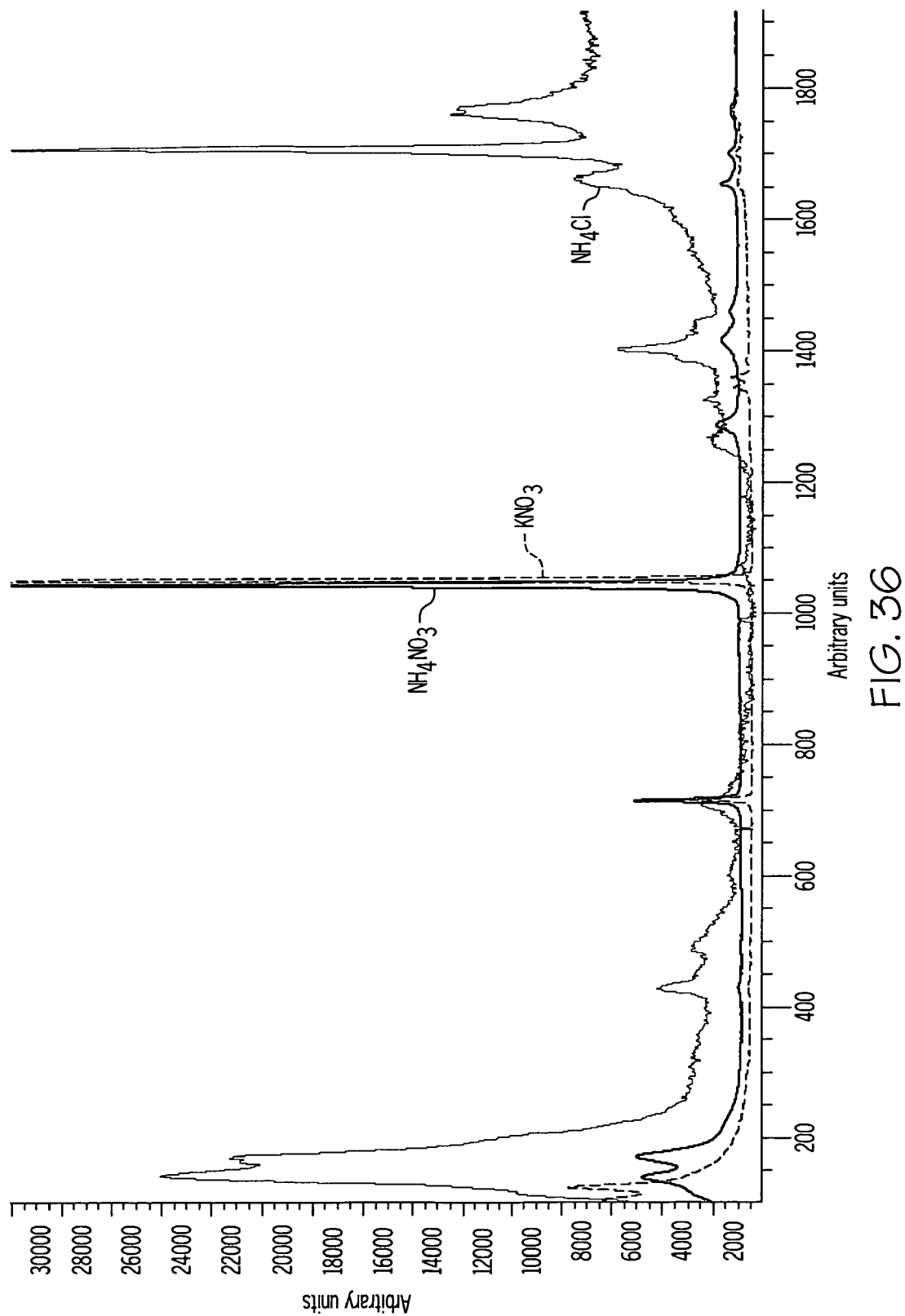
FIG. 36 is a plot of the Raman spectral signatures of ammonium nitrate, potassium nitrate and ammonium chloride.

Nitrates and sulfates are common air pollutants widely found in certain industrial areas and in urban areas. Referring to FIG. 36, a plot illustrates that Raman analysis may be utilized to discriminate different nitrates, e.g., ammonium nitrate and potassium as well as different ammonium compounds, e.g., ammonium nitrate and ammonium chloride.

Figure 37:
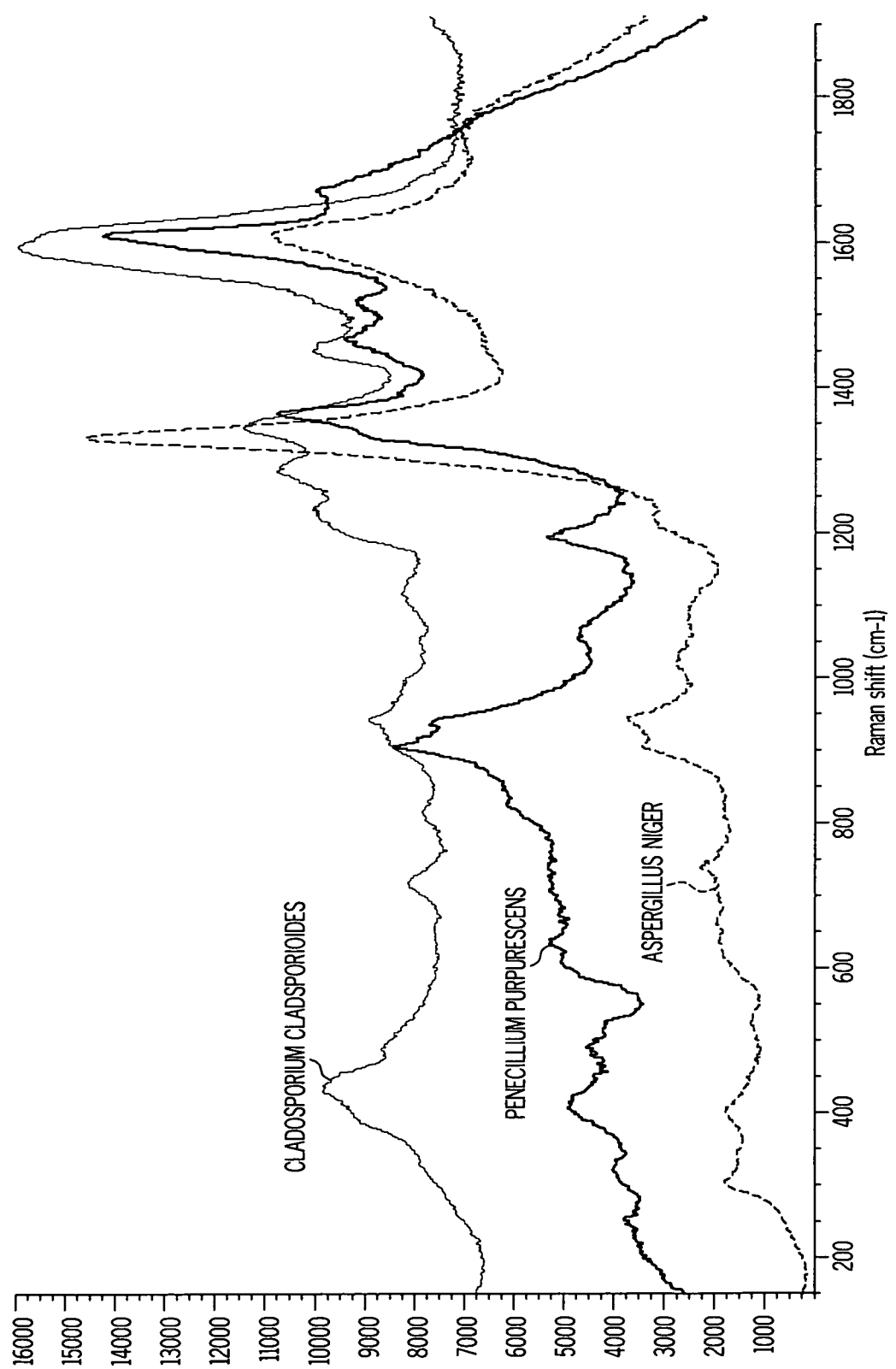
FIG. 37 is a plot of Raman spectral signatures of fungal spores, *Aspergillus niger* ATCC 10698, *Penicillium purpurescens* ATCC 10485, *Cladosporium cladosporioides* ATCC 66669.

Common fungal allergy sources include but not limited to *Aspergillus* species, *Penicillium* species, and *Cladosporium* species. The Raman spectral signatures of fungal spores including *Aspergillus niger* ATCC 10698, *Penicillium purpurescens* ATCC 10485 and *Cladosporium cladosporioides* ATCC 66669 are illustrated in FIG. 37. The ability to discriminate these fungal spores provides a quick diagnostic method for fungal contaminated air environment or sources.

The capabilities of the detection system 10 are not limited to the identification of those particulates described in detail herein. Rather, the above techniques can be applied to a number of additional or alternative particulates, including fungal spores, bacterial spores, vegetative bacterial cells, proteins, various *Aspergillus* species, including but not limited to *Aspergillus fischeri* (ATCC18618), *Aspergillus paradoxus* (ATCC16918), *Aspergillus ornatulus* (ATCC16921), *Aspergillus niger* (ATCC10698), and *Aspergillus niveus* (ATCC56745) and yeast cells, e.g., *Candida utilis* (ATCC9950) cells.

The Storage Station

Referring back to FIG. 1, storage station 18 may comprise a substrate storage location 120, a sample storage location 122 and an optional cleaning station 124. The substrate storage location stores clean sample substrates to be used for sampling by the collector station 14. The particular configuration of the substrate storage location 120 will depend upon the type of media used for the sample substrate 24.

The substrate storage location 120 may be able to store a plurality of discrete sample substrates 24. For example, the sample substrate 24 may comprise a relatively small slide, e.g., 1 inch by 1 inch in diameter, and $1/16$ inch thick. The slide may comprise an aluminized Mylar substrate or an aluminum coated glass slide. An aluminum coating may be useful if utilizing a Raman analysis for targeted particulate interrogation because the molecular structure of the aluminum coated sample substrate has no sharp vibrational modes and thus does not significantly contribute to the Raman spectra. However, other coatings and sample substrate materials may alternatively be used. For example, gold and/or silver coating may be useful where it is important to magnify the Raman intensity. Surface enhanced Raman spectroscopy (SERS) or other surface roughening techniques are not required to collect samples on the sample substrate 24. Rather, the use of a dry sample substrate 24 may be used to promote substrate reuse and recycling as noted in greater detail herein.

Alternatively, the sample substrate may comprise an aluminized Mylar tape or polymer tape as will be described in greater detail herein. The tape may be continuous, e.g., stored on opposing drums in a manner similar to a cassette tape or provided in discrete sections. Moreover, the sample substrate 24, regardless of whether provided in discrete slides or continuous roll form, may be dry, i.e., have no applied coatings, or an adhesion promoting coating having minimal or negligible Raman background may be applied to the sample substrate 24. An adhesion promoting coating may be applied to the substrate to selectively promote biological materials or other particulate features of interest.

The sample storage location 122 provides an area to sort, store and archive sample substrates 24 that have samples deposited thereon. After processing by the optical interrogation station 16, the used sample substrates 24 may be stored in, and retrieved from, the sample storage area 122. This allows collected sample areas to be preserved for subsequent challenge, analysis and further data processing.

The optional cleaning station 124 replenishes usable sample substrates by obtaining a sample substrate, e.g., from the sample storage area 122 by selecting a sample substrate that did not contain biological or chemical particulates of interest. The cleaning station 124 cleans the used sample substrate, and returns the sample substrate to the substrate storage station 120. Sample substrates may be cleaned using brushes, liquid treatments and other processes. As noted above, the use of dry impaction of the sample onto the sample substrate may facilitate relatively easier substrate cleaning processes compared to treated or coated sample substrates.

Accordingly, the biological and chemical detection system 10 may operate continuously and autonomously for a period of time. The time of operation will depend upon a number of factors including the sample collection and analysis period, the number of sample substrates 24 and whether each sample substrate 24 is a single use substrate, or a reusable substrate that is reused for multiple iterations of sampling and sample analyzing.

Tape Processing System

In many sampling applications, only a thin layer of material at the surface of the sample collecting substrate is functionally important. For this reason, many native (solid) substrate materials are coated with thin layer(s) of non-metal and/or metal to provide the sample collection surface while reducing the cost over a solid substrate of the needed material, e.g., aluminized Mylar. However, only a small area of the surface is used to hold samples. This means that the volume of substrates is relatively large compared to what is actually used to collect samples. The coatings may also be expensive. Some exemplary conventional coating materials include gold, resulting in additional cost to coat the unused areas.

According to yet another aspect of the present invention, the sample substrate 24 comprises a small piece of thin and flexible ribbon that is automatically mounted in a carrier, e.g., from a spool provided as part of the storage station 18, so that the amount of ribbon is small for each cycle. The carrier is re-used, which allows storage, handling, mounting and registration using methods for slides that are highly developed.

Figure 23:
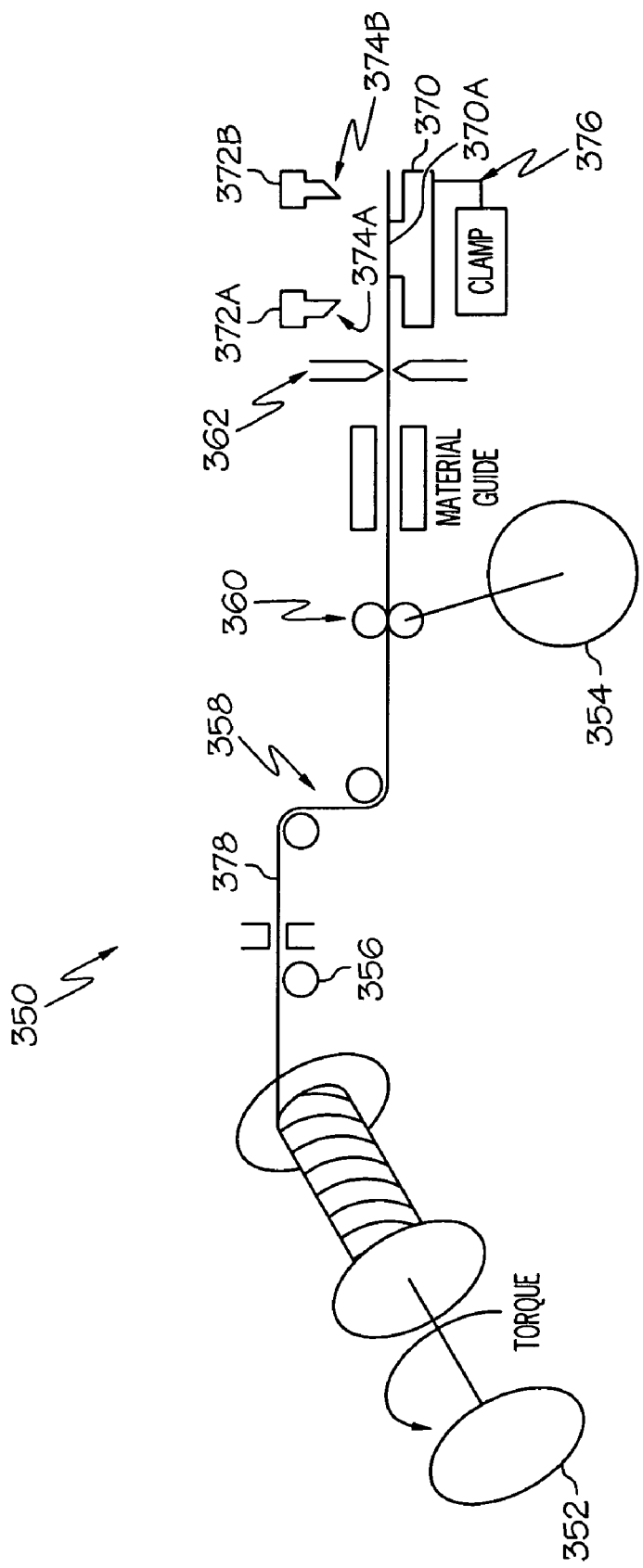
FIG. 23 is a schematic block diagram of a system for installing a ribbon on a carrier for sample collection.

Referring to FIG. 23, the system 350 incorporates two servo drives and corresponding motors 352, 354, a plurality of rollers, e.g., alignment rollers 356, optional flattening rollers 358 and feed rollers 360, a shear 362 and other necessary mechanical devices, such as actuators, conveyance mechanisms, etc. The system 350 may be provided, for example, as part of the storage station 18.

A carrier plate 370 has two attached, spring loaded bars 372A, 372B. The first spring loaded bar 372A has at least one chiseled point 374A. Correspondingly, the second spring loaded bar 372B has at least one chiseled point 374B. The size, positioning and orientation of the chiseled points 374A, 374B on their corresponding spring loaded bars 372A, 372B will depend, for example, upon the width of the ribbon. The carrier plate 370 is positioned and clamped at a loading station 376. In an initial state, the two spring loaded bars 372A, 372B are held, e.g., by suitable actuator(s), in a lifted or retracted position relative to the carrier plate 370.

A fixed length of tape 378 is fed out by the servo 352 to a position between the spring loaded bars 372A, 372B and the upper surface 370A of the carrier plate 370. The bar 372B furthest from the feed rollers 360 is pressed down such that the point 374B punctures and fixes the far end of the ribbon 378 to the carrier plate 370. The servo drive 352 then changes to a torque mode of operation and maintains a fixed tension on the ribbon 378. The spring loaded bar 372A closest to the feed rollers 360 is pressed down and the point 372A punctures the ribbon 378. The servo 352 then changes back to position mode and the shear 362 cuts the ribbon 378, thus separating the portion of the ribbon 378 wound about its corresponding spool and the ribbon 378 now attached to the carrier plate 370.

The ribbon 378 is now being held flat against the top surface 370A of the carrier 370 by the bars 372A, 372B. Thus, this surface provides a convenient surface for sample collection. In this regard, the carrier plate 370 and corresponding ribbon 378 may be used as the sample substrate 24 in lieu of the slides discussed above, e.g., as part of the chemical and biological detection system 10 of FIG. 1. The carrier 370 is unclamped and may be handled at this point, e.g., by the substrate storage station 120 to be transported to the collector station 14 and subsequently, to the optical interrogation station 16.

Figure 24:
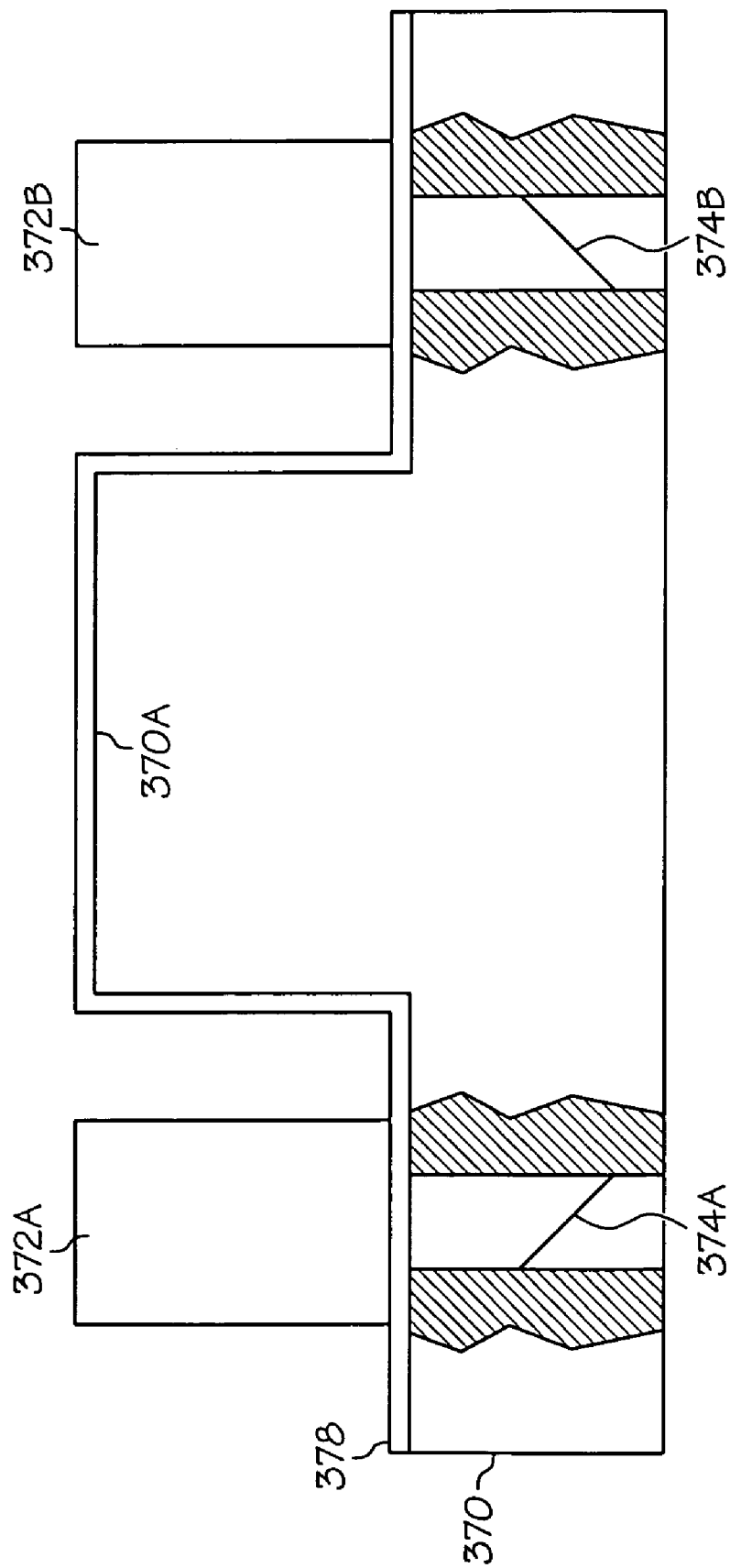
FIG. 24 is an illustration of the carrier of FIG. 23 having a ribbon installed thereon.

Referring to FIG. 24, the carrier base 370 is illustrated with a section of the ribbon 378 attached thereto by the bars 372A, 372B. After a sample has been collected on the section of ribbon, e.g., by the collection station 14, and after the collected sample has been processed, e.g., by the sample interrogation station 16, the section of ribbon 378 is stripped from the carrier plate 370, e.g., using suitable actuator(s) to remove the bars 372A, 372B from the carrier plate 370. Once the section of ribbon 378 is removed, the carrier plate 370 may be reused. The section of ribbon 378 may be discarded, e.g., if no chemical or biological particulates of interest were located on the sample deposited on the section of ribbon 378. Alternatively, the section of ribbon 378 may be archived, e.g., in the sample storage station 124 if desired by the particular application, e.g., where the sample deposited on the section of ribbon 278 contains particulates of interest.

The System Transport

Referring back to FIG. 1, a transport 126 is provided to relocate the sample substrate to the various stations of the biological and chemical detection system 10. The transport 126 may comprise a rotary stage or stages, or other system that allows the sample substrate to be moved within the biological and chemical detection system 10 at timing events determined by the system controller 60. The substrate storage location 120 is operatively configured to position a new sample substrate 26 on the transport 126 so as to automate or semi-automate sampling and testing. The transport 126 then delivers the sample substrate 24 to the collection station 14 and may optionally load a new sample substrate 24 onto the transport 126 from the substrate storage area 120. After a sample has been deposited on the sample substrate 24 at the collector station 14, the transport 126 advances the sample substrates 24 so that the sample substrate previously at the collector station 14 is advanced to the optical interrogation station 16. A new sample substrate 24 may be simultaneously advanced to the collector station 14, etc. The transport 126 may also provide the positioning stage for targeted interrogation by the spectrometer 88 at the interrogation station 16 as described in greater detail herein.

The transport 126 allows continuous or nearly continuous sampling by the collection station 14. For example, the collection station 14 may derive a new sample area every five minutes or other suitable time interval. Some sample buildup may dwell for a relatively long period in clean air and some samples may advance more rapidly if the air is particularly heavy with particulates. As such, the rate at which the sample areas are collected may be both application and operation/ environment specific. Where discrete sample substrates 24 are used, interruptions of sample collection, e.g., due to substrate handling, are kept short relative to the sample collection time, e.g., on the order of 10 to thirty seconds for a typical five minute sample collection process.

The System Controller

Again referring to FIG. 1, the system controller 60 may further provide a command and control interface 128 that allows an operator to quickly set up and begin operation of the biological and chemical detection system 10. Start up times may be on the order of approximately one hour or less depending upon the particular implementation of the various stations within the biological and chemical detection system 10, including the time required for example, to unpack, identify, set up and load any required consumables in the correct manner, even during night operations, such as by using red lens lights, etc. Control functions may be performed by direct interaction with the system controller 60 or via remote control from a remote location, e.g., using a wireless or wired communications connection 130.

An optional display 132 may also be provided for the continuous or periodically updated status of the system and various system components, system operations, current operating mode and analysis results. The display 132 may further provide embedded design documentation of component manuals etc., for viewing by the operator.

The system controller 60 can optionally provide several modes of operation, examples of which include a startup mode, a standby mode, a standard mode, a single sample mode, a collection only mode, a manual analysis mode and a shutdown mode. The start-up mode, also referred to herein as an initialization mode, may be entered when power is applied. During start-up, all necessary actions are performed to bring the biological and chemical detection system 10 to a steady-state condition ready to analyze samples. For example, the start-up mode may cause the spectrometer 88 to implement an automatic calibration as set out in greater detail herein. When all start-up actions have been completed the controller 60 may automatically change to Standby mode. Start-up may be completed within a predetermined time, e.g., approximately 30 minutes or less exclusive of time for temperature stabilization of the interior of the housing 12 and other similar factors.

In standby mode, the controller is fully operational and ready to start the collection station 14 to begin sampling. The standby mode may be entered automatically from Start-up mode or manually from any other mode. In standard mode, the controller 60 operates the biological and chemical detection system 10 to sample and analyze repetitively, producing the results of identification, e.g., over the communication interface 130 and/or on the display 132 as information becomes available.

In single-sample mode, which may be entered from standby mode, a single sample substrate 24 is processed through the biological and chemical detection system 10. That is, one sample substrate 24 is loaded from the substrate storage location 120 to the collection station 14, then to the optical interrogation station 16 and then to the sample storage location 122 of the storage station 18. If desired, the sample substrate 24 may be retrieved from the housing 12 via a suitable arrangement, such as an outfeed magazine 134.

In collection-only mode, sample substrates 24 are moved from the substrate storage location 120 of the storage station 18, to the collection station 14 where a sample collection is performed. After a suitable sample has been collected, the corresponding sample substrate 24 is moved to the sample storage location 122 of the storage station 18. However, no analysis or optical interrogation of the sample area is performed.

Correspondingly, in manual analysis mode, the biological and chemical detection system 10 may provide for an operator to manually load a sample substrate 24 via a suitable infeed arrangement 136 or load a sample substrate 24 onto the transport 126, e.g., from the sample storage location 122. The transport 126 moves the sample substrate to the optical interrogation station 16 for data analysis and identification as explained in greater detail herein. Accordingly, the transport 126 and the optical interrogation station 16 may be further configured so as to be able to accurately and repeatably register the sample substrate 24 at least at the optical interrogation station 16, e.g., by controlling the transport 126 and targeting resolution of the spectrometer 88, so that the same sample and sample substrate 24 are analyzed consistently during analysis and interrogation.

Shutdown mode controls the sequenced shutdown of the biological and chemical detection system 10 and includes, but is not limited to, cooling equipment, parking moving components, and closing open data files. Once shutdown is complete power may be removed from the system.

Where a plurality of operating modes is provided, it may be desirable to establish operational rules that determine transitions between the various modes. For example, a rule may assert that the standard mode may only be entered from and exited to standby mode. When exiting standard mode, analysis of all in-process sample substrates 24, i.e., sample substrates 24 that have been removed from the storage location 120 of the storage station 18 or are otherwise positioned on the transport 126, are completed and the corresponding sample substrates 24 are returned to the sample storage location 124 before transitioning modes. For example, sample substrates 24 may have to complete sample collection at the collection station 14 and/or analysis and identification at the optical interrogation station 16 before the controller 60 allows the system to enter standby mode. Other control flow may alternatively be implemented, depending upon the specific application.

A Tape Based Transport System

Figure 25:
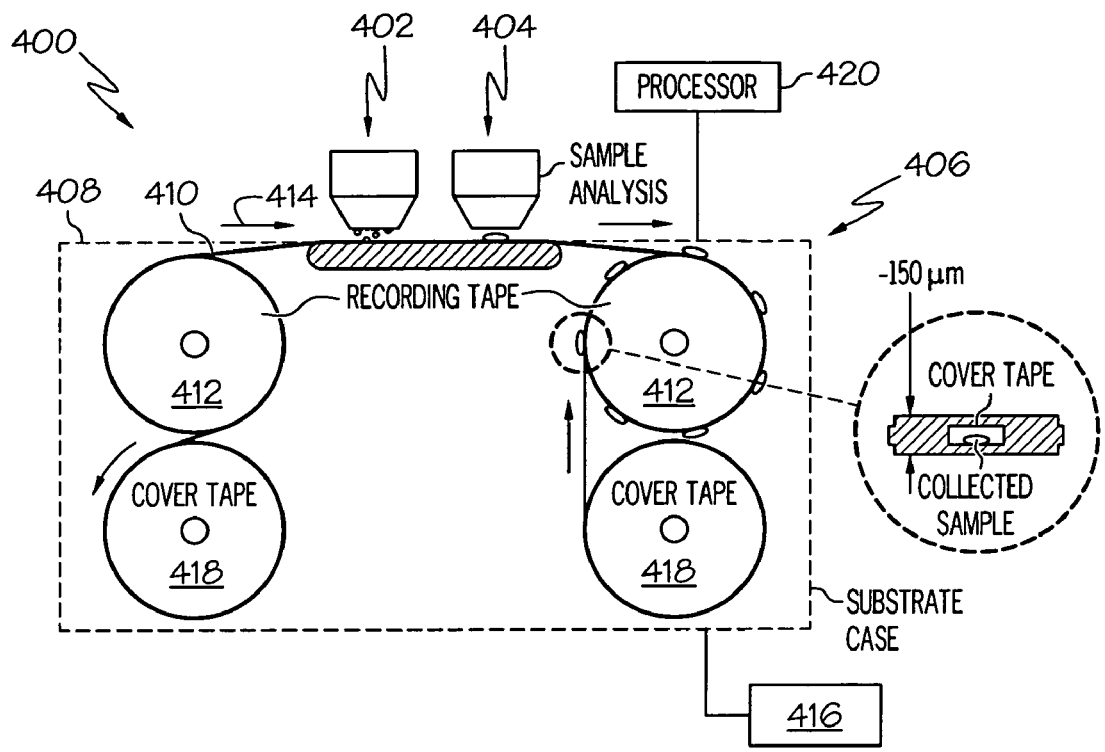
FIG. 25 is a schematic block diagram of the biological and chemical detection system wherein samples are collected and stored on a tape.

Referring to FIG. 25, as noted above, samples can alternatively be collected on a continuous substrate, for example, on a tape, that passes under sample collection and interrogation stations. The tape can move in a continuous or semi-continuous manner. In a manner analogous to using the transport 126 described with reference to FIG. 1, samples collected on the tape by the collection station are advanced to the optical interrogation station where the previously collected sample is targeted for interrogation by the first optical system, and the targeted regions of the sample are subsequently interrogated by a corresponding second optical system. The sample is then transported to a storage location, e.g., wound onto a spool of the tape. In this regard, the tape may wind from a first spool to a second spool, in a manner analogous to a conventional cassette tape. Alternatively, the tape may be continuous so as to run in an infinite loop, e.g., where it is desirable to provide extended, continuous sampling. The later configuration requires a cleaning station that removes the collected sample from the tape after the sample has been analyzed.

As shown, the tape-based system 400 comprises a sample collection station 402, a optical interrogation station 404 and a sample storage station 406. The sample storage station comprises a cassette tape mechanism 408 as will be described in greater detail below. The system 400 utilizes a flexible substrate tape 410, e.g., a polymer or other suitable material, which may optionally include an applied coating, e.g., aluminum, plasma treatment, etc.

The sample storage station 406 comprises a reel mechanism having two reel to reel, sample recording substrate tape reels 412 that can be driven forward towards the arrow direction 414 or reversed against the arrow direction 414 by a suitable drive device 416. The sample storage station 406 further comprises a tape covering mechanism having two sample cover tape reels 414 for covering and the collected samples.

The substrate tape 410 can be advanced and stopped at a desired position, e.g., by the drive device 416, to a suitable location on the substrate tape 410 where an aerosol sample can be collected, by the sample collection station 402, e.g., through impaction by an aerosol impaction collector. The sample collection station 402 may collect each sample in a manner analogous to the collection station 14 described with reference to FIG. 1, e.g., by using a suitable collector 20 and pump 22. The aerosol sample can thus be impacted as a small sample spot of approximately 1.0 to 1.5 mm on the substrate as noted in greater detail herein.

After aerosol sample collection by the sample collection station 402, the collected sample can be forwarded by the reel mechanism of the sample storage station 406 via the drive device 416 to the optical interrogation station 404. The optical interrogation station 404 may comprise multiple optical system components to selectively target and interrogate the sample in a manner analogous to the optical interrogation station 16 described more fully herein. The analysis results are communicated to the processor 420, which is analogous to the system controller 60 and corresponding data analysis algorithms 62 described in greater detail herein. For example, the optical interrogation station 404 may comprise a micro-Raman detector, under which the collected sample can be visible or fluorescently imaged and analyzed for its fluorescent, size, shape and/or spectral characteristics.

At the completion of the analysis, the substrate is driven forward by the drive device 416 and the previously analyzed sample on the substrate tape 410 is covered by the covering tape mechanism so as to protect the sample from scratching or damaging of other components of the system.

Figure 26:
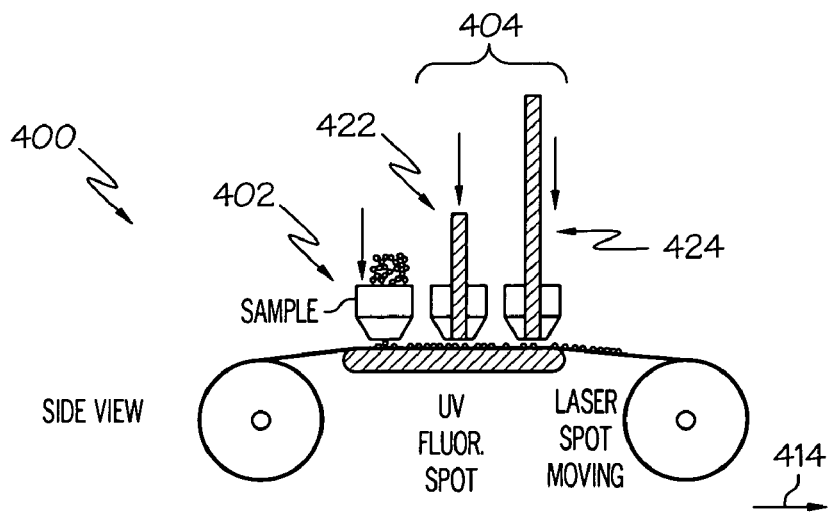
FIG. 26 is a schematic side view of the tape system of FIG. 25.
Figure 27:
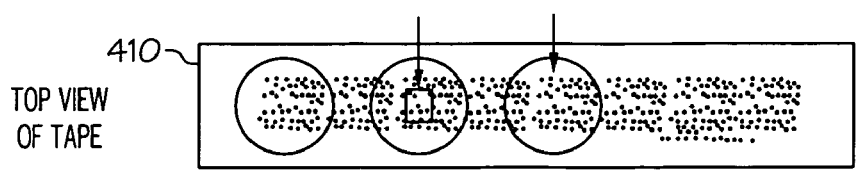
FIG. 27 is a top view of the tape of FIG. 25.

The use of a tape-based system compared to a discrete slide may be advantageous where, for example, it is desirable to operate in a semi-continuous or even continuous sample collection, analysis and storage mode. Referring to FIGS. 26 and 27, the substrate tape 410 may comprise a belt that is used to collect each sample from the sample collection station 402 by moving, for example, continuously or in short steps. Thus, the sample area may comprise a length that significantly exceeds its width in area as best seen in FIG. 27, which shows a top view of the tape 410 and illustrates that the samples may be in the form of a circular spot, an elongated line or other suitable formation depending on the collector nozzle, substrate tape 410 indexing method and other similar factors.

The collected sample is then transported by the belt the optical interrogation station 404, which illustrates the use of a first imaging station 422 located between the collection nozzle of the sample collection station 402 and a second imaging station 424, e.g., a Raman interrogation objective. The first imaging station 422 may take visible, UV or other images of the sample as noted in greater detail herein, e.g., to target specific regions of the sample for further interrogation. These images are processed, e.g., by the system controller 420, to allow targeting of specific particles for interrogation by the second imaging station 424. In the second imaging station 424, a suitable targeted interrogation is performed, e.g., by using a Raman laser interrogation beam arranged as a spot, e.g., for stepped movement of the tape substrate 410, or a focused line, e.g., for continuous movement of the tape substrate 410. A line focused laser can accumulate spectra from multiple spots along an illumination line at one time. The first and second imaging stations 422, 424 are illustrated as separate for clarity of illustration, but may, in practice, be implemented as separate stations, or as a single optical station, such as the optical interrogation device 70 described with reference to FIG. 4.

Figure 28:
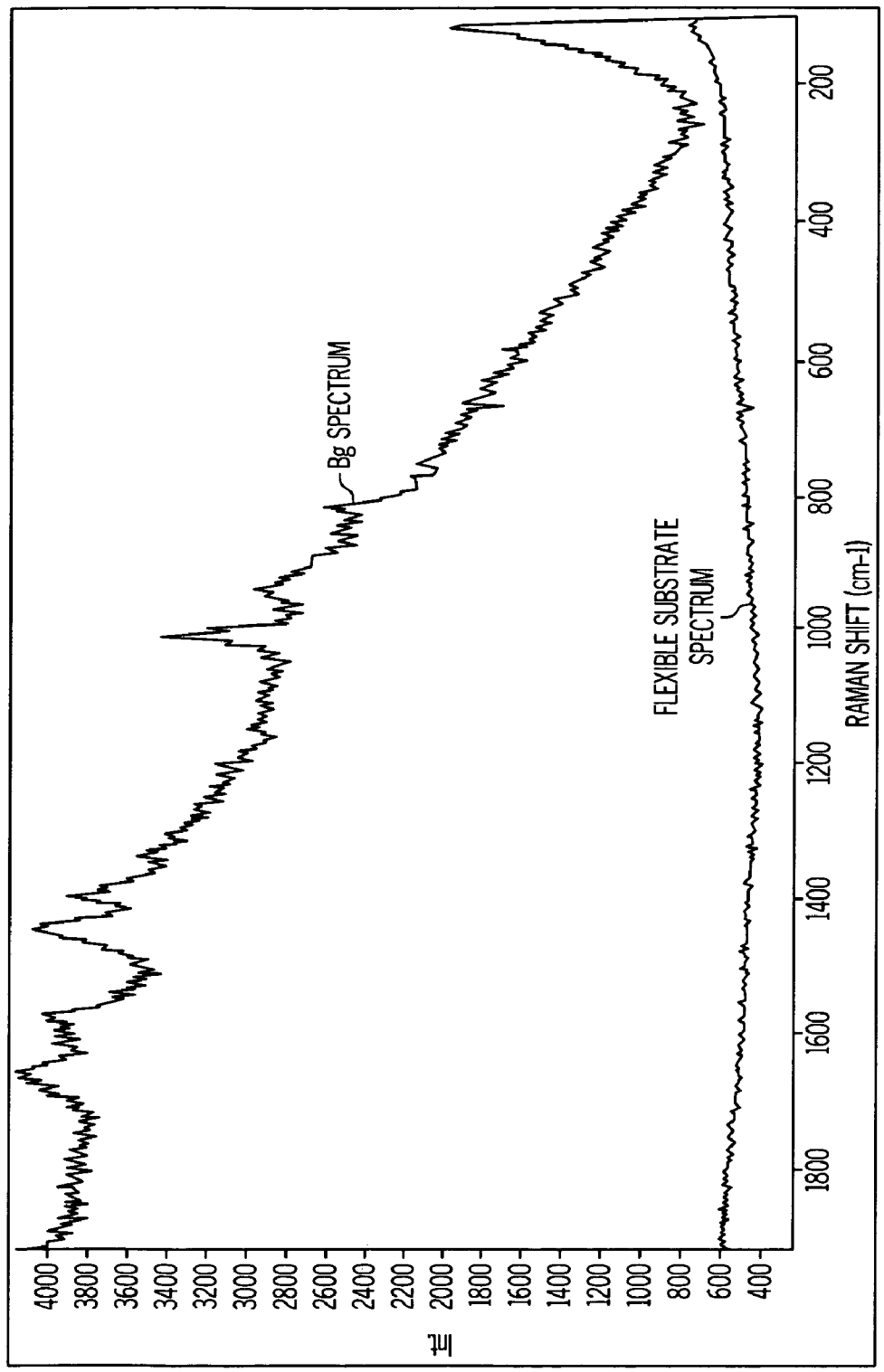
FIG. 28 is a plot of a Bg spectrum relative to the flexible tape.

Referring to FIG. 28 a graph 430 is presented showing a Raman spectrum of a single *Bacillus globigii* (Bg) spore, which was analyzed from a sample under Nicolet Omega Raman spectroscopy (Thermo Electrom Corporation, Madison, Wis.). The spectrum is a 30 second spectrum acquired with a Helium-Neon laser. The spectral results show that the substrate can provide a high signal and low noise sample spectrum, which is sufficient to be used for sample signature characterization and sample identification.

In order to overcome the sample positioning burden when micro-movement of the sample substrate is necessary during analysis of a sample at the optical interrogation station 404, the movement of the tape substrate 410 may be independent at each tape station. One method to achieve this is to compartmentalize the tape substrate 410. If the tape substrate 410 is mounted on a cassette via the recording tape reels 412, then the tape substrate 410 may move easily from the collection station 402 to the optical interrogation station 404 in a single large move.

Figure 29:
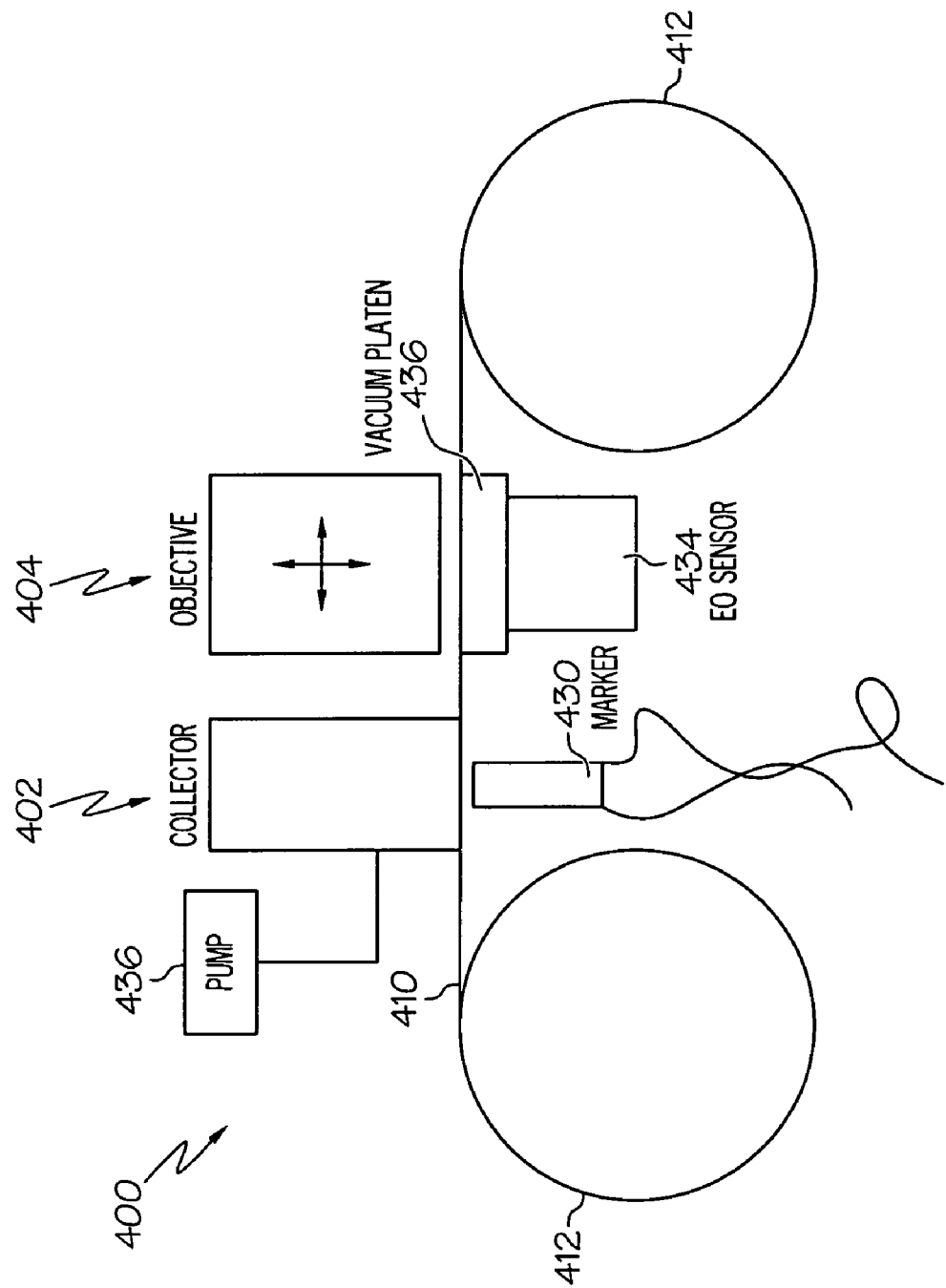
FIG. 29 is a schematic side view of the system of FIG. 25 illustrating a registration and alignment system for positioning a collected sample.

Referring to FIG. 29, when the tape substrate 410 moves underneath the collector in the collector station 402, a mechanical registration occurs, placing the deposited sample on the substrate within a certain area, e.g., to approximately 100 µm accuracy. To correctly position or reposition the sample spot on the tape substrate 410, the tape is positioned and a vacuum pump 430 is started. The vacuum pump 430 causes a vacuum that pulls the tape substrate 410 towards the collector of the collection station 402 and holds the tape in place during the collection process. While the collector station 402 deposits a sample onto the tape substrate 410, a marking device 430 places registration mark, e.g., as a spot on the underside of the tape substrate 410 at a fixed location relative to the center of the spot.

When the collection is complete, the vacuum pump 430 is turned off, which allows the tape substrate 410 to drop slightly away from the collector of the collection station 402. The tape substrate 410 is moved forward until the registration mark is detected by a sensor 434, e.g., an electro-optic (EO) sensor. Upon detection of a signal from the sensor 434, the optical interrogation station 404 draws the tape substrate 410 onto the vacuum platen 436 and is held in place for analysis as set out more fully herein. The vacuum platen 436 should allow control over the placement of the tape substrate 410 and corresponding sample 410 to the accuracy needed by the subsystem (usually better than 0.1 µm).

In this implementation, the objective of the optical interrogation station 404 may have to move to analyze the sample. However, moving the objective reduces and/or eliminates the concern about the tape substrate 410 stretching or the wraps of the tape substrate 410 on the spool of the substrate tape reels 412 tightening beyond tolerable limits. By using a vacuum, e.g., as drawn by the vacuum pump 430, a system can be realized with minimal hardware. Further, when interrogating the sample, a laser spot, e.g., used for Raman analysis, can be either a line focus which interrogates all particles in the illuminated line or a laser beam spot the scans over a line.

In another exemplary aspect of the present invention, a reel to reel cassette is used to collect the sample on a location on the tape as described herein. However, without moving the tape in the cassette the cassette is then moved to the next station. The tape is then examined successively at optical station one or optical station two. The use of separate cassettes may allow more accurate initial positioning of the tape in the optical system. In addition, the use of separate tapes for each station requires only a small advancement of the tape for each sample spot. The small advancement in the tape reduces the required size of the cassette.)

Miscellaneous and Additional Features

The biological and chemical detection system 10 may be arranged in the housing 12 so as to be readily portable. In critical applications, the biological and chemical detection system 10 may be provided with a backup battery so that the system can withstand an unplanned power interruption for predetermined periods without damage. Moreover, the biological and chemical detection system 10 may be operable over a wide range of temperatures, humidity, weather and other environmental conditions.

Methods of Operating a Biological or Chemical Particulate Identification System

Figure 30:
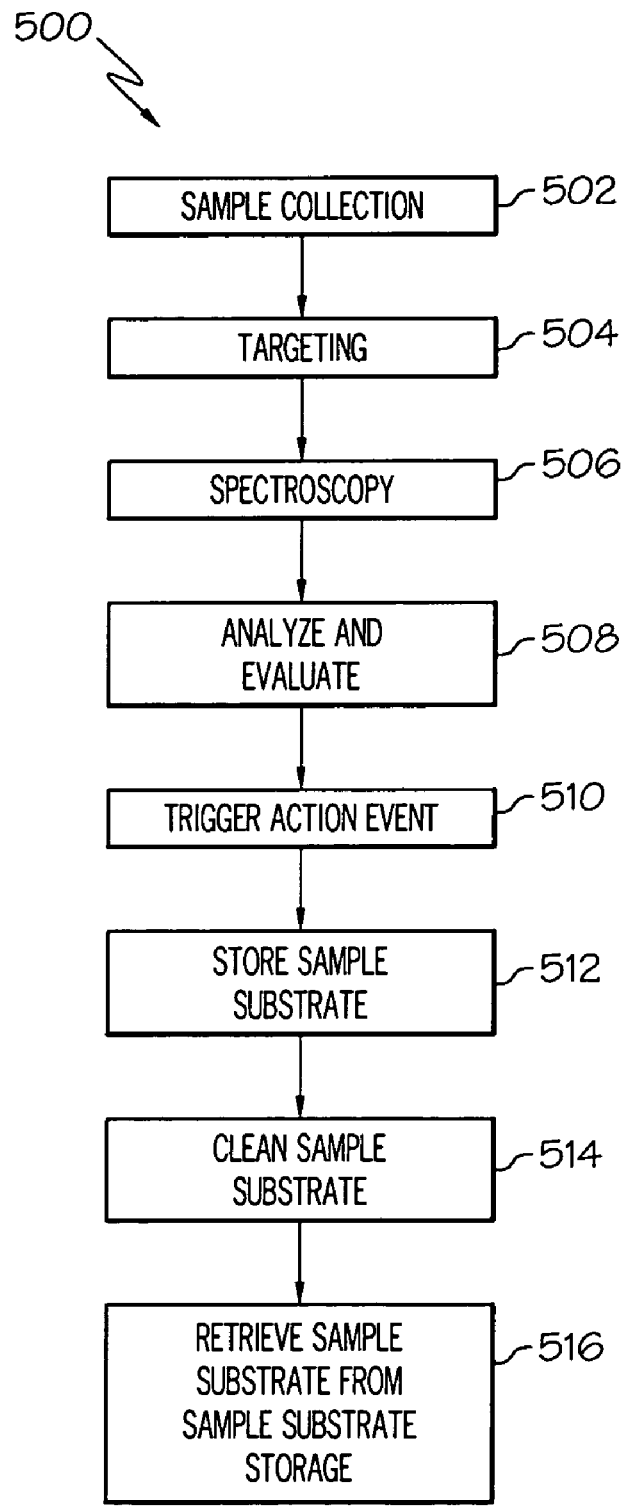
FIG. 30 is a flow chart of an exemplary method of operating the biological and chemical detection system.

With reference to FIG. 30 a method 500 of performing real time, or near real-time biological detection comprises collecting a sample at 502, such as using a collection station 14, 402. After a sample is collected, one or more specific locations within the sample are targeted at 504. As noted above, one technique to identify further field(s) of view and/or specific target locations within a sample area is to excite at least a portion of the sample area with a light source and make target decisions based upon the fluorescent, bright field, darkfield, etc., signal reflected back from the sample area. Further, particulate size and/or shape, spectral content and other factors, such as derived from trend analysis may be considered. After determining specific target locations of interest within the sample area at 504, e.g., by analyzing particulates in one or more fields of view, a targeted spectral analysis is performed at 506 at those determined target locations, e.g., using a spectrometer 88.

The results of the spectrometer measurements are analyzed and evaluated at 508. If a biological or chemical particulate of interest is located, an action event is triggered at 510, such as sounding an alarm, sending a message etc. Upon completion of the sample interrogation, the sample substrate may be stored at 512. Optionally the sample substrate may be cleaned at 514 and recycled. Still further, a previously analyzed sample substrate may be retrieved from the biological and chemical detection system for further analysis at 516, e.g., by retrieving a sample slide from a storage location or from rewinding a corresponding tape substrate to retrieve the desired sample. The above process may repeat as necessary or until all available sample substrates have been used and stored.

The system may provide the interrogation results of positive identification of particulates of interest, e.g., via a suitable display or printed output, in a relatively quick time frame. A total cycle time from start of sample collection to the completion of the sample analysis may require for example, approximately 18 minutes or less, where the probability of accurate detection is on the order of 90 to 99 percent, with a false positive detection percentage of one percent or less, and preferably less than 0.1 percent. Where speed is critical, near real-time identification of threat particulates may be realized, e.g., by adjusting operating set points of the system described more fully herein. Within the cycle time, the sample collection time at the collection station 14 may typically comprise from approximately 15 seconds to approximately 5 minutes. Samples collected too quickly may adversely affect the signal to noise ratio of the system. Likewise, samples collected too slowly may overly dampen the response time of the system. The total time and statistical probability of accurate identification will likely depend upon a number of factors including the ambient concentration of particulates of interest and the rate of particulate buildup.

Figure 31:
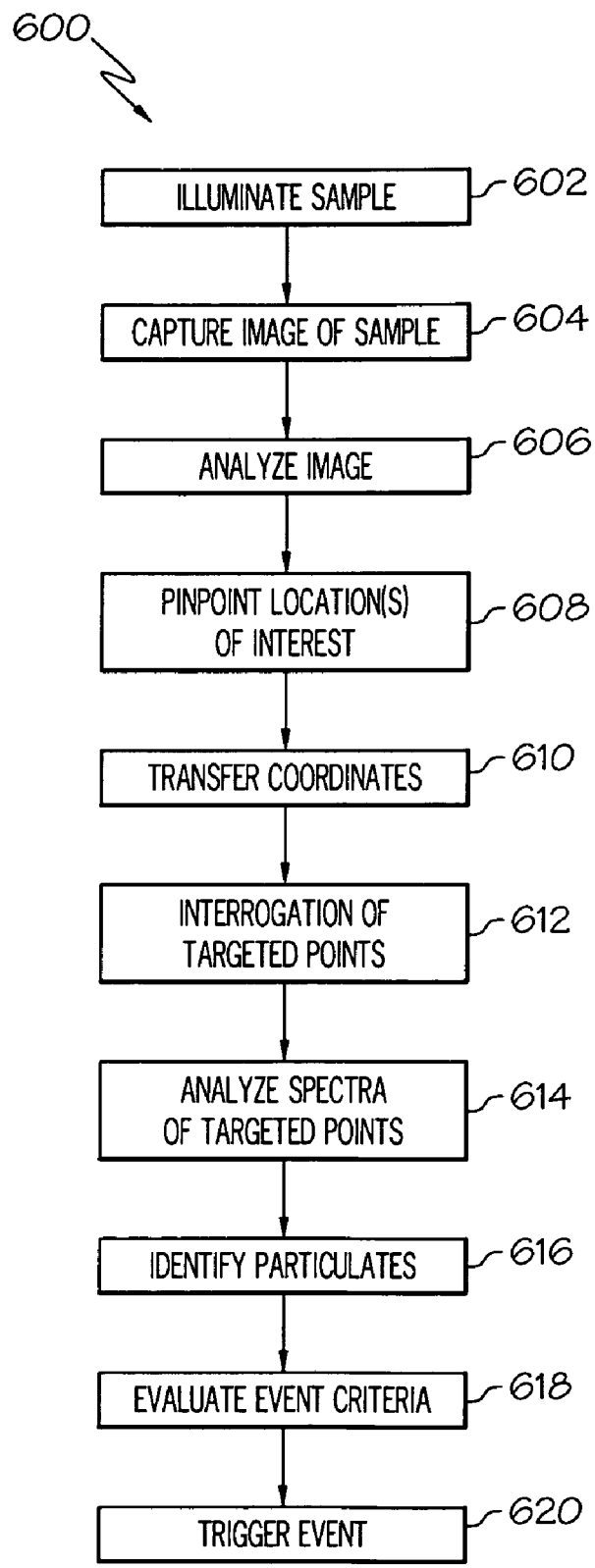
FIG. 31 is a flow chart of an exemplary method of operating the biological and chemical detection system.

Referring to FIG. 31, a method 600 for targeting locations within a sample area comprises illuminating at least a portion of the sample area at 602, e.g., using ultraviolet, near ultraviolet or visible light. An image of the exited sample area is captured at 604. The image, e.g., a fluorescent image, is analyzed at 606, e.g., by contrast level, edge detection and other suitable processing techniques, to determine one or more target locations of interest at 608. The coordinates of the target locations of interest are transferred to a spectrometer at 610 and the spectrometer interrogates the target locations of interest at 612. The spectral measurements are analyzed at 614 and particulates are identified at 616, e.g., based upon analyzing fingerprints using a classifier system. Event criteria are analyzed at 618 to determine whether a biological or chemical particulate of interest was identified in the sample. Based upon the results to the event criteria, a trigger event may be executed at 620.

Figure 32:
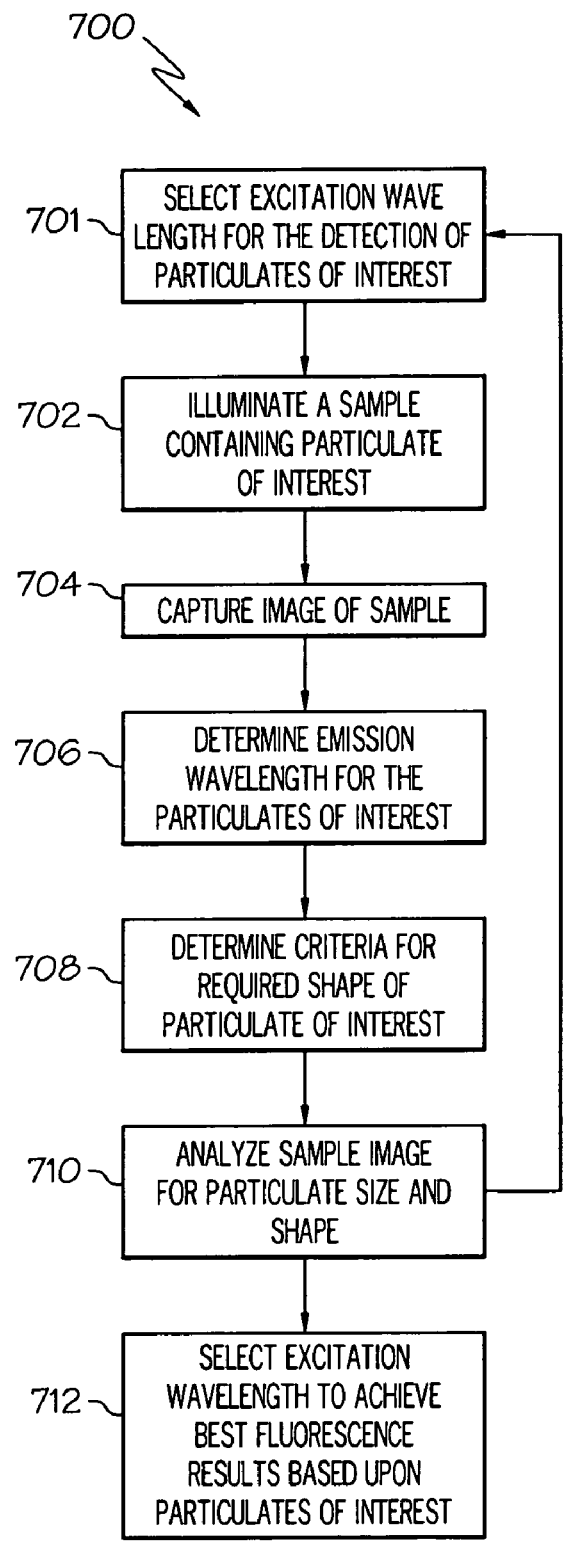
FIG. 32 is a flow chart of an exemplary approach to determine operating parameters of an optical interrogation station which may be used with the biological and chemical detection system.

As noted above, when using fluorescence, different excitation frequencies will likely result in different emission characteristics for a given biological material. Referring to FIG. 32, a method 700 of determining satisfactory parameters for using fluorescence to target a sample area comprises selecting an excitation wavelength at 702. A sample that contains the particulates of interest is illuminated at the selected excitation wavelength at 704 and an image is captured of the fluorescence at 706. Further, the emission wavelength for the particulates of interest is determined at 708. A criteria is established for the required shape of the particulates of interest at 710 and the sample image is analyzed against the previously established size and shape criteria at 712. The above steps are repeated for one or more excitation wavelengths and one or more emission wavelengths. After all desired excitation and emission wavelength combinations have been analyzed, a selection is made of the particular excitation wavelength that achieves the best fluorescence results.

According to various embodiments of the present invention, the biological and chemical detection system 10 can be utilized to detect biological and chemical agents and perform ambient particulate matter characterization and source identification. The biological and chemical detection system 10 is suitable for atmospheric chemistry research, tobacco smoke studies, indoor air particle measurements including indoor mold characterization, heating, refrigeration, and air conditioning analysis and other applications including those noted more fully throughout the specification.

The flowchart, schematic and block diagrams in the Figures illustrate the architecture, functionality, and operation of various embodiments of the present invention. In this regard, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by hardware or combinations of hardware and computer instructions, such that the instructions, which execute via a suitable processor or other programmable data processing apparatus, create means for implementing the functions/acts specified in the flowchart and/or block diagram block or blocks.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Having thus described the invention of the present application in detail and by reference to preferred embodiments thereof, it will be apparent that modifications and variations are possible without departing from the scope of the invention defined in the appended claims.

What is claimed is:

1. A biological and chemical detection system comprising:
   a collector configured to deposit particulates drawn from a fluid stream onto a sample substrate to define a sample area;
   a first optical device configured to derive first data relative to at least a portion of said sample area, wherein said first data comprises at least one of a fluorescence image, a bright field image or a darkfield image and said processor determines each target location based at least in part, upon a measured contrast of said first data;
   a processor configured to analyze said first data to determine at least one target location within said sample area; and
   a second optical device configured to interrogate said sample area at each determined target location to produce interrogation data;
   wherein said processor is further configured to determine whether said sample area includes predetermined biological or chemical particulates of interest based upon an analysis of said interrogation data and trigger an event if said predetermined biological or chemical particulates of interest are identified.

2. The biological and chemical detection system according to claim 1, wherein said first data further comprises at least two images at different wavelengths.

3. A biological and chemical detection system comprising:
   a collector configured to deposit particulates drawn from a fluid stream onto a sample substrate to define a sample area;
   a first optical device configured to derive first data relative to at least a portion of said sample area;

a processor configured to analyze said first data to determine at least one target location within said sample area, wherein said processor selects each target location based at least in part, upon an analysis of said first data to identify particulates having at least one of a particular size range or general shape; and a second optical device configured to interrogate said sample area at each determined target location to produce interrogation data;

wherein said processor is further configured to determine whether said sample area includes predetermined biological or chemical particulates of interest based upon an analysis of said interrogation data and trigger an event if said predetermined biological or chemical particulates of interest are identified.

4. A biological and chemical detection system comprising:

a collector configured to deposit particulates drawn from a fluid stream onto a sample substrate to define a sample area;

a first optical device configured to derive first data relative to at least a portion of said sample area, wherein said first optical device comprises a spectrometer or optical filter;

a processor configured to analyze said first data to determine at least one target location within said sample area, wherein each target location is selected based upon identifying at least one particulate having a spectral signature in a predetermined spectral range comprising at least one of a C-H stretching region located between approximately 2700 cm−1 and 3100 cm−1, a C-H deformation band between approximately 1390 cm−1 and 1500 cm−1 and an Amide I band between approximately 1590 cm−1 and 1750 cm−1; and a second optical device configured to interrogate said sample area at each determined target location to produce interrogation data;

wherein said processor is further configured to determine whether said sample area includes predetermined biological or chemical particulates of interest based upon an analysis of said interrogation data and trigger an event if said predetermined biological or chemical particulates of interest are identified.

5. The biological and chemical detection system according to claim 4, wherein each target location identifies an individual particulate and said second optical device comprises a spectrometer that is configured to interrogate each said individual particulate.

6. The biological and chemical detection system according to claim 4, wherein said second optical device comprises a Raman spectrometer configured to interrogate each target location in an area of approximately two microns or less.

7. A biological and chemical detection system comprising:

a collector configured to deposit particulates drawn from a fluid stream onto a sample substrate to define a sample area;

a first optical device configured to derive first data relative to at least a portion of said sample area;

a processor configured to analyze said first data to determine at least one target location within said sample area; and a second optical device configured to interrogate said sample area at each determined target location to produce interrogation data;

wherein said processor is further configured to determine whether said sample area includes predetermined biological or chemical particulates of interest based upon an analysis of said interrogation data and trigger an event if said predetermined biological or chemical particulates of interest are identified and said processor modifies criteria utilized to select each target location based at least in part, upon trend data that is collected across the analysis of multiple samples.

8. The biological and chemical detection system according to claim 7, wherein said processor is further configured to utilize a classifier system in analyzing said interrogation data.

9. A biological and chemical detection system comprising:

a collector configured to deposit particulates drawn from a fluid stream onto a sample substrate to define a sample area;

a first optical device configured to derive first data relative to at least a portion of said sample area, wherein said first data comprises images from a plurality of fields of view within said sample area;

a processor configured to analyze said first data to determine at least one target location within said sample area, wherein said processor is configured to select target locations that pinpoint individual particulates of interest from said plurality of fields of view; and a second optical device configured to interrogate said sample area at each determined target location to produce interrogation data;

wherein said processor is further configured to determine whether said sample area includes predetermined biological or chemical particulates of interest based upon an analysis of said interrogation data and trigger an event if said predetermined biological or chemical particulates of interest are identified.

10. The biological and chemical detection system according to claim 9, wherein said processor considers multiple fluorescence wavelengths when determining specific target locations.

11. A biological and chemical detection system comprising:

a collector configured to deposit particulates drawn from a fluid stream onto a sample substrate to define a sample area;

a first optical device configured to derive first data relative to at least a portion of said sample area;

a processor configured to analyze said first data to determine at least one target location within said sample area, wherein said processor filters said first data for fluorescent particulate data and further filters said fluorescent particulate data within a predetermined size range to result in remaining filtered particulate data, wherein said target locations are selected from remaining filtered particulate data; and a second optical device configured to interrogate said sample area at each determined target location to produce interrogation data;

wherein said processor is further configured to determine whether said sample area includes predetermined biological or chemical particulates of interest based upon an analysis of said interrogation data and trigger an event if said predetermined biological or chemical particulates of interest are identified.

12. A method of analyzing a sample for biological or chemical particulates of interest comprising:

collecting particulates drawn from a fluid stream onto a sample substrate to define a sample area;

utilizing a first optical device to derive first data relative to at least a portion of said sample area;

analyzing said first data to determine at least one target location within said sample area by extracting contrast information from said first data by analyzing at least one of a fluorescence image, a bright field image or a darkfield image;

utilizing a second optical device to interrogate said sample area at each determined target location to produce interrogation data;

determining whether said sample area includes predetermined biological or chemical particulates of interest based upon an analysis of said interrogation data; and triggering an event if said predetermined biological or chemical particulates of interest are identified.

13. The method according to claim 12, wherein said analyzing at least one of a fluorescence image, a bright field image or a darkfield image comprises considering at least two images at different wavelengths when determining specific target locations.

14. The method according to claim 12, wherein said collecting particulates drawn from a fluid stream onto a sample substrate to define a sample area comprises filtering particulates in said fluid stream such that particulates collected onto said sample substrate are substantially within a predetermined size range.

15. The method according to claim 12, wherein said analyzing said first data to determine at least one target location within said sample area comprises collecting said first data as images from a plurality of fields of view within said sample area, and selecting target locations that pinpoint individual particulates of interest from particulates identified in said plurality of fields of view.

16. The method according to claim 12, wherein said utilizing a second optical device to interrogate said sample area at each determined target location to produce interrogation data comprises pinpointing a single particulate within each target location for interrogation.

17. A method of analyzing a sample for biological or chemical particulates of interest comprising:
collecting particulates drawn from a fluid stream onto a sample substrate to define a sample area;
utilizing a first optical device to derive first data relative to at least a portion of said sample area;
analyzing said first data to determine at least one target location within said sample area by considering particulate size and/or shape when determining said at least one target location;
utilizing a second optical device to interrogate said sample area at each determined target location to produce interrogation data;
determining whether said sample area includes predetermined biological or chemical particulates of interest based upon an analysis of said interrogation data; and
triggering an event if said predetermined biological or chemical particulates of interest are identified.

18. A method of analyzing a sample for biological or chemical particulates of interest comprising:
collecting particulates drawn from a fluid stream onto a sample substrate to define a sample area;
utilizing a first optical device to derive first data relative to at least a portion of said sample area;
analyzing said first data to determine at least one target location within said sample area by utilizing a spectrometer or optical filter to identify each target location based upon identifying at least one particulate having a spectral signature in a predetermined spectral range comprising at least one of a C-H stretching region located between approximately 2700 cm−1 and 3100 cm−1, a C-H deformation band between approximately 1390 cm−1 and 1500 cm−1 and an Amide I band between approximately 1590 cm−1 and 1750 cm−1;
utilizing a second optical device to interrogate said sample area at each determined target location to produce interrogation data;
determining whether said sample area includes predetermined biological or chemical particulates of interest based upon an analysis of said interrogation data; and
triggering an event if said predetermined biological or chemical particulates of interest are identified.

19. A method of analyzing a sample for biological or chemical particulates of interest comprising:
collecting particulates drawn from a fluid stream onto a sample substrate to define a sample area;
utilizing a first optical device to derive first data relative to at least a portion of said sample area;
analyzing said first data to determine at least one target location within said sample area;
utilizing a second optical device to interrogate said sample area at each determined target location to produce interrogation data;
determining whether said sample area includes predetermined biological or chemical particulates of interest based upon an analysis of said interrogation data;
triggering an event if said predetermined biological or chemical particulates of interest are identified; and
dynamically modifying criteria utilized to select each target location based at least in part, upon trend data that is collected across the analysis of multiple samples.

20. The method according to claim 19, wherein said determining whether said sample area includes predetermined biological or chemical particulates of interest based upon an analysis of said interrogation data comprises utilizing a classifier system having a plurality of spectral fingerprints with known constituents and properties.

21. A method of analyzing a sample for biological or chemical particulates of interest comprising:
illuminating at least a portion of a sample area;
capturing at least one of a fluorescent image, a bright field image or a darkfield image of the illuminated portion of said sample area;
analyzing said captured images by contrast level;
pinpointing locations of high contrast within said captured images;
selecting at least one target particulate within the illuminated portion of said sample area;
transferring coordinates of each selected target particulate to a spectrometer or optical filter;
individually interrogating each selected target particulate using said spectrometer to generate interrogation data;
evaluating said interrogation data; and
triggering an event if a biological or chemical particulate of interest is identified from the evaluation of said interrogation data.

22. The method according to claim 21, wherein said sample area is illuminated with at least one of an ultraviolet light source or a visible light source.

23. The method according to claim 21, wherein said target particulates are selected based upon a set of criteria that includes contrast level and at least one of particulate size or particulate shape.

24. The method according to claim 21, wherein said interrogation data is evaluated using a classifier comprised of a library of biological or chemical particulates of interest with known constituents and properties.

25. The method according to claim 21, wherein said individually interrogating each selected target particulate using said spectrometer to generate interrogation data and evaluating said interrogation data comprises using a Raman spectrometer to pinpoint individual target particulates and evaluate said interrogation data for a Raman spectral fingerprint.

* * * * *

UNITED STATES PATENT AND TRADEMARK OFFICE
CERTIFICATE OF CORRECTION

| | | |
|---|---|---|
| PATENT NO. | : 7,532,314 B1 | Page 1 of 1 |
| APPLICATION NO. | : 11/486861 | |
| DATED | : May 12, 2009 | |
| INVENTOR(S) | : Rodney S. Black et al. | |

It is certified that error appears in the above-identified patent and that said Letters Patent is hereby corrected as shown below:

Column 5, line 38, "is the air viscosity and d $_{impactor}$ or is the" should read --is the air viscosity and d $_{impactor}$ is the--;

Column 10, line 49, "between approximately 1590 cm-1 and" should read --between approximately 1590 cm$^{-1}$ and--;

Column 12, line 1, "approximately 2 cm-1 to 12" should read --approximately 2 cm$^{-1}$ to 12--;

Column 32, line 49, "covering 2000-4000 cm cm$^{-1m}$, the diffracted" should read --covering 2000-4000 cm$^{-1m}$, the diffracted--;

Signed and Sealed this
Ninth Day of August, 2011

David J. Kappos
*Director of the United States Patent and Trademark Office*